US008410109B2

(12) United States Patent
Wong et al.

(10) Patent No.: US 8,410,109 B2
(45) Date of Patent: *Apr. 2, 2013

(54) PHARMACEUTICAL COMPOSITIONS FOR THE PREVENTION AND TREATMENT OF COMPLEX DISEASES AND THEIR DELIVERY BY INSERTABLE MEDICAL DEVICES

(75) Inventors: Norman C. W. Wong, Calgary (CA); Henrik C. Hansen, Calgary (CA); Fabrizio S. Chiacchia, Calgary (CA); Jan O. Johansson, Danville, CA (US)

(73) Assignee: Resverlogix Corp., Calgary, Alberta (CA)

( * ) Notice: Subject to any disclaimer, the term of this patent is extended or adjusted under 35 U.S.C. 154(b) by 44 days.

This patent is subject to a terminal disclaimer.

(21) Appl. No.: 11/990,162

(22) PCT Filed: Jul. 28, 2006

(86) PCT No.: PCT/US2006/029827
§ 371 (c)(1),
(2), (4) Date: Feb. 7, 2008

(87) PCT Pub. No.: WO2007/016525
PCT Pub. Date: Feb. 8, 2007

(65) Prior Publication Data
US 2009/0029987 A1 Jan. 29, 2009

Related U.S. Application Data

(60) Provisional application No. 60/704,035, filed on Jul. 29, 2005.

(51) Int. Cl.
*A61K 31/497* (2006.01)
(52) U.S. Cl. .............. 514/253.05; 514/233.8; 514/302; 514/309; 514/312; 514/300; 546/283.1; 546/153; 546/144; 546/122; 546/115; 544/128
(58) Field of Classification Search ............... 514/233.8, 514/310, 302, 309, 312, 253.05, 300; 546/283.1, 546/153, 144, 122, 115; 544/128
See application file for complete search history.

(56) References Cited

U.S. PATENT DOCUMENTS

| | | | |
|---|---|---|---|
| 2,065,593 A | 12/1936 | Lubs | |
| 2,065,900 A | 12/1936 | Laska et al. | |
| 2,071,329 A | 2/1937 | Brown | |
| 3,251,837 A | 5/1966 | Holland | |
| 3,600,394 A | 8/1971 | Coyne et al. | |
| 3,773,946 A | 11/1973 | Creger | |
| 3,930,024 A | 12/1975 | Creger | |
| 3,965,128 A | 6/1976 | Fürst et al. | |
| 4,613,593 A | 9/1986 | Yamatsu et al. | |
| 4,689,344 A | 8/1987 | Bar-Tana | |
| 4,711,896 A | 12/1987 | Bar-Tana et al. | |
| 4,825,005 A | 4/1989 | Frey et al. | |
| 5,124,337 A | 6/1992 | Dugar et al. | |
| 5,126,351 A | 6/1992 | Luzzio et al. | |
| 5,244,904 A | 9/1993 | Nagase et al. | |
| 5,354,749 A | 10/1994 | Dressel et al. | |
| 5,407,942 A | 4/1995 | Dressel et al. | |
| 5,446,071 A | 8/1995 | Grese | |
| 5,480,883 A | 1/1996 | Spada et al. | |
| 5,539,119 A | 7/1996 | Nagase et al. | |
| 5,576,322 A | 11/1996 | Takase et al. | |
| 5,595,974 A | 1/1997 | Tomaru | |
| 5,693,652 A | 12/1997 | Takase et al. | |
| 5,707,987 A | 1/1998 | Nakagawa et al. | |
| 5,733,913 A | 3/1998 | Blankley | |
| 5,756,344 A | 5/1998 | Onda et al. | |
| 5,756,544 A | 5/1998 | Bisgaier et al. | |
| 5,756,736 A | 5/1998 | Arzeno et al. | |
| 5,756,763 A | 5/1998 | Takeuchi et al. | |
| 5,763,414 A | 6/1998 | Bok et al. | |
| 5,783,577 A | 7/1998 | Houghten et al. | |
| 5,792,461 A | 8/1998 | Bok et al. | |
| 5,792,902 A | 8/1998 | Benoit et al. | |
| 5,801,180 A | 9/1998 | Takase et al. | |
| 5,817,674 A | 10/1998 | Clemence et al. | |
| 5,854,264 A | 12/1998 | Anthony et al. | |
| 5,877,208 A | 3/1999 | Bok et al. | |
| 5,922,866 A | 7/1999 | Miyata et al. | |

(Continued)

FOREIGN PATENT DOCUMENTS

| | | |
|---|---|---|
| AU | 719140 | 9/1998 |
| CA | 2104981 | 3/1994 |

(Continued)

OTHER PUBLICATIONS

Clauson-Kaas et al Reactions of 3,4-dihydor-2H-pyrrido[3,2-b]-1,4-oxazines, Acta Chemica Scandinavica, 1947-1973), vol. 25 Issue 8, pp. 3135-3143.*
Vippagunta et al. Advanced Drug Delivery Reviews, 48, 2001, p. 18.*
Patini et al ("Bioisosterism: A rational approach in Drug design", Chem. Rev. 1996, vol. 96, Issue 8, pp. 3147-3176).*
Chartier et al, No. 348-Synthesis of diazaflavones, bulletin de la Societe Chimique de France (1976), 11-12, pt 2), 1916-1918.*
Devitt et al, Journal of Organic Chemistry, (1961), 26, 4941-4944.*
Barrans et al., "Pre-β HDL: Structure and Metabolism," *Biochem Biophys Acta* 1300:73-85 (1996).
Barter et al., "High Density Lipoproteins and Coronary Heart Disease," *Atherosclerosis* 121:1-12 (1996).
Chakrabarty et al., "Induction of apoptosis in human cancer cell lines by diospyrin, a plant-derived bisnaphthoquinonoid, and its synthetic derivatives," *Cancer Letters* 188:85-93, (2002).
Cho et al., "Synthesis and Antitumor Activity of 3-Arylisoquinoline Derivatives," *Arch Pharm Res* 20:264-268 (1997).

(Continued)

*Primary Examiner* — Brandon Fetterolf
*Assistant Examiner* — Jean Cornet
(74) *Attorney, Agent, or Firm* — Finnegan, Henderson, Farabow, Garrett & Dunner, LLP

(57) ABSTRACT

The present invention relates to polyphenol-like compounds that are useful for inhibiting VCAM-1 expression, MCP-1 expression and/or SMC proliferation in a mammal. The disclosed compounds are useful for regulating markers of inflammatory conditions, including vascular inflammation, and for treatment and prevention of inflammatory and cardiovascular diseases and related disease states.

2 Claims, No Drawings

U.S. PATENT DOCUMENTS

| | | |
|---|---|---|
| 5,965,556 A | 10/1999 | Takeuchi et al. |
| 6,022,901 A | 2/2000 | Goodman |
| 6,048,903 A | 4/2000 | Toppo |
| 6,054,435 A | 4/2000 | Or et al. |
| 6,133,241 A | 10/2000 | Bok et al. |
| 6,165,984 A | 12/2000 | Bok et al. |
| 6,168,776 B1 | 1/2001 | Klunk et al. |
| 6,239,114 B1 | 5/2001 | Guthrie et al. |
| 6,291,456 B1 | 9/2001 | Stein et al. |
| 6,303,629 B1 | 10/2001 | Kun |
| 6,340,759 B1 | 1/2002 | Ueno et al. |
| 6,414,037 B1 | 7/2002 | Pezzuto et al. |
| 6,455,577 B2 | 9/2002 | Bok et al. |
| 6,482,479 B1 | 11/2002 | Dübal et al. |
| 6,512,161 B1 | 1/2003 | Rouy et al. |
| 6,541,045 B1 | 4/2003 | Charters et al. |
| 6,541,522 B2 | 4/2003 | Inman et al. |
| 6,548,548 B2 | 4/2003 | Campbell et al. |
| 6,613,772 B1 | 9/2003 | Schindler et al. |
| 6,635,642 B1 | 10/2003 | Jackson et al. |
| 6,673,780 B2 | 1/2004 | Dasseux et al. |
| 6,703,422 B2 | 3/2004 | Dasseux et al. |
| 7,087,612 B2 | 8/2006 | Rodriguez Sarmiento et al. |
| 7,173,128 B2 | 2/2007 | Ravichandran et al. |
| 7,244,776 B2 | 7/2007 | Ravichandran et al. |
| 7,846,915 B2 | 12/2010 | Wong et al. |
| 8,053,440 B2 | 11/2011 | Hansen |
| 8,093,273 B2 | 1/2012 | Wong et al. |
| 8,114,995 B2 | 2/2012 | Hansen et al. |
| 2002/0091263 A1 | 7/2002 | Trova |
| 2003/0064967 A1 | 4/2003 | Luchoomun |
| 2003/0068526 A1 | 4/2003 | Kamatani et al. |
| 2003/0072964 A1 | 4/2003 | Kwong et al. |
| 2003/0171429 A1 | 9/2003 | Chen et al. |
| 2004/0001834 A1 | 1/2004 | Kim et al. |
| 2004/0033480 A1 | 2/2004 | Wong |
| 2004/0058903 A1 | 3/2004 | Takasugi et al. |
| 2004/0097493 A1 | 5/2004 | Chen |
| 2004/0198750 A1 | 10/2004 | Green et al. |
| 2004/0235888 A1 | 11/2004 | Yamamori et al. |
| 2004/0242615 A1 | 12/2004 | Yamamori et al. |
| 2005/0043300 A1 | 2/2005 | Middleton et al. |
| 2005/0080021 A1 | 4/2005 | Tucker et al. |
| 2005/0080024 A1 | 4/2005 | Tucker et al. |
| 2005/0261319 A1 | 11/2005 | Deuschle et al. |
| 2006/0116364 A1 | 6/2006 | Hamaoka et al. |
| 2006/0205767 A1* | 9/2006 | Wong et al. .................. 514/303 |
| 2007/0099826 A1 | 5/2007 | Wong et al. |
| 2007/0185160 A1 | 8/2007 | Hattori et al. |
| 2007/0218155 A1 | 9/2007 | Kuhrts |
| 2011/0082176 A1 | 4/2011 | Wong et al. |
| 2011/0201608 A1 | 8/2011 | Hoffman et al. |
| 2011/0294807 A1 | 12/2011 | Hansen |
| 2012/0040954 A1 | 2/2012 | Hansen |
| 2012/0059002 A1 | 3/2012 | Hansen et al. |

FOREIGN PATENT DOCUMENTS

| | | |
|---|---|---|
| CA | 2345406 | 4/2000 |
| CN | 1067070 | 6/2001 |
| DE | 4215588 | 11/1993 |
| DE | 19651099 | 6/1998 |
| DE | 19756388 | 6/1999 |
| DE | 19934799 | 2/2001 |
| EP | 0182213 B1 | 9/1990 |
| EP | 0258190 B1 | 11/1990 |
| EP | 0407217 A1 | 1/1991 |
| EP | 0488602 A1 | 6/1992 |
| EP | 0272455 B1 | 2/1993 |
| EP | 0375404 B1 | 2/1994 |
| EP | 0333175 B1 | 6/1994 |
| EP | 0343499 B1 | 7/1994 |
| EP | 0607439 B1 | 7/1994 |
| EP | 0409413 B1 | 8/1994 |
| EP | 0420511 B1 | 8/1994 |
| EP | 0 633 022 | 1/1995 |
| EP | 0569795 B1 | 4/1995 |
| EP | 0330108 B1 | 12/1995 |
| EP | 0747 051 | 12/1996 |
| EP | 0776893 B1 | 6/1997 |
| EP | 0643119 B1 | 4/2000 |
| EP | 1125908 A1 | 8/2001 |
| EP | 0498723 B1 | 9/2001 |
| EP | 1 195 378 | 4/2002 |
| EP | 1277738 A1 | 1/2003 |
| EP | 1398032 A1 | 3/2004 |
| EP | 1 418 164 | 5/2004 |
| EP | 1 426 046 | 6/2004 |
| EP | 1477481 A1 | 11/2004 |
| EP | 1637523 A1 | 3/2006 |
| EP | 1 757 594 A1 | 2/2007 |
| EP | 2005941 A2 | 12/2008 |
| FR | 2 244 492 | 4/1975 |
| FR | 2 244 493 | 4/1975 |
| GB | 472489 | 3/1936 |
| GB | 1 175 808 | 12/1969 |
| GB | 1 179 019 | 1/1970 |
| GB | 2292149 | 2/1996 |
| JP | 6-80656 | 3/1994 |
| JP | 741442 | 2/1995 |
| JP | 761942 | 3/1995 |
| JP | 7118241 | 5/1995 |
| JP | 7179380 | 7/1995 |
| JP | 1995-247289 | 9/1995 |
| JP | 7233109 | 9/1995 |
| JP | 10257678 | 10/1998 |
| JP | 2001-335476 | 4/2001 |
| JP | 2001-139550 | 5/2001 |
| JP | 2002249483 | 9/2002 |
| JP | 2004-511502 A | 4/2004 |
| JP | 2004203751 | 7/2004 |
| JP | 2004307440 | 11/2004 |
| WO | WO 91/18901 A1 | 12/1991 |
| WO | WO 92/09374 A1 | 6/1992 |
| WO | WO 92/18123 A2 | 10/1992 |
| WO | WO 92/20642 A1 | 11/1992 |
| WO | WO 92/21661 A1 | 12/1992 |
| WO | WO 93/07124 A1 | 4/1993 |
| WO | WO 93/08174 A1 | 4/1993 |
| WO | WO 94/14763 A1 | 7/1994 |
| WO | WO 95/03277 A1 | 2/1995 |
| WO | WO 95/23150 A1 | 6/1995 |
| WO | WO 96/15128 A2 | 5/1996 |
| WO | WO 96/31206 | 10/1996 |
| WO | WO 97/10221 A1 | 3/1997 |
| WO | WO 97/15308 | 5/1997 |
| WO | WO 97/28118 A1 | 6/1997 |
| WO | WO 97/28132 A1 | 8/1997 |
| WO | WO 97/28134 A1 | 8/1997 |
| WO | WO 97/29106 A1 | 8/1997 |
| WO | WO 97/48694 | 12/1997 |
| WO | WO 98/11438 A1 | 3/1998 |
| WO | WO 98/26127 A1 | 6/1998 |
| WO | WO 98/30530 A1 | 7/1998 |
| WO | WO 98/50370 A1 | 11/1998 |
| WO | WO 98/51307 | 11/1998 |
| WO | WO 98/51308 | 11/1998 |
| WO | WO 98/55124 | 12/1998 |
| WO | WO 99/00116 A2 | 1/1999 |
| WO | WO 99/11634 A1 | 3/1999 |
| WO | WO 99/18077 A1 | 4/1999 |
| WO | WO 99/29667 A1 | 6/1999 |
| WO | WO 00/23075 | 4/2000 |
| WO | WO 00/35865 | 6/2000 |
| WO | WO 00/44362 | 8/2000 |
| WO | WO 00/55168 A1 | 9/2000 |
| WO | WO 00/64888 A1 | 11/2000 |
| WO | WO 01/00554 | 1/2001 |
| WO | WO 01/60775 A1 | 8/2001 |
| WO | WO 01/82916 A2 | 11/2001 |
| WO | WO 01/83456 A1 | 11/2001 |
| WO | WO 02/32377 A2 | 4/2002 |
| WO | WO 02/044189 A1 | 6/2002 |
| WO | WO 02/074307 | 9/2002 |
| WO | WO 02/087556 | 11/2002 |
| WO | WO 02/096426 A1 | 12/2002 |
| WO | WO 03/007959 A1 | 1/2003 |

| | | |
|---|---|---|
| WO | WO 03/016292 A1 | 2/2003 |
| WO | WO 03/018008 A1 | 3/2003 |
| WO | WO 03/040256 A2 | 5/2003 |
| WO | WO 03/040257 A1 | 5/2003 |
| WO | WO 03/070236 A2 | 8/2003 |
| WO | WO 03/099274 A1 | 12/2003 |
| WO | WO 03/106435 | 12/2003 |
| WO | WO 2004/017920 A2 | 3/2004 |
| WO | WO 2004/032846 A2 | 4/2004 |
| WO | WO 2004/039795 | 5/2004 |
| WO | WO 2004/047755 | 6/2004 |
| WO | WO 2004/056355 | 7/2004 |
| WO | WO 2004/058717 | 7/2004 |
| WO | WO 2004/065392 | 8/2004 |
| WO | WO 2004/072042 | 8/2004 |
| WO | WO 2004/092196 A2 | 10/2004 |
| WO | WO 2004/094452 A2 | 11/2004 |
| WO | WO 2004/112710 | 12/2004 |
| WO | WO 2005/034960 | 4/2005 |
| WO | WO 2005/042712 A2 | 5/2005 |
| WO | WO 2005/075431 A1 | 6/2005 |
| WO | WO 2005/065183 A2 | 7/2005 |
| WO | WO 2005/066162 A1 | 7/2005 |
| WO | WO 2006/071095 A1 | 7/2006 |
| WO | WO 2006/105081 A2 | 10/2006 |
| WO | WO 2007/071055 A1 | 6/2007 |
| WO | WO 2008/152471 A1 | 12/2008 |
| WO | WO 2010/015520 A1 | 2/2010 |

OTHER PUBLICATIONS

Cho et al., "Synthesis and Comparative Molecular Field Analysis (CoMFA) of Antitumor 3-Arylisoquinoline Derivatives," *Bioorg Med Chem* 6(12):2449-2458 (1998).
Co-pending U.S. Appl. No. 11/670,238, filed Feb. 1, 2007, Inventors: Norman C.W. Wong et al.
Co-pending U.S. Appl. No. 11/254,420, filed Oct. 20, 2005, Inventors: Norman C.W. Wong et al.
Co-pending U.S. Appl. No. 11/255,103, filed Oct. 20, 2005, Inventors: Norman C.W. Wong et al.
Derwent English Language Abstract of DE 36 01 417.
Derwent English Language Abstract of EP 0 210 342.
Derwent English Language Abstract of EP 0 564 350.
Derwent English Language Abstract of EP 1 426 046.
Derwent English Language Abstract of FR 2 244 492.
Derwent English Language Abstract of JP 1995-247289.
Ferreira et al., "Diversity of Structure and Function in Oligomeric Flavanoids," *Tetrahedron* 48:1743-1803 (1992).
Gerritsen et al., "Flavenoids inhibit cytokine-induced endothelial cell adhesion protein gene expression," *American Journal of Pathology* 147:278-292 (1995).
Hazra et al., "New diospyrin derivatives with improved tumour inhibitory activity towards Ehrlich ascites carcinoma," *Med. Sci. Res*:351-353 (1994).
Hazra et al., "Synthesis of an antitumor derivative of diospyrin," *IRCS Med. Sci* 14:35-36 (1986).
Hertog et al., "Dietary Antioxidant Flavonoids and Risk of Coronary Heart Disease: One Zutphen Elderly Study," *Lancet* 342:1007-1011 (1993).
International Search Report and Written Opinion as issued in International Application No. PCT/CA2007/000146 mailed on Oct. 29, 2007.
International Search Report and Written Opinion as issued in International Application No. PCT/US2006/029827 mailed on Apr. 16, 2007.
International Search Report and Written Opinion as issued in International Application No. PCT/US2005/037719 mailed on Mar. 9, 2007.
International Search Report and Written Opinion as issued in International Application No. PCT/US2005/038048 mailed on Mar. 7, 2007.
Jeong et al., "Hypocholesterolemic Activity of Hesperetin Derivatives," *Bioorg. & Med. Chem. Lett.* 13:2663-2665 (2003).
Jin et al., "Antiplatelet and antithrombotic activities of CP201, a newly synthesized 1,4-naphthoquinone derivative," *Vascular Pharmacology* 41:35-41 (2004).

Kawamatsu et al., "2-Amino-4-phenylthiazole derivatives as anitatherogenic agents," *Eur. J. Med. Chem.* 16(4):355-362 (1981).
Kublak et al., "The preparation of the azaspirobicyclic system of discorhabdin C via an intramolecular phenolate alkylation," *Tet. Lett*, 31:3845-3848 (1990).
Lamon-Fava, "Genistein activates apolipoprotein A-I gene expression in the human hepatoma cell line Hep G2," *J. Nutrition* 130:2489-2492 (2000).
Lin et al., "Potential bioreductive alkylating agents. 7. Antitumor effects of phenyl-substituted 2-chloromethyl-3-phenyl-1,4-naphthoquinones,"*J. Med. Chem* 1339-1338 (1976).
Manach et al., "Polyphenols and prevention of cardiovascular diseases," *Curr Opin Lipidol* 1:77-84 (2005).
Meckes et al., "The effects of chrysin and pinostrobin, 2 flavonoids isolated from *Teloxys graveolens* leaves, on isolated guinea-pig ileum," *Phytomedicine* 5:459-463 (1998).
Middleton et al., "Quercetin hinhibits lipopolysaccaride-induced expression of endothelial cell intracellular adhesion molecule-1," *Int. Arch. Allergy. lmmunol* 107:435-436 (1995).
Patent Abstracts of Japan vol. 2000, No. 22, JP 2001-139550 (2001).
Patent Abstracts of Japan vol. 2002, No. 4, JP 2001 335476 (2002).
Patent Abstracts of Japan vol. 2000, No. 22, JP 2001 131151 (2001).
Rimando et al., "Pterostilbene, a new agonist for the peroxisome proliferator-activated receptor alpha-isoform, lowers plasma lipoproteins and cholesterol in hyercholesterolemic hamsters," *J. Agri. Food Chem.* 53(9):3403-3407 (2005).
Rose et al., "Oxygen Heterocycles. Part XIII. From 3-Arylisocoumarins to 3-Aryl-isoquinolines and 4-Aryl-5H-2,3-benzodiazepines," *J. Chem. Soc.* 2205-2208 (1968).
Theriault et al., "Modulation of hepatic lipoprotein synthesis and secretion by taxifolin, a plant flavonoid," *J. Lipid Res*. 41:1969-1979 (2000).
Van Der Goot et al., "The growth-inhibitory action of some 1-aminoisoquinolines and related compounds on mycoplasma gallisepticum," *Eur. J. Med. Chem.—Chimica Therapeutica* 10:603-606 (1975).
Walle, "Absorption and Metabolism of Flavonoids," *Free Radical Biol Med*. 36(7):829-837 (2004).
Woelle et al., Selective inhibition of tumor necrosis factor-induced vascular cell adhesion molecule-1 gene expression by a novel flavonoid: lack of effect on transcription factor NF-kappa-B, *Arterioscler. Thromb. Vasc. Biol.* 16(12):1501-1508 (1996).
Wurm et al., "1,4-naphthoquinones, XXVI: phenyl-1,4-naphthoquinone derivatives with the hydroxylation patterns of bioflavonoids," *Pharmazie* 52:739 (1997).
Wurm, "1 4 naphthoquinones XXI. 2-3 5 Di-Tert-Butyl-4-hydroxyphenyl-1 4-naphthoquinones as 5 lipoxygenase inhibitors," *Archiv der Pharmazie* 324:491-495 (1991).
Yardley et al., "In vitro activity of diospyrin and derivatives against *Leishmania donovani, Trypanosoma cruzi* and *Trypanosoma brucei brucei," Phytotherapy Research* 10:559-562 (1996).
Abdel-Jalil, R.J. et al., "Synthesis and Antitumor Activity of 2-Aryl-7-fluoro-6-(4-methyl-1-piperazinyl)-4(3H)-quinazolinones," *Heterocycles* 65(9):2061-2070 (2005).
Abdul-Rahman: A. et al., "Dinuclear molybdenum complexes derived from diphenois: electrochemical interactions and reduced species," *Polyhedron* 16(24):4353-4362 (1997).
Acton, S. et al., "Identification of Scavenger Receptor SR-BI as a High Density Lipoprotein Receptor," *Science* 271(5248):516-520 (1996).
Asztalos,B.F ., "High-Density Lipoprotein Metabolism and Progression of Atherosclerosis: New Insights from the HDL Atherosclerosis Treatment Study." *Curr. Opin. Cardiol.* 19:385-391 (2004).
Baba, S. et al., "Continuous intake of polyphenotic compounds containing cocoa powder reduces LDL oxidative susceptibility and has beneficial effects on plasma HDL-cholesterol concentrations in humans," *Am. J. Clin. Nutr.* 85:709-717 (2007).
Badimon, J.J. et al., "Role of High Density Lipoproteins in the Regression of Atherosclerosis," *Circulation* 86(Suppl. III):86-94 (1992).

Bayly, S.R. et al., "Electronic and magnetic metal-metal interactions in dinuclear oxomolybdenum(V) complexes across bis-phenolate bridging ligands with different spacers between the pholate termini: ligand-centered vs. metal-centered redox activity," *J. Chem. Soc., Dalton Transactions* 9:1401-1414 (2001).

Bertelè, V. et al., "Platelet Thromboxane Synthetase Inhibitors with Low Doses of Aspirin: Possible Resolution of the 'Aspirin Dilemma'," *Science* 220:517-519 (1983).

Beugelmans, R. et al., "One-Pot Synthesis of 1-Oxi-1,2-dihydroisoquinolines (Isocarbostyrils) vie SRN1 (Ar) Reactions," *Synthesis* 9:729-731 (1981).

Bhilare. S.V. et al., "Ionic-Liquid-Influenced Expeditious and Stereoselective Synthesis of Olefins," *Synthetic Communications* 37(18):3111-3117 (2007).

Bisagni, E. et al., "A Convenient Way to Dibenzo[c,h]-1,5-Naphthyridines (11-Aza-Benzo[c]phenanthridines)," *Tetrahedron* 52(31):10427-10440 (1996).

Bisgaier, C. et al., "A Novel Compound That Elevates High Density Lipoprotein and Activates the Peroxisome Proliferator Activated Receptor," *J. Lipid Res.* 39:17-30 (1998).

Boyce, W.T. et al., "The Acylation and Alkylation of o-Toluinitrile. A New Route to 3-Substituted Isocarbostyrils," *J. Org. Chem.* 31:3807-3809 (1966).

Bradsher, C.K. et al., "A New Isoquinoline Synthesis via Ortho-Substituted Benzylamines," *Tetrahedron Lett.* 31:3149-3150 (1972).

Bradsher, C.K. et al., "α-Acyl-o-toluinitriles As Intermediates in the Preparation of 3-Substituted Isoquinolines and 1-Amino-2-benzopyrylium Derivatives," *J. Org. Chem.* 43(20):3817-3820 (1978).

Buhle, E.L. et al., "Trivalent carbon. II. Unsymmetrical Hexaaryldimethylperoxides," *J. Am. Chem. Soc.* 65:584-586 (1943).

Cherubini, A. et al., "Role of antioxidants in Atherosclerosis: Epidemiological and Clinical Update," *Curr. Pharm. Des.* 11:2017-2032 (2005).

Cho, W-J. et al., "Molecular Modeling of 3-Arylisoquinoline Antitumor Agents Active Against A-549. A Comparative Molecular Field Analysis Study," *Bioorg. Med. Chem.* 10:2953-2961 (2002).

Cho, W-J. et al., "Synthesis and Biological Evaluation of 3-Arylisoquinolines As Antitumor Agents," *Bioorg. Med. Chem. Lett.* 8:41-46 (1998).

Chyu, K-Y. et al., "Differential Effects of Green Tea-Derived Catechin on Developing Versus Established Atherosclerosis in Apolipoprotein E-Null Mice," *Circulation* 109:2448-2453 (2004).

Clarkson, T.B. et al., "Inhibition of Postmenopausal Atherosclerosis Progression: A Comparison of the Effects of Conjugated Equine Estrogens and Soy Phytoestrogens," *J. Clin. Endocrinol. Metab.* 86(1):41-47 (2001).

Cooper, K.A. et al., "Wine polyphenols and promotion of cardiac health," *Nutr. Res. Rev.* 17:111-129 (2004).

Cramer, R. et al., "New Syntheses of Aryl Fluorides and Aryl Fluorosulfonates from Oxyflourides of Sulfur," *J. Org. Chem.* 26:4164-4165 (1961).

Dai, G. et al., "Synthesis of 3,4-disubstitute Isoquinolines via Palladium-Catalyzed Cross-Coupling of 2-(1-Alkynyl)benzaldimines and Organic Halides," *J. Org. Chem.* 68:920-928 (2003).

Dai, G. et al., "Synthesis of 3-Substituted 4-Aroylisoquinolines via Pd-Catalyzed Carbonylative Cydization of 2-(1-Alkynyl)benzaldimines," *J. Org. Chem.* 67:7042-7047 (2002).

Dansky, H.M. et al., "High-Density Lipoprotein and Plaque Regression: The Good Cholesterol Gets Even Better," *Circulation* 100:1762-1763 (1999).

Decossin, C. et al., "Subclasses of LpA-I in Coronary Artery Disease: Distribution and Cholesteroi Efflux Ability," *Eur. J. Clin. Invest.* 27:299-307 (1997).

Eiden, F. et al., "1,2-Bisbenzopyranylethane" *Archiv der Pharmzie* 313(2):120-128 (1980) (German).

English language Derwent abstract for EP 2005941 A2.
English language Derwent abstract for JP 6-080656.
English language Derwent abstract for JP 7041442.
English language Derwent abstract for JP 761942.
English language Derwent abstract for JP 7118241.
English language Derwent abstract for JP 7179380.
English language Derwent abstract for JP 7233109.
English language Derwent abstract for JP 10287678.
English language Derwent abstract for JP 2002/249483.
English language Derwent abstract for JP 2004/203751.
English language Derwent abstract for JP 2004/307440.

Esterbauer, H. et al., "Continuous Monitoring of In Vitro Oxidation of Human Low Density Lipoprotein," *Free Radical Res. Commun.* 6:67-75 (1989).

Fielding, C.J. et al., "Molecular Physioiogy of Reverse Cholesterol Transport," *J. Lipid Res.* 36:211-226 (1995).

Fieser, L.F., "The potentials of some unstable oxidation-reduction systems" *J. Am. Chem. Soc.* 52:4915-4940 (1930).

Flammang, M. et al., "2,3-Benzodiazepines: 2-Aminoisoquinolinones From Ring Contraction of 1-oxo-2,3-Benzodiazepines," *C R Acad Sci Paris, Series C* 290:361-363 (1980) (French).

Fokialakis, N. et al., "A New Class of Phytoestrogens: Evaluation of the Estrogenic Activity of Deoxybenzoins," *Chem. Biol.* 11:397-406 (2004).

Gidez, L.I. et al., "Separation and Quantitation of Subclasses of Human Plasma High Density Lipoproteins By a Simple Precipitation Procedure," *J Lipid Res* 23:1206-1223 (1982).

Gordon, T. et al., "High Density Lipoprotein As a Protective Factor Against Coronary Heart Disease," *Am. J. Med.* 62(5):707-714 (1977).

Gugler, R. et al., "Disposition of Quercetin in Man after Single Oral and Intravenous Doses," *Eur J Clin Pharmacol* 9:229-234 (1975).

Guillory, J.K. "Generation of Polymorphs, Hydrates, Solvates, and Amorphous Solids" Brittain, Harry G, (ed.) *Polymorphism in Pharmaceutical Solids*, vol. 95: Marcel Dekker, Inc., New York; pp. 202-208 (1999).

Hakamata, H. et al., "Differential effects of an acyl-coenzyme A: cholesterol acyltransferase inhibitor on HDL-induced cholesterol efflux from rat macrophage foam cells," *FEBS Letters* 363:29-32 (1995).

Haneke, K.E. "Trans-Resveratrol [501-36-0]. Review of Toxicological Literature," Nat. Inst. Environ. Health Sciences Contract No. NO1-ES-65402 (Mar. 2002).

Heeg, J.F. et al., "Plasma Levels of Probucol in Man After Single and Repeated Oral Doses," *La Nouvelle Presse Médicale* 9(40):2990-2994 (1980) (French), Abstract p. 2990.

Hemingway, R.W. et al., "A gas-liquid chromatographic examination of stilbene derivatives," *J. Chromatography* 50(3):391-399 (1970).

Hidaka, H. et al., "Affinity purification of the hepatic high-density lipoprotein receptor identifies two acidic glycoproteins and enables further characterization of their binding properties," *Biochem. J.* 284:161-167 (1992).

Hirano, K-i. et al., "Genetic Chotesteryl Ester Transfer Protein Deficiency Is Extremely Frequent in the Omagari Area of Japan, Marked Hyperalphalipoproteinemia Caused by CETP Gene Mutation Is Not Associated With Longevity," *Arterioscler. Thromb. Vas. Biol.* 17:1053-1059 (1997).

Huang, Q. et al., "Synthesis of isoquinolines by palladium-catalyzed cyclization, followed by a Heck reaction," *Tetrahedron Lett.* 43:3557-3560 (2002).

Hwang, J. et al, "Syntergistic inhibition of LDL oxidation by phytoestrogens and ascorbic acid" *Free Radical Biology and Medicine* 29(1):79-89 (Jul. 1, 2000).

International Search Report and Written Opinion issued in International Application No. PCT/CA2004/001818 mailed on Feb. 28, 2005.

Ishibashi, S. et al., "Hypercholesterolemia in Low Density Lipoprotein Receptor Knockout Mice and its Reversal by Adenovirus-Mediated Gene Delivery," *J. Clin. Invest.* 92:883-893 (1993).

Ishibashi, S. et al., "Massive Xanthomatosis and Atherosclerosis in Cholesterol-led Low Density Lipoprotein Receptor-Negative Mice," *J. Clin. Invest.* 93:1885-1893 (1994).

Jayatilake, G.S. et al., "Kinase Inhibitors From *Polygonum cuspidatum*," *J. Nat. Prod.* 56(20):1805-1810 (Oct. 1993).

Kilbourne, E.J. et al., "Involvement of Early Growth Response Factor Egr-1 in Apolipoprotein AI Gene Transcription," *J. Biol. Chem.* 270:7004-7010 (Mar. 24, 1995).

Kim, E-K. et al., "Hypothetical Drug Binding Receptor Site Analysis Using CoMFA Method for 3-Arylisoquinolines Active Against SK-OV-3 Tumor Cell Line," *Yakhak Hoechi* 46(4):219-225 (2002).

Kulkarni, K.R. et al., "Quantification of $HDL_2$ and $HDL_3$ Cholesterol By the Verticai Auto Profile-II (VAP-II) Methodology," *J. Lipid Res.* 38:2353-2364 (1997).

Kurata, H. et al., "A Candidate High Density Lipoprotein (HDL) Receptor, $HB_2$, with Possible Multiple Functions Shows Sequence Homology with Adhesion Molecules," *J. Atheroscler. Thromb.* 4(3):112-117 (1998).

Kurowska, E.M., "Essential Amino Acids in Relation to Hypercholesterolemia Induced in Rabbits by Dietary Casein," *J. Nutr.* 120:831-836 (1990).

Kuzuyza, M. et al., "Probucol Prevents Oxidative Injury to Endothelial Cells," *J. Lipid Res.* 32:197-204 (1991).

Laarhoven, W.H. et al., "Syntheses, infrared spectra, and molecular refractions of some sterically hindered p,p'-dimethoxystilbenes. Influence of non-planarity in styrene and stilbene derivatives IV," *Recueil des Travaux Chimiques des Pays-Bas* 80:775-791 (1961).

Lagrost, L. et al., "Opposite Effects of Cholesteryl Ester Transfer Protein and Phospholipid Transfer Protein on the Size Distribution of Plasma High Density Lipoproteins," *J. Biol. Chem.* 271(32):19058-19065 (Aug. 9, 1996).

Landshulz, K.T. et al., "Regulation of Scavenger Receptor, Class B, Type I, a High Density Lipoprotein Receptor, in Liver and Steroidogenic Tissues of the Rat," *J. Clin. Invest.* 98(4):984-995 (Aug. 1996).

Lin, C-F. et al., "Solvent Effects on Aza-anionic Cycloaromatization of 2-(2-Substituted-ethynyl)benzonitriles," *J. Chinese Chem. Soc.* 48:211-214 (2001).

Lin, J. et al., "The Role of Absorption, Distribution, Metabolism, Excretion and Toxicity in Drug Recovery," *Curr. Top. Med. Chem.* 3:1125-1154 (2003).

Lin, J-K. et al., "Chemoprevention of Cancer and Cardiovascular Disease by Resveratrol," *Proc. Natl. Sci. Counc. ROC(B)* 23(3):99-106 (1999).

Linnell, W.H., "Isomers of stilbestrol. Part II," *Q. J. Pharm. Pharmacol.* 15:384-388 (1942).

López, S.E. et al., "The synthesis of substituted 2-aryl-4(3H)-quinazolinones using $NaHSO_3$/DMA. Steric effect upon the cyclisation-dehydrogenation step," *J. Chem. Research (S)* pp. 258-259 (2000).

Maher, V.M.G. et al., "Lipoprotein (a) and coronary heart disease," *Curr. Opin. Lipidol.* 6:229-235 (1995).

Mahto, R.P. et al., "Synthesis of 3-Aryl-7-Hydroxy lsochromenes" *Asian J. Chem.* 11(2):431-435 (1999).

Marks, F. "Epidermal Growth Control Mechanisms, Hyperplasia, and Tumor Promotion in the Skin," *Cancer Res.* 36:2636-2343 (Jul. 1976).

McKee, R.L. et al., "Some Basically Substituted Quinazolines." *J. Am. Chem. Soc.* 68(10):1902-1903 (1946).

Melani, F. et al., "Tricyclic heterocyclic systems: pyrazolo[5',4':4,5]- and pyrazolo-[3',4'.4.5]pyrano[2,3-B]pyridine derivatives," *J. Heterocyclic Chem.* 25:1367 (Sep.-Oct. 1988).

Mondal, S. et al., "Two-Stage Chemical Oncogenesis in Cultures of C3H/10T1/2 Cells," *Cancer Res.* 38:2254-2260 (Jul. 1976).

Nourooz-Zadeh, J. "Ferrous Ion Oxidation in Presence of Xylenol Orange for Detection of Lipid Hydroperoxides in Plasma," *Methods Enzymol.* 300:58-62 (1999).

Office Action in U.S. Appl. No. 11/255,103, mailed Sep. 24, 2008.
Office Action in U.S. Appl. No. 11/255,103, mailed Aug. 31, 2009.
Office Action in U.S. Appl. No. 11/254,420, mailed Aug. 5, 2008.
Office Action in U.S. Appl. No. 11/254,420, mailed Mar. 3, 2009.

Ohtomo, T. et al., "Comparative activities of daidzein metabolites, equol and O-desmethylangolensin, on bone mineral density and lipid metabolism in ovariectomixed mice and in osteoclast cell cultures," *Eur. J. Nutr.* 47(5):273-279 (2008).

Ordovas, J.M. "Gene-diet interaction and plasma lipid responses to dietary intervention," *Biochem. Soc. Trans.* 30(2):68-73 (2002).

Parra, H.J. et al., "A Case-Control Study of Lipoprotein Particles in Two Populations at Contrasting Risk for Coronary Heart Disease," *Arterioscler. Thromb.* 12:701-707 (1992).

Pearson, D.E. et al., "The *ortho* Bromination of Phenols," *J. Org. Chem.* 32:2358-2360 (1967).

Pettit, G.R. et al., "Antineoplastic Agents. 465. Structural Modification of Resveratrol: Sodium Resverastatin Phosphate," *J. Med. Chem.* 45:2534-2542 (2002).

Quiñones, A. et al., "The *egr*-1 gene is induced by DNA-damaging agents and non-genotoxic drugs in both normal and neoplastic human cells," *Life Sciences* 72(26):2975-2992 (2003).

Ragione, F.D. et al., "Antioxidants induce different phenotypes by a distinct modulation of signal transduction," *FEBS Letters* 523:289-294 (2002).

Ragione, F.D. et al., "$p21^{Cip1}$ Gene Expression Is Modulated by Egr1: A Novel Regulatory Mechanism Involved in the Resveratrol Antiproliferative Effect," *J. Biol. Chem.* 278(26):23360-23368 (2003).

Rajakumar, P. et al., "$TiCl_4$-Dioxane—A Facile and Efficient System for De-O-Benzylation, De-O-Allylation, and De-O-Xylylation of Phenolic Ethers," *Synthetic Communications* 33(22):3891-3896 (2003).

Rice-Evans, C. "Serial Review: Flavonoids and Isoflavones (Phytoestrogens): Absorption, Metabolism, and Bioactivity," *Free Radical Biol. Med.* 36(7):827-828 (2004).

Richtzenhain, H. "Estrogenic stilbene and diphenylethane derivatives. II," *Chemische Berichte* 82:405-407 (1949) (German).

Rigotti, A. et al., "Regulation by Adrenocorticotropic Hormone of the in Vivo Expression of Scavenger Receptor Class B Type I (SR-BI), a High Density Lipoprotein Receptor, in Steroidogenic Cells of the Murine Adrenal Gland," *J. Biol. Chem.* 271(52):33545-33549 (1996).

Rodriguez, A. et al., "Novel Effects of the Acyl-Coenzyme A: Cholesterol Acyltransferase Inhibitor 58-035 on Foam Cell Development in Primary Human Monocyte-Derived Macrophages," *Arterioscler. Thromb. Vasc. Biol.* 19:2199-2206 (1999).

Rubin, E.M. et al., "Expression of Human Apolipoprotein A-1 in Transgenic Mice Results in Reduced Plasma Levels of Murine Apolipoprotein A-1 and the Appearance of Two New High Density Lipoprotein Size Subclasses," *Proc. Natl. Acad. Sci. USA* 88:434-438 (Jan. 1991).

Rubin, E.M. et al., "Inhibition of Early Atherogenesis in Transgenic Mice by Human Apolipoprotein AI," *Nature* 353:265-267 (Sep. 19, 1991).

Sarkhel, B.K. et al., "3-Arylisocoumarin: Synthesis of 3-(4-Methoxyphenyl)-isocoumarin," *J. Indian Chem. Soc.* 53:915-916 (Sep. 1976).

Schiess, P. et al., "Thermolytic Ring Opening of Acyloxybenzocyclobutenes: An Efficient Route to 3-Substitute Isoquinolines," *Tetrahedron Lett.* 26(33):3959-3962 (1985).

Schork, N., "Genetics of Complex Disease," *Am. J. Respir. Crit. Care Med.* 156(4):S103-109 (Oct. 1997)(printed pp. 1-19).

Schultz, T.P. et al., "Role of stilbenes in the natural durability of wood: fungicidal structure-activity relationships" *Phytochemistry* 29(5):1501-1507 (1990).

Shapiro, D.J. et al., "Micro Assay for 3-Hydroxy-3-Methylglutaryl-CoA Reductase in Rat Liver and L-Cell Fibroblasts," *Biochem. Biophys. Acta* 370:369-377 (1974).

Sieber, R.H. "Reactions of chloroacetaldehyde with aromatic hydrocarbons, phenols, and phenol ethers" *Justus Liebigs Annalen der Chemie* 730:31-46 (1969) (German), Abstract p. 31.

Sliwa, H. et al. "Tautomérie entre structures α-énaminocétone et β-céto iminoéther présentée par les pipéridéines résultant de la semihydrogénation d'alcoxy-2-acyl-3 pyridines" *J. Heterocyclic Chem.* 16:969 (1979) (French), Abstract.

Slowing, K. et al., "Anti-Inflammatory Activity of Leaf Extracts of *Eugenia jambos* in Rats," *J. Ethnopharmacol.* 43:9-11 (1994).

Smyth, M.S. et al., "Non-amine based analogs of Lavendustin A as protein-tyrosine kinase inhibitors," *J. Med. Chem.* 36(20):3010-3014 (1993).

Sun, D. et al., "In Vitro Testing of Drug Absorption for Drug 'Developability' Assessment: Forming an Interface Between in Vitro Preclinical Data and Clinical Outcome," *Curr. Opin. Drug Discov. Devel.* 7(1):75-85 (2004).

Suryadevara, V. et al., "Association of Abnormal Serum Liquids in Elderly Persons with Artherosclerotic Vascular Disease and Demetia. Artheroslerotic Vascular Disease Without Demetia, Demetia Without Artherosclerotic Vascular Disease, and No Dementia or Artherosclerotic Vascular Disease," *J. Gerontol. Med. Sci.* 58A(9):859-861 (2003).

Tait, A. et al., "Synthesis and Free Radical Scavenging Activity of 4-(2H-1,2,4-Benzothiadiazine-1,1-dioxide-3-yl)-2,6-bis(1,1-dimethylethyl)phenols," *Tetrahedron* 52(38):12587-12596 (1996).

Talbert, R.L. "Current Recommendations for the Treatment of Dyslipidemia," *Pharm. Ther.* 29(2):104 (Feb. 2004).

Tardiff, J-C. et al., "Probucol and Multivitamins in the Prevention of Restenosis After Coronary Angioplasty," *N. Engl. J. Med.* 337(6):365-367 (Aug. 7, 1997).

Toth, P.P. et al., "Therapeutic Interventions Targeted At the Augmentation of Reserve Cholesterol Transport," *Curr. Opin. Cardiol.* 19:374-379 (2004).

Tovar, J.D. et al., "Pyrylium Salts Via Electrophilic Cyclization: Applications for Novel 3-Arylisoquinoline Syntheses," *J. Org. Chem.* 64:6499-6504 (1999).

Tudan, C. et al., "Selective Inhibition of Protein Kinase C, Mitogen-Activated Protein Kinase, and Neutrophil Activation in Response to Calcium Pyrophosphate Dihydrate Crystals, Formyl-Methionyl-Leucyl-Phenylalanine, and Phorbol Ester by O-(Chloroacetyl-carbamoyl) Fumagillol (AGM-01470; TNP-470)," *Biochem. Pharmacol.* 58:1869-1880 (1999).

U.S. Appl. No. 10/575,406, filed Nov. 1, 2006, Inventors: Norman C.W. Wong et al.

U.S. Appl. No. 11/670,238, filed Feb. 1, 2007, Inventors: Norman C.W. Wong et al.

Utermann, G. "The Mysteries of Lipoprotein(a)," *Science* 246:904-910 (1999).

Varin, L. et al., "Enzymatic Assay for Flavonoid Sulfotransferase," *Anal. Biochem.* 161:176-180 (1987).

Vippagunta, S.R. et al., "Crystalline solids" *Adv. Drug Delivery Rev.* 48:3-26 (2001).

Webster Ninth New Collegiate Dictionary, Definition of 'Prevent', 1 page (2000).

Yamakoshi, J. et al., "Isoflavone Aglycone-Rich Extract without Soy Protein Attenuates Atherosclerosis Development in Cholesterol-Fed Rabbits," *J. Nutr.* 130(8):1887-1893 (2000).

Yoshioka, N. et al., "Semiempirical Investigation of Stilbene-Linked Diradicals and Magnetic Study of Their Bis(*N-tert*-butylnitroxide) Variants," *J. Org. Chem.* 59(15):4272-4280 (1994).

Lopez et al., "The Synthesis of Substituted 2-Aryl-4(3H)-quinazolinones using NaHSO3/DMA. Steric Effect Upon the Cyclisation-Dehydrogenation Step" J. Chem. Research (S) pp. 258-259 (2000).

Office Action in pending U.S. Appl. No. 11/254,420 mailed Sep. 28, 2009.

Office Action in pending U.S. Appl. No. 11/254,420 mailed Feb. 2, 2010.

Notice of Allowance in pending U.S. Appl. No. 11/254,420 mailed Jul. 26, 2010.

Office Action in pending U.S. Appl. No. 11/255,103 mailed Mar. 31, 2010.

Office Action in U.S. Appl. No. 11/255,103: Restriction Requirement, mailed Mar. 26, 2008.

Office Action in U.S. Appl. No. 11/255,103, mailed Nov. 10, 2010.

Notice of Allowance in U.S. Appl. No. 11/255,103, mailed Jun. 7, 2011.

Office Action in U.S. Appl. No. 11/670,238: Restriction Requirement, mailed Jul. 20, 2010.

Office Action in U.S. Appl. No. 11/670,238: Restriction Requirement, mailed Mar. 31, 2010.

Office Action in U.S. Appl. No. 11/670,238, mailed Oct. 7, 2010.

Office Action in U.S. Appl. No. 11/670,238, mailed Apr. 19, 2011.

Office Action in U.S. Appl. No. 11/670,238, mailed Jun. 22, 2011.

Office Action in U.S. Appl. No. 11/670,238: Notice of Allowance, mailed Aug. 3, 2011.

Edwards et al., "Inhibition of myeloperoxidase release from rat polymorphonuclear leukocytes by a series of azachalcone derivatives" *J. Med. Chem.* 37(25):4357-4362 (1994).

International Search Report and Written Opinion issued in International Application No. PCT/IB2010/000826; Date of Mailing: Oct. 12, 2010.

International Search Report and Written Opinion issued in International Application No. PCT/IB2010/031870; Date of Mailing: Jul. 1, 2010.

Letan, "The Relation of Structure to Antioxidant Activity of Quercetin and some of Its Derivatives. I. Primary Activity" *J. Food Sci.* 13(4):518-523 (1966).

Moffett, "Azacoumarins" *J. Org. Chem.* 35(11):3596-3600 (1970).

Nigam et al., "Synthesis and Pharmacological Screening of Some New 2-(Phenyl/Chloromethyl)-3-[4 (N, N-Disubstituted Aminocarbonyl) Phenyl]-8-Substituted-4(3H)-Quinazolones" *Indian Drugs* 27(4):238-243 (1990).

Office Action in U.S. Appl. No. 11/255,103: Notice of Allowance, mailed Sep. 15, 2011.

Office Action in U.S. Appl. No. 11/670,238: Notice of Allowance, mailed Sep. 16, 2011.

Office Action in U.S. Appl. No. 12/369,296, mailed Nov. 10, 2011.

Office Action in U.S. Appl. No. 12/369,296, mailed Mar. 13, 2012.

Office Action in U.S. Appl. No. 12/369,296: 2012 Notice of Allowance, mailed Apr. 12, 2012.

Office Action in U.S. Appl. No. 12/490,877, mailed Sep. 15, 2011.

Office Action in U.S. Appl. No. 12/490,877: Notice of Allowance, mailed Nov. 25, 2011.

Office Action in U.S. Appl. No. 12/905,500, mailed Nov. 25, 2011.

Office Action in U.S. Appl. No. 12/905,500: Notice of Allowance, mailed Apr. 11, 2012

Japanese Patent Application No. 2008-524272: Notice of Reasons for Rejection, mailed Jul. 24, 2012, with English translation.

* cited by examiner

PHARMACEUTICAL COMPOSITIONS FOR THE PREVENTION AND TREATMENT OF COMPLEX DISEASES AND THEIR DELIVERY BY INSERTABLE MEDICAL DEVICES

CROSS-REFERENCE TO RELATED APPLICATIONS

This is a national stage application, based on PCT Application No. PCT/US2006/029827 filed on Jul. 28, 2006, and claims the benefit of priority to U.S. Application No. 60/704,035, filed on Jul. 29, 2005, which is incorporated herein by reference.

TECHNICAL FIELD

The present invention relates to polyphenol-like compounds that are useful for inhibiting VCAM-1 expression, MCP-1 expression and/or SMC proliferation in a mammal. The disclosed compounds are useful for regulating markers of inflammatory conditions, including vascular inflammation, and for treatment and prevention of inflammatory and cardiovascular diseases.

BACKGROUND

Atherosclerosis, restenosis and immune disorders, such as arthritis, are viewed as inflammatory conditions mediated in large part by an inflammatory cascade. For instance, the pathogenesis of atherosclerosis or restenosis occurs in three phases; an inflammatory phase, a cellular proliferative phase, and a phase of remodeling involving extracellular matrix protein synthesis. The inflammatory phase is initiated by expression and exhibition of inflammatory molecules (such as VCAM-1, ICAM-1, or E-selectin) on endothelial cells, resulting in the recruitment of monocytes from the bloodstream into the sub-endothelial space. When in the endothelium, monocytes transform into macrophages and become foam cells as they take up cholesterol. These cholesterol-loaded foam cells release cytokines such as monocyte-colony stimulating factor and monocyte chemoattractant protein-1 (MCP-1), instigating the cellular proliferative phase. Cytokine secretion results in localized monocyte and smooth muscle cell (SMC) proliferation and recruitment and production of extracellular matrix (the final phase). During this phase macrophages continue their uptake of cholesterol in the form of oxidized low-density lipoprotein resulting in swelling of the artery wall. Continuance of this inflammatory cascade eventually results in the formation of a plaque consisting of lipid-engorged macrophage-foam cells, smooth muscle cells, and extracellular matrix (Crowther M (2005) *Hematology* 1, 436).

Expression of vascular adhesion molecule-1 (VCAM-1) on the surface of endothelial cells for the adhesion and transmigration of monocytes is a fundamental early event in a wide variety of inflammatory conditions: such as autoimmune disorders, bacterial and viral infections, asthma, rheumatoid arthritis, and autoimmune diabetes, in addition to atherosclerosis (Pilewski J M et al. (1995) *Am J Respir Cell Mol Biol* 12, 1; Ohkawara Y et al. (1995) *Am J Respir Cell Mol Biol* 12, 4; Rabb A et al. (1994) *Am J Respir Care Med* 11, 149). Thus, drugs that inhibit VCAM-1 expression are desirable therapeutics for the treatment of these conditions.

Chemoattractant factors, such as MCP-1, have been shown to play a role in monocyte recruitment, proliferation, and migration in a number of inflammatory conditions and are correlated with a risk for restenosis (Welt F G P et al. (2002) *Arterioscler Thromb Vasc Biol.* 22, 1769). As such, inhibition of MCP-1 expression represents a desirable property of anti-inflammatory therapeutics. Finally, smooth muscle cell hyperplasia, resulting in tissue remodeling and decreased organ function is another characteristic of many inflammatory conditions including atherosclerosis, restenosis, chronic transplant rejection, and asthma. Therefore, inhibition of the hyperproliferation of SMC is another desirable property for therapeutic compounds.

To date the most effective means of preventing and treating atherosclerosis has been via cholesterol-dependant approaches. These include seeking to lower low-density lipoprotein or raise high density lipoprotein cholesterol. For example, one method provides compounds useful for regulating the expression of ApolipoproteinA-I (ApoA-I) (PCT/US2005/038048) a lipoprotein important for transporting cholesterol.

However, the identification of new inflammatory mediators in the early pathogenesis of atherosclerosis and restenosis has led to a new focus on a variety of inflammatory or cholesterol-independent approaches; including the inhibition of VCAM-1 and MCP-1 expression, or prevention of smooth muscle cell (SMC) proliferation. Increasing evidence from epidemiological, clinical, and basic mechanistic studies supports the importance of these inflammatory targets in the treatment and prevention of inflammatory conditions. Finding drugs that inhibit VCAM-1 and/or MCP-1 expression, or inhibit smooth muscle cell proliferation is desirable.

One class of such compounds thought to play a role in the prevention of inflammatory conditions are polyphenols. These are common constituents in of the human diet; they are present in many foods and beverages of plant origin. Numerous patents and applications describe uses, compositions, and methods for the prevention, treatment or mitigation of inflammatory and cardiovascular diseases by the administration of naturally occurring polyphenols to a patient in need of a pharmaceutical intervention (see, e.g., U.S. Ser. Nos. 03/033,578, 10/696,752, US 2004 0105817, U.S. Pat. Nos. 6,900,241, 6,649,193, US 2002 029088, US 2003 065505, PCT/09901997/IB, PCT/00000392/AU, PCT/00235153/US, PCT/US1996/04,028, US 2005 0171163 A1).

It is believed that polyphenols are effective, at least in part, as a result of their activity on the inhibition of VCAM-1, MCP-1, LDL oxidation, and smooth muscle cell proliferation (Takahahi. R et al., (2005) *J Agric Food Chem* 53, 1; Fuhrman B et al. (2005) *J Nutr* 135, 722; Cald U P et al. (1996) *Am J Clin Nutr* 63, 403; Tijburg L B et al. (1997) *Crit. Rev Food Sci Nutr* 37, 771; Leiro J et al. (2004) *Int Immunopharmacol* 4, 991; Carluccio M A et al., (2003) *Arterioscler Thromb Vasc* 23, 622; Ouyang P et al. (2004) *Di Yi Jun Yi Da Xue Xue Bao* 24, 975; Hofmann C S et al. (2003) *FASEB J* 17, 702; Araim O et al. (2002) *J Vasc. Surg* 35, 1226; El Bedout J et al., (2005) *Cardiovasc Res* 67, 317). The inverse relationship between dietary polyphenol consumption and incidence of cardiovascular diseases is likely associated with their ability to attenuate biomarkers of oxidative stress, lipidemia and inflammation. Consequently, naturally occurring polyphenols have the potential to be therapeutically employed.

However, the protective properties of naturally occurring polyphenols have been difficult to realize for several reasons, including poor bioavailability and deleterious effects at, high concentrations. For instance, the most abundant and available source of resveratrol for consumers, red wine, cannot be consumed in therapeutically efficacious quantities on a daily basis because of the deleterious effects of excessive alcohol consumption. Furthermore, the use of naturally occurring polyphenols as potential therapies has also been impeded by an inability to achieve efficacious levels because of poor bioavailability. Bioavailability of polyphenols in humans ranges from 1% to 26% with variability between individuals, and between different polyphenols. In addition to this, polyphenols differ in how they are absorbed, metabolized, and excreted. For example, polyphenol flavonoids, such as quercetin, have been reported to have less than 1% intestinal absorption following oral administration (Gugler et al. (1975) *Eur J Clin Pharm* 9, 223). Another complicating factor is the effect of metabolites of polyphenols. These have been shown to have a negative influence on the biological activity of the parent compounds. Such metabolites often differ from the parent compound in terms of toxicity, efficacy, and length of residence in the plasma. These and other limiting factors, such as poor water solubility limiting the route of administration, have made it difficult to determine appropriate dosages for use in humans.

Additionally, several human studies on foods or beverages containing polyphenols have failed to demonstrate any significant benefit on primary clinical endpoints, such as oxidative stress, lipidemia, and inflammation. Of twelve recent studies examining differing sources of polyphenols; six showed no effect on lipid parameters while the other six showed some improvement (Manach (2005) *Curr Opin Lipidol* 16, 77-84). Such contradictory data has limited the use of polyphenols, despite their many potentially beneficial properties.

Thus, there continues to be a need for novel compounds with properties like those of polyphenols for the prevention and treatment of inflammatory conditions. Embodiments of the present invention include compounds that inhibit VCAM-1 and/or MCP-1 expression and/or inhibit smooth muscle cell proliferation. The compounds of the present invention also possess other properties, which enable their use in the treatment or prophylaxis of other diseases and conditions.

SUMMARY

The methods of invention include administering to a mammal (e.g., a human) in need thereof a therapeutically effective amount of a compound of Formula 1:

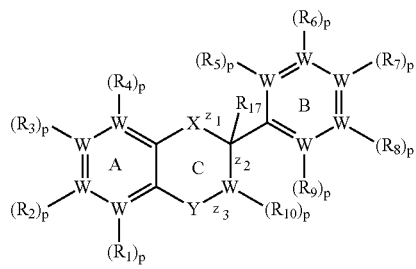

Formula 1 wherein:
X is selected from $CR_{11}$, $CR_{11}R_{13}$, CO, CS, O, S, SO, $SO_2$, N and $NR_{11}$, wherein $R_{11}$ may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl, bicyclic heteroaryl or bicyclic heterocyclyl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if at least one W is not N, then
a) X and Y are each CO,
b) X is $NR_{11}$ and $Z_2$ is a double bond, or
c) two adjacent substituents selected from $R_5$, $R_6$, $R_7$, $R_8$, and $R_9$ are connected in a 5 or 6-membered ring to form a bicyclic aryl, bicyclic heteroaryl or bicyclic heterocyclyl;
and pharmaceutically acceptable salts and hydrates thereof.

One embodiment provides methods and compositions useful for inhibiting VCAM-1 expression, MCP-1 expression and/or SMC proliferation in a mammal.

In certain embodiments, the methods and compositions of the invention are useful for treating, preventing or mitigating inflammatory conditions and related disease states, characterized by altered expression of markers of inflammation such as VCAM-1, MCP-1 and/or SMC proliferation.

One embodiment provides a compound of Formula 1:

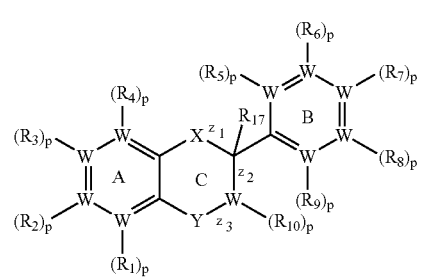

Formula 1 wherein:
X is selected from $CR_{11}$, CO, N, $NR_{11}$ and O;
Y is selected from $CR_{12}$, CO, and $NR_{12}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, alkyl, amino, aminoalkoxy, aminoalkyl, carboxyalkoxy, halogen, heterocyclyl, heterocyclylalkoxy, heterocyclylalkyl, hydrogen, hydroxyalkoxy, hydroxyalkyl, and hydroxyl, or
two adjacent substituents selected from $R_5$, $R_6$, $R_7$, $R_8$ and $R_9$ are connected in a 5 or 6-membered ring to form a bicyclic aryl, bicyclic heteroaryl or bicyclic heterocyclyl;
each W is independently selected from C and N, wherein if W is N, then p is 0 and if W is C, then p is 1;
$Z_1$, $Z_2$ and $Z_3$ are each independently selected from a single bond and a double bond;
wherein if at least one W is not N, then
a) X and Y are each CO, or
b) X is $NR_{11}$ and $Z_2$ is a double bond;
and pharmaceutically acceptable salts and hydrates thereof.

DETAILED DESCRIPTION

Definitions

The term "aldehyde" or "formyl" as used herein refers to the radical —CHO.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as ($C_2$-$C_{22}$) alkenyl, ($C_2$-$C_8$)alkenyl, and ($C_2$-$C_6$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group-attached to an oxygen (—O-alkyl-). "Alkoxy" groups also include an alkenyl group attached to an oxygen ("alkenoxy") or an alkynyl group attached to an oxygen ("alkynoxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, and ($C_1$-$C_6$)alkoxy, respectively. Exemplary alkoxy groups include, but are not limited to methoxy, ethoxy, etc.

The term "alkyl" as used herein refers to a saturated straight or branched hydrocarbon, such as a straight or branched group of 1-22, 1-8, or 1-6 carbon atoms, referred to herein as ($C_1$-$C_{22}$)alkyl, ($C_1$-$C_8$)alkyl, and ($C_1$-$C_6$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as ($C_2$-$C_{22}$) alkynyl, ($C_2$-$C_8$)alkynyl, and ($C_2$-$C_6$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" as used herein refers to a radical of the form —$R_aC(O)N(R_b)$—, —$R_aC(O)N(R_b)R_c$—, or —C(O)N$R_bR_c$, wherein $R_b$ and $R_c$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "amide" encompasses groups such as sulfonamide, urea, carbamate, carbamic acid, and cyclic versions thereof. The term "amide" also encompasses an amide group attached to a carboxy group, e.g., -amide-COOH or salts such as -amide-COONa, etc, an amino group attached to a carboxy group, e.g., -amino-COOH or salts such as -amino-COONa, etc.

The term "amine" or "amino" as used herein refers to a radical of the form —$NR_dR_e$, —$N(R_d)R_e$—, or —$R_eN(R_d)$$R_f$— where $R_d$, $R_e$, and $R_f$ are independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. The amino can be attached to the parent molecular group through the nitrogen, $R_d$, $R_e$ or $R_f$. The amino also may be cyclic, for example any two of $R_a$, $R_b$, and $R_c$ may be joined together or with the N to form a 3- to 12-membered ring, e.g., morpholino or piperidinyl. The term amino also includes the corresponding quaternary ammonium salt of any amino group, e.g., —[$N(R_d)(R_e)(R_f)$]$^+$. Exemplary amino groups include aminoalkyl groups, wherein at least one of $R_d$, $R_e$, or $R_f$ is an alkyl group.

The term "aminoalkoxy" as used herein refers to an amino group attached to an alkoxy group.

The term "aminoalkyl" as used herein refers to an amino group attached to an alkyl group.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this invention can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$) aryl."

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms, referred to herein as "($C_6$) arylalkyl."

The term "aryloxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "benzyl" as used herein refers to the group —CH$_2$-phenyl.

The term "bicyclic aryl" as used herein refers to an aryl group fused to another aromatic or non-aromatic carbocyclic or heterocyclic ring. Exemplary bicyclic aryl groups include, but are not limited to, naphthyl or partly reduced forms thereof, such as di-, tetra-, or hexahydronaphthyl.

The term "bicyclic heteroaryl" as used herein refers to a heteroaryl group fused to another aromatic or non-aromatic carbocylic or heterocyclic ring. Exemplary bicyclic heteroaryls include, but are not limited to, 5.6 or 6.6-fused systems wherein one or both rings contain heteroatoms. The term "bicyclic heteroaryl" also encompasses reduced or partly reduced forms of fused aromatic system wherein one or both rings contain ring heteroatoms. The ring system may contain up to three heteroatom's, independently selected from oxygen, nitrogen, or sulfur. The bicyclic system may be optionally substituted with one or more groups selected from alkoxy, aryloxy, alkyl, alkenyl, alkynyl, amide, amino, aryl, arylalkyl, carbamate, carboxyl, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary bicyclic heteroaryls include, but are not limited to, quinazolinyl, benzothiophenyl, benzoxazolyl, benzimidazolyl, benzothiazolyl, benzofuranyl, indolyl, quinolinyl, isoquinolinyl, phthalazinyl, benzotriazolyl, benzopyridinyl, and benzofuranyl.

The term "carbamate" as used herein refers to a radical of the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Exemplary carbamates include, but are not limited to, arylcarbamates or heteroaryl carbamates, e.g. wherein at least one of $R_g$, $R_h$ and $R_i$ are independently selected from aryl or heteroaryl, such as pyridine, pyridazine, pyrimidine, and pyrazine.

The term "carbonyl" as used herein refers to the radical —C(O)—.

The term "carboxy" as used herein refers to the radical —COOH or its corresponding salts, e.g. —COONa, etc. The term carboxy also includes "carboxycarbonyl," e.g. a carboxy group attached to a carbonyl group, e.g., —C(O)—COOH or salts such as —C(O)—COONa, etc.

The term "carboxyalkoxy" as used herein refers to the radical —COOH or its corresponding salts, e.g. —COONa, etc., attached to an alkoxy group.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides, etc., for example, succinic anhydride, succinimide, etc.

The term "ester" refers to a radical having the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, formyl, haloalkyl, halogen, heteroaryl, heterocyclyl, ketone, phosphate, sulfide, sulfinyl, sulfonyl, sulfonic acid and thioketone. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as -alkyl-C(O)—O—, —C(O)—O-alkyl-, -alkyl-C(O)—O-alkyl-, etc. Exemplary esters also include aryl or heteoraryl esters, e.g. wherein at least one of $R_j$ or —$R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term "ether" refers to a radical having the structure —$R_l$O—$R_m$—, where $R_l$ and $R_m$ can independently be alkyl, alkenyl, alkynyl, aryl, cycloalkyl, heterocyclyl, or ether. The ether can be attached to the parent molecular group through $R_l$ or $R_m$. Exemplary ethers include, but are not limited to, alkoxyalkyl and alkoxyaryl groups. Ethers also includes polyethers, e.g., where one or both of $R_l$ and $R_m$ are ethers.

The terms "halo" or "halogen" or "Hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1 to 3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The term "heterocyclylalkyl" as used herein refers to a heterocyclyl attached to an alkyl group.

The term "heterocyclylalkoxy" as used herein refers to a heterocyclyl attached to an alkoxy group.

The terms "hydroxy" and "hydroxyl" as used herein refers to the radical —OH.

The term "hydroxyalkoxy" as used herein refers to a hydroxy radical attached to an alkoxy group.

The term "hydroxyalkyl" as used herein refers to a hydroxy radical attached to an alkyl group.

The term "hydroxyaryl" as used herein refers to a hydroxy radical attached to an aryl group.

The term "ketone" as used herein refers to a radical having the structure —C(O)—Rn (such as acetyl, —C(O)CH$_3$) or —R$_n$—C(O)—R$_o$—. The ketone can be attached to another group through R$_n$ or R$_o$. R$_n$ or R$_o$ can be alkyl, alkenyl, alkynyl, cycloalkyl, heterocyclyl or aryl, or R$_n$ or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to the radical —NO$_2$.

The term "perfluoroalkoxy" as used herein refers to an alkoxy group in which all of the hydrogen atoms have been replaced by fluorine atoms.

The term "perfluoroalkyl" as used herein refers to an alkyl group in which all of the hydrogen atoms have been replaced by fluorine atoms. Exemplary perfluoroalkyl groups include, but are not limited to, C$_{1-5}$ perfluoroalkyl, such as trifluoromethyl, etc.

The term "perfluorocycloalkyl" as used herein refers to a cycloalkyl group in which all of the hydrogen atoms have been replaced by fluorine atoms.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone.

The term "phosphate" as used herein refers to a radical having the structure —OP(O)O$_2$—, —R$_x$OP(O)O$_2$—, —OP(O)O$_2$R$_y$—, or —R$_x$OP(O)O$_2$R$_y$—, wherein R$_x$ and R$_y$ can be alkyl, alkenyl, alkynyl, alkoxy, amide, amino, aryl, aryloxy, carboxy, cyano, cycloalkyl, ester, ether, halogen, heterocyclyl, hydrogen, hydroxy, ketone, nitro, sulfonate, sulfonyl, and thio.

The term "sulfide" as used herein refers to the radical having the structure R$_z$S—, where R$_z$ can be alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom.

The term "sulfinyl" as used herein refers to a radical having the structure —S(O)O—, —R$_p$S(O)O—, —R$_p$S(O)OR$_q$—, or —S(O)OR$_q$—, wherein R$_p$ and R$_s$ can be alkoxy, aryloxy, alkyl, alkenyl, alkynyl, amide, amino, aryl, arylalkyl, cycloalkyl, ester, ether, formyl, halogen, haloalkyl, heteroaryl, heterocyclyl, hydroxyl, ketone, nitro, phosphate, sulfide, sulfonyl, sulfonic acid, sulfonamide and thioketone. Exemplary sulfinyl groups include, but are not limited to, alkylsulfinyls wherein at least one of R$_p$ or R$_q$ is alkyl, alkenyl or alkynyl.

The term "sulfonamide" as used herein refers to a radical having the structure —(R$_r$)—N—S(O)$_2$—R$_s$— or —R$_t$(R$_r$)—N—S(O)$_2$—R$_s$, where R$_t$, R$_r$, and R$_s$ can be, for example, hydrogen, alkyl, alkenyl, alkynyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonate" as used herein refers to the radical —OSO$_3$—. Sulfonate includes salts such as —OSO$_3$Na, —OSO$_3$K, etc. and the acid —OSO$_3$H The term "sulfonic acid" refers to the radical —SO$_3$H— and its corresponding salts, e.g. —SO$_3$K—, —SO$_3$Na—.

The term "sulfonyl" as used herein refers to a radical having the structure R$_u$SO$_2$—, where R$_u$ can be alkyl, alkenyl, alkynyl, amino, amide, aryl, cycloalkyl, and heterocyclyl, e.g., alkylsulfdnyl. The term "alkylsulfonyl" as used herein refers to an alkyl group attached to a sulfonyl group. "Alkylsulfonyl" groups can optionally contain alkenyl or alkynyl groups.

The term "thioketone" refers to a radical having the structure —R$_v$—C(S)—R$_w$—. The ketone can be attached to another group through R$_v$ or R$_w$. R$_v$ or R$_w$ can be alkyl, alkenyl, alkynyl, cycloalkyl, heterocyclyl or aryl, or R$_v$ or R$_w$ can be joined to form a 3- to 12-membered-ring.

"Alkyl," "alkenyl," and "alkynyl" groups, collectively referred to as "saturated and unsaturated hydrocarbons," and "alkoxy" groups can be substituted with or interrupted by at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, heterocyclyloxy, hydroxyl, ketone, nitro, phosphate, sulfide, sulfinyl, sulfonyl, sulfonic acid, sulfonamide, thioketone, and N.

As used herein, a "suitable substituent" refers to a group that does not nullify the synthetic or pharmaceutical utility of the compounds of the invention or the intermediates useful for preparing them. Examples of suitable substituents include, but are not limited to: C$_{1-22}$, C$_{1-8}$, and C$_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N(($C_{1-22}$, $C_{1-8}$, and $C_{1-6}$ alkyl)$_2$, —NH(($C_6$)aryl), or —N(($C_6$)aryl)$_2$; formyl; ketones, such as; —CO($C_{1-22}$, $C_{1-8}$, and $C_{1-6}$ alkyl), —CO(($C_6$ aryl) esters, such as —CO$_2$($C_{1-22}$, $C_{1-8}$ and $C_{1-6}$ alkyl) and —CO$_2$ ($C_6$ aryl); and heterocyclyl. One of skill in art can readily choose a suitable substituent based on the stability and pharmacological and synthetic activity of the compound of the invention.

The term "pharmaceutically acceptable carder" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention. A discussion is provided in Higuchi et al., "Prodrugs as Novel Delivery Systems," *ACS Symposium Series*, Vol. 14, and in Roche, E. B., ed. *Bioreversible Carriers in Drug* Design, American Pharmaceutical Association and Pergamon Press, 1987, both of which are incorporated herein by reference.

In one embodiment, pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of Formula 1. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed compounds to achieve a desired effect.

The term "pharmaceutically acceptable salt(s)" or "complexes" refers to salts of acidic or basic groups that may be present in compounds used in the present compositions. In one embodiment, these salts retain the desired biological activity of the compounds of the present invention and exhibit minimal undesired toxicological effects. Examples of pharmaceutically acceptable salts are organic acid addition salts formed with acids, which form a physiological acceptable anion, for example, tosylate, methanesulfonate, acetate, citrate, malonate, tartarate; succinate, benzoate, ascorbate, .alpha.-ketoglutarate and .alpha.-glycerophosphate. Suitable inorganic salts may also be formed, including, sulfate, nitrate, bicarbonate and carbonate salts Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR.sup.+A.sup.-, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Particular FDA-approved salts can be conveniently divided between anions and cations (Approved Drug Products with Therapeutic Equivalence Evaluations (1994) U.S. Department of Health and Human Services, Public Health Service, FDA, Center for Drug Evaluation and Research, Rockville, Md.; L. D. Bighley, S. M. Berge and D. C. Monkhouse, Salt Forms of Drugs and Absorption, Encyclopedia of Pharmaceutical Technology, Vol. 13, J. Swarbridk and J. Boylan, eds., Marcel Dekker, NY (1996)). Among the approved anions include aceglumate, acephyllinate, acetamidbbenzoate, acetate, acetylasparaginate, acetylaspartate, adipate, aminosalicylate, anhydromethylenecitrate, ascorbate, aspartate, benzoate, besylate, bicarbonate, bisulfate, bitartrate, borate, bromide, camphorate, camsylate, carbonate, chloride, chlorophenoxyacetate, citrate, closylate, cromesilate, cyclamate, dehydrocholate, dihydrochloride, dimalonate, edentate, edisylate, estolate, esylate, ethylbromide, ethylsulfate, fendizoate, fosfatex, fumarate, gluceptate, gluconate, glucuronate, glutamate, glycerophosphate, glysinate, glycollylarsinilate, glycyrrhizate, hippurate, hemisulfate, hexylresorcinate, hybenzate, hydrobromide, hydrochloride, hydroiodid, hydroxybenzenesulfonate, hydroxybenzoate, hydroxynaphthoate, hyclate, iodide, isethionate, lactate, lactobionate, lysine, malate, maleate, mesylate, methylbromide, methyliodide, methylnitrate, methylsulfate, monophosadenine, mucate, napadisylate, napsylate, nicotinate, nitrate, oleate, orotate, oxalate, oxoglurate, pamoate, pantothenate, pectinate, phenylethylbarbiturate, phosphate, pacrate, plicrilix, polistirex, polygalacturonate, propionate, pyridoxylphosphate, saccharinate, salicylate, stearate, succinate, stearylsulfate, subacetate, succinate, sulfate, sulfosalicylate, tannate, tartrate, teprosilate, terephthalate, teoclate, thiocyante, tidiacicate, timonacicate, tosylate, triethiodide, triethiodide, undecanoate, and xinafoate. The approved cations include ammonium, benethamine, benzathine, betaine, calcium, camitine, clemizole, chlorcyclizine, choline, dibenzylamine, diethanolamine, diethylamine, diethylammonium diolamine, eglumine, erbumine, ethylenediamine, heptaminol, hydrabamine, hydroxyethylpyrrolidone, imadazole, meglumine, olamine, piperazine, 4-phenylcyclohexylamine, procaine, pyridoxine, triethanolamine, and tromethamine. Metallic cations include, aluminum, bismuth, calcium lithium, magnesium, neodymium, potassium, rubidium, sodium, strontium and zinc.

A particular class of salts can be classified as organic amine salts. The organic amines used to form these salts can be primary amines, secondary amines or tertiary amines, and the substituents on the amine can be straight, branched or cyclic groups, including ringed structures formed by attachment of two or more of the amine substituents. Of particular interest are organic amines that are substituted by one or more hydroxyalkyl groups, including alditol or carbohydrate moieties. These hydroxy substituted organic amines can be cyclic or acyclic, both classes of which can be primary amines, secondary amines or tertiary amines. A common class of cyclic hydroxy substituted amines is the amino sugars.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

It is appreciated that compounds of the present invention may have a chiral center and may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the 'Z' or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring is designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Embodiments Of The Invention

One embodiment provides methods for inhibiting VCAM-1 expression, MCP-1 expression and/or SMC proliferation in a mammal, comprising administering a therapeutically effective amount of a compound of Formula 1:

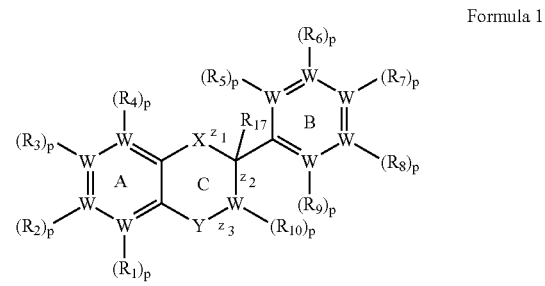

Formula 1 wherein:
X is selected from $CR_{11}$, $CR_{11}R_{13}$, CO, CS, O, S, SO, $SO_2$, N and $NR_{11}$, wherein $R_1$, may be the same or different than $R_{13}$;
Y is selected from $CR_{12}$, $CR_{12}R_{14}$, CO, CS, O, S, SO, $SO_2$, N and $NR_{12}$, wherein $R_{12}$ may be the same or different than $R_{14}$;
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone, or
two adjacent substituents selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are connected in a 5 or 6-membered ring to form a bicyclic aryl, bicyclic heteroaryl or bicyclic heterocyclyl;
each W is independently selected from C and N, wherein if W is N, then p is 0 and if W is C, then p is 1;
$Z_1$, $Z_2$ and $Z_3$ are each independently selected from a single bond and a double bond;
wherein if Y is O, then X is not CO;
wherein if at least one W is not N, then
a) X and Y are each CO,
b) X is $NR_{11}$ and $Z_2$ is a double bond, or
c) two adjacent substituents selected from $R_5$, $R_6$, $R_7$, $R_8$, and $R_9$ are connected in a 5 or 6-membered ring to form a bicyclic aryl, bicyclic heteroaryl or bicyclic heterocyclyl;
and pharmaceutically acceptable salts and hydrates thereof.

In one embodiment, $R_7$ is hydroxyl. In another embodiment, at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ is selected from alkoxy, alkyl, amino, aminoalkoxy, aminoalkyl, carboxyalkoxy, halogen, heterocyclyl, heterocyclylalkoxy, heterocyclylalkyl, hydroxyalkoxy, hydroxyalkyl, and hydroxyl.

In one embodiment, X is selected from $CR_{11}$, CO, N, $NR_{11}$ and O; and Y is selected from $CR_{12}$, CO, and $NR_{12}$. In another embodiment, X is O and Y is CO.

In one embodiment, $Z_1$ and $Z_3$ are single bonds, and $Z_2$ is a double bond. In another embodiment, $Z_1$ is a double bond and Y is CO. In another embodiment, $Z_1$ and $Z_3$ are double bonds.

In one embodiment, at least one-W in the A ring of Formula 1 is N. In another embodiment, the W bonded to $(R_4)_p$ is N. In another embodiment, the W bonded to $(R_{10})_p$ is N. Another embodiment provides that at least one W in the C ring of Formula 1 is N. In another embodiment, the W bonded to $(R_7)_p$ is N.

One embodiment provides a compound of Formula I:

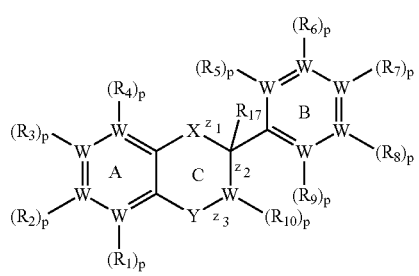

Formula 1 wherein:

X is selected from $CR_{11}$, CO, N, $NR_{11}$ and O;

Y is selected from $CR_{12}$, CO, and $NR_{12}$;

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ and $R_{17}$ are each independently selected from alkoxy, alkyl, amino, aminoalkoxy, aminoalkyl, carboxyalkoxy, halogen, heterocyclyl, heterocyclylalkoxy, heterocyclylalkyl, hydrogen, hydroxyalkoxy, hydroxyalkyl, and hydroxyl, or two adjacent substituents selected from $R_5$, $R_6$, $R_7$, $R_8$ and $R_9$ are connected in a 5 or 6-membered ring to form a bicyclic aryl, bicyclic heteroaryl or bicyclic heterocyclyl;

each W is independently selected from C and N, wherein if W is N, then p is 0 and if W is C, then p is 1;

$Z_1$, $Z_2$ and $Z_3$ are each independently selected from a single bond and a double bond;

wherein if at least one W is not N, then a) X and Y are each CO, or b) X is $NR_{11}$ and $Z_2$ is a double bond;

and pharmaceutically acceptable salts and hydrates thereof.

An alternative embodiment provides compounds of Formula 1:

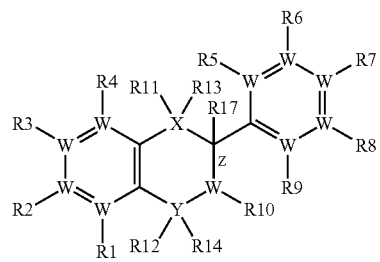

or a pharmaceutically acceptable salt thereof,
wherein
R1, R2, R3, R4, R5, R6, R7, R8, R9, R10, R11, R12, R13, R14, and R17 are independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, thioketone, hydrogen, hydroxyl (OH), acetyl, hydroxyalkyl, aminoalkyl, amides, carbamates, halogen, bromide (Br), iodide (I), fluoride (F), chloride (Cl), $CF_3$, $CCl_3$, sulfonic acid (—$SO_3H$), phosphate, O-sulfate (sulfate conjugate), O-glucoronidate [glucoronic (glucuronic) acid conjugates], monoesters, dicarboxylic acid, #STR55#, #STR66#, #STR77#, #STR88#, #STR99#, #STR100#, wherein W can be C or N;

wherein when W is a nitrogen atom, the nitrogen atom will only bind to three covalent bonds due to available valence electrons.

The structures below demonstrate a nitrogen arrangement of one embodiment of the compounds of Formula 1:

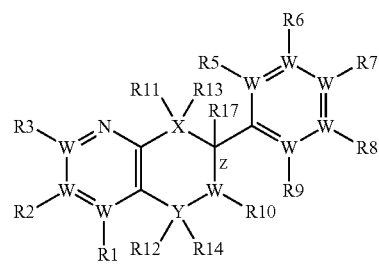

wherein the same applies to any W;

or

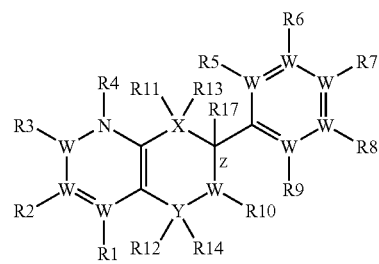

wherein the same applies to any W:

wherein

X can be CH, $CH_2$, CR11, CR13, CHR11, CHR13, CR11R13, CS, O, S, SO, $SO_2$, NH, NR11 with the proviso that X and Y do not exceed the number of valence electrons available as per definitions of X and Y above Y can be CH, $CH_2$, CR12, CR14, CHR12, CHR14, CR11R14, CO, CS, O, S, SO, $SO_2$, NH, NR11 with the proviso that X and Y do not exceed the number of valence electrons available as per definitions of X and Y above Z can be a single, double bond or triple bond, with the proviso that X and Y do not exceed the number of valence electrons available as per definitions of X and Y above Wherein

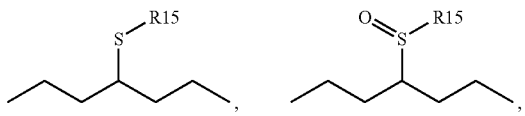

-continued

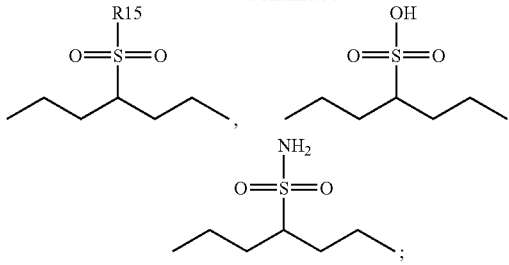

STR55# is

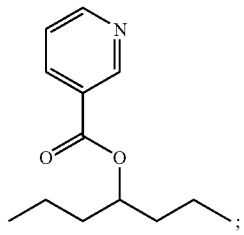 [SMILES: CCCC(CCC)OC(=O)c1cccnc1]

STR66# is

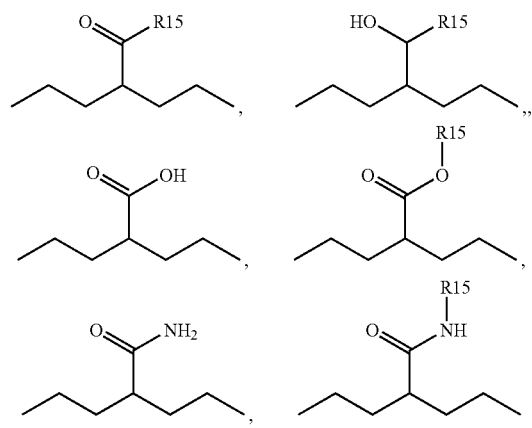

STR77# is
or

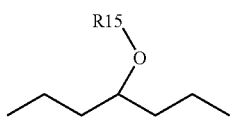

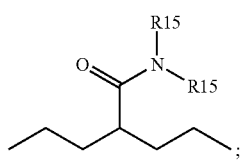

STR88# is

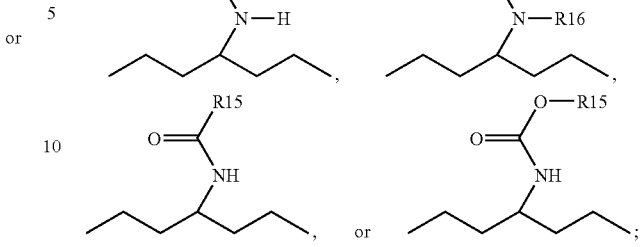

STR99# is

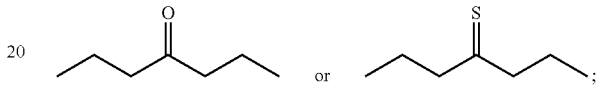

STR100# is
R15 and R16 are substituents independently selected from the group consisting of $(C_1-C_{22})$alkyl, $(C_2-C_{22})$alkenyl, $(C_2-C_{22})$alkynyl, aryl, heteroaryl, alkoxy, aryloxy, benzyl, phenyl, carbonyl, hydrogen, hydroxyl (OH), acetyl, hydroxyalkyl, aminoalkyl, amides, carbamates, halogen, bromide (Br), iodide (I), fluoride (F), chloride (Cl), $CF_3$, $CCl_3$, sulfonic acid ($-SO_3H$), phosphate, or a derivative thereof, wherein said derivative is optionally substituted and optionally branched, and may have one or more of the C atoms replaced by S, N or O;
wherein Formula 1 compounds have at least one proviso selected from the following
R7 is a hydroxyl;
at least one W is a N;
at least one of R1-R10 is #STR77#, #STR88# or #STR99#;
at least one of R1-R10 is #STR66#;
one of R1-R10 is a monoester;
one of R1-R10 is a dicarboxylic acid;
one of R1-R10 is succinic acid;
R7 is #STR55#;
R7 and R2 are #STR55#;
R7 and R2 are hydroxyls; and
R7 is #STR66#.
Non-limiting embodiments of Formula 1 include:
R7 is a hydroxyl and at least one W is a N;
R7 is a hydroxyl and at least one of R1-R6 and R8-R10 is #STR66#;
R7 is a hydroxyl and at least one of R1-R6 and R8-R10 is #STR77#, #STR88# or #STR99#; and
R7 is #STR66# and at least one W is a N.
Other alternative embodiments of Formula 1 include

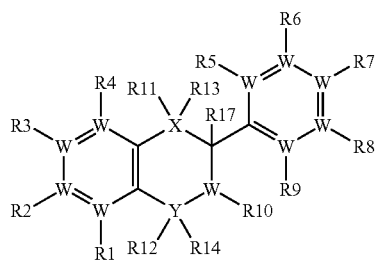

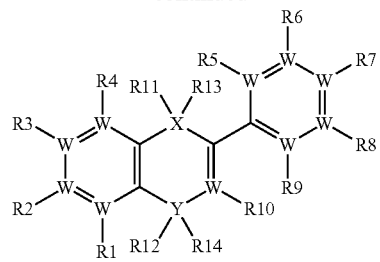
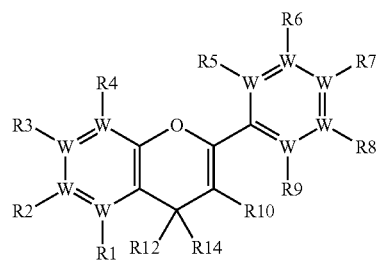
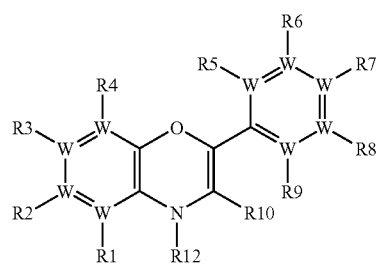
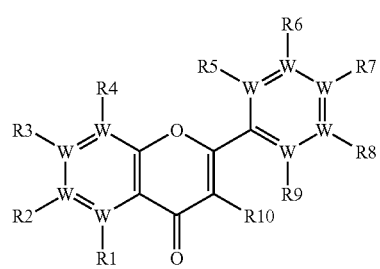
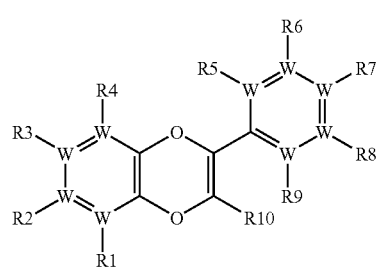
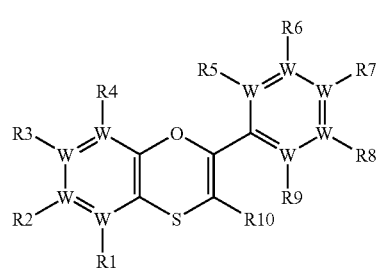
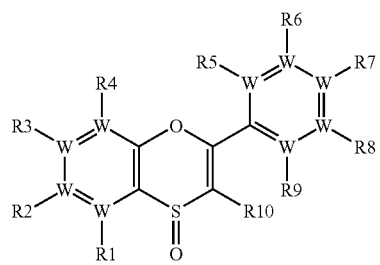
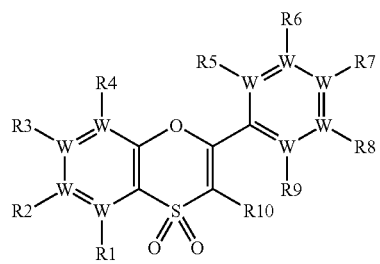
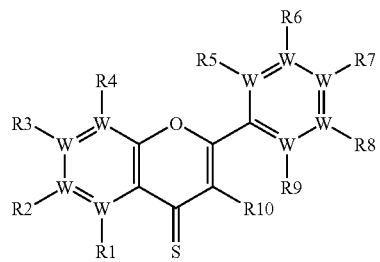
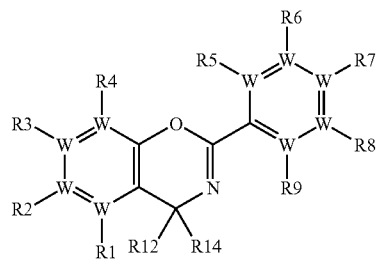
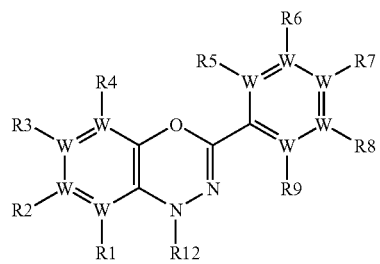
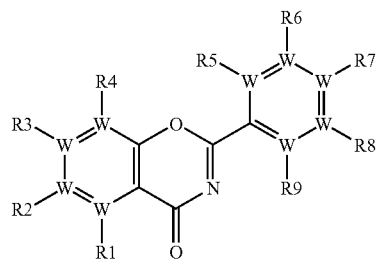

-continued

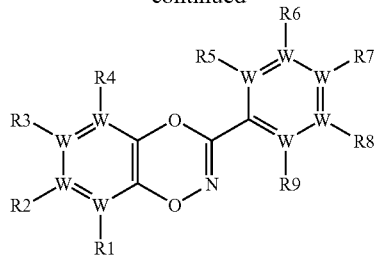

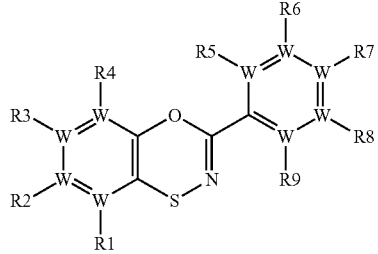

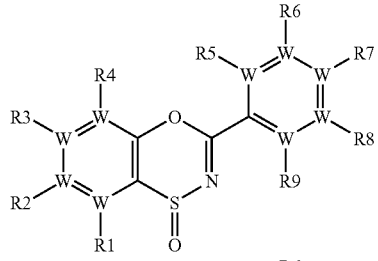

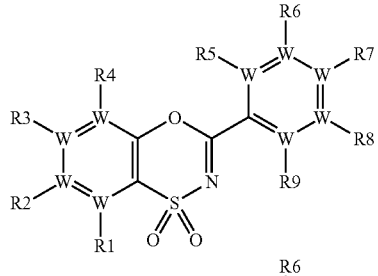

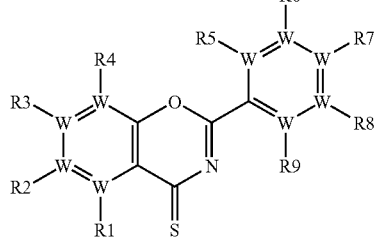

or a pharmaceutically acceptable salt thereof,
wherein
R1, R2, R3, R4, R5, R6, R7, R8, R9, R10, R11, R12, R13, R14, and R17 are independently selected from the group consisting of $(C_1-C_{22})$alkyl, $(C_2-C_{22})$alkenyl, $(C_1-C_{22})$ alkynyl, aryl, heteroaryl, alkoxy, aryloxy, benzyl, phenyl, carbonyl, thioketone, hydrogen, hydroxyl [OH], acetyl, hydroxyalkyl, aminoalkyl, amides, carbamates, halogen, bromide [Br], iodide [I], fluoride [F], chloride [Cl], $CF_3$, $CCl_3$, sulfonic acid [—$SO_3H$], phosphate, O-sulfate [the sulfate conjugate], O-glucoronidate [the glucoronic (AKA glucuronic) acid conjugates], monoesters, dicarboxylic acid, #STR55#, #STR66#, #STR77#, #STR88#, #STR99#, #STR100#,
wherein W can be C or N;

wherein when W is a nitrogen atom, the nitrogen atom will only bind to three covalent bonds due to available valence electrons.

The structures below demonstrate a nitrogen arrangement of one embodiment of the compounds of Formula 1:

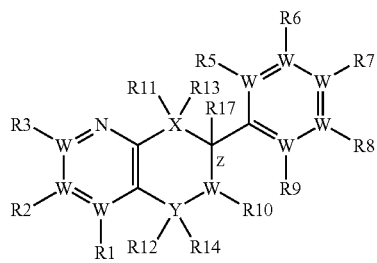

wherein the same applies to any W;
or

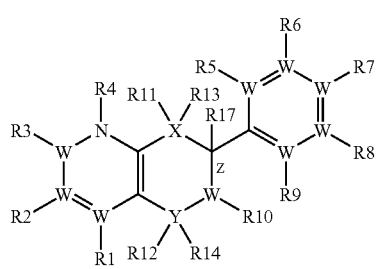

wherein the same applies to any W:
wherein
X can be CH, $CH_2$, CR11, CR13, CHR11, CHR13, CR11R13, CS, O, S, SO, $SO_2$, NH, NR11 with the proviso that X and Y do not exceed the number of valence electrons available as per definitions of X and Y above
Y can be CH, $CH_2$, CR12, CR14, CHR12, CHR14, CR11R14, CO, CS, O, S, SO, $SO_2$, NH, NR11 with the proviso that X and Y do not exceed the number of valence electrons available as per definitions of X and Y above
Z can be a single, double bond or triple bond, with the proviso that X and Y do not exceed the number of valence electrons available as per definitions of X and Y above
wherein

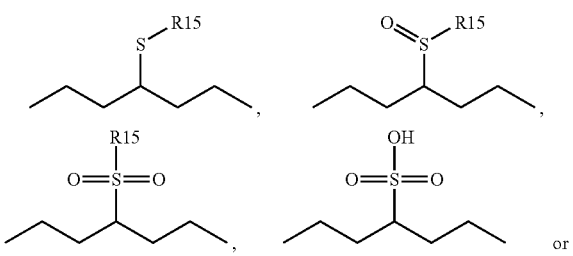

STR55# is

[structure: sulfonamide]

STR66# is

[structure: nicotinate ester]

[structures for R15 variants: ketone, hydroxyalkyl, carboxylic acid, ester, amide, N-substituted amide]

STR77# is or

[structure: N,N-disubstituted amide]

STR88# is

[structures: ether and carbonate]

STR99# is

[structures: amines and carbamates]

STR100# is

[structures: ketone and thioketone]

R15 and R16 are substituents independently selected from the group consisting of $(C_1-C_{22})$alkyl, $(C_2-C_{22})$alkenyl, $(C_1-C_{22})$alkynyl, aryl, heteroaryl, alkoxy, aryloxy, benzyl, phenyl, carbonyl, hydrogen, hydroxyl (OH), acetyl, hydroxyalkyl, aminoalkyl, amides, carbamates, halogen, bromide (Br), iodide(I), fluoride (F), chloride (Cl), $CF_3$, $CCl_3$, sulfonic acid ($-SO_3H$), phosphate, or a derivative thereof, wherein said derivative is optionally substituted and optionally branched, and may have one or more of the C atoms replaced by S, N or O;

wherein non limiting examples of Formula 1 have at least one proviso selected from the following:
R7 is a hydroxyl;
at least one W is a N;
at least one of R1-R10 is #STR77#, #STR88# or #STR99#;
at least one of R1-R10 is #STR66#;
one of R1-R10 is a monoester;
one of R1-R10 is a dicarboxylic acid;
one of R1-R10 is succinic acid;
R7 is #STR55#;
R7 and R2 are #STR55#;
R7 and R2 are hydroxyls; and
R7 is #STR66#.

Non-limiting examples include compounds of Formula 1 where
R7 is a hydroxyl and at least one W is a N;
R7 is a hydroxyl and at least one of R1-R6 and R8-R10 is #STR66#;
R7 is a hydroxyl and at least one of R1-R6 and R8-R10 is #STR77#, #STR88# or #STR99#; and
R7 is #STR66# and at least one W is a N.

Pharmaceutical Formulations and Methods of Treatment

Embodiments of the present invention also provide pharmaceutical compositions comprising compounds disclosed herein formulated together with one or more pharmaceutically acceptable carriers. These formulations include those suitable for oral, rectal, topical, buccal and parenteral (e.g., subcutaneous, intramuscular, intradermal, intravenous) administration, although the most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of the compound as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with the compound as a unit-dose formulation, for example, a tablet, which may contain from 0.05% to 95% by weight of the active compound. Other pharmacologically active substances may also be present including other compounds. The formulations of the invention may be prepared by any of the well known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving or dispersing, an active compound as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the active compound with a liquid or finely divided solid carrier, or both, and then, if necessary, shaping the product. For example, a tablet may be prepared by compressing or molding a powder or granules of the compound, optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Molded tablets may be made by molding, in a suitable machine, the powdered compound moistened with an inert liquid diluent.

Formulations suitable for buccal (sub-lingual) administration include lozenges comprising a compound in a flavored base, usually sucrose and acacia or tragacanth, and pastilles comprising the compound in an inert base such as gelatin and glycerin or sucrose and acacia.

Formulations of the present invention suitable for parenteral administration comprise sterile aqueous preparations of the compounds, which are approximately isotonic with the blood of the intended recipient. These preparations are administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention may contain from 0.1 to 5% w/w of the active compound.

Formulations suitable for rectal administration are presented as unit-dose suppositories. These may be prepared by admixing the compound with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician.

In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by assessing the therapeutic effectiveness of the compound. Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture assays or animal models. Levels in plasma may be measured, for example, by high performance liquid chromatography. The effects of any particular dosage can be monitored by a suitable bioassay. Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

Data obtained from the cell culture assays or animal studies can be used in formulating a range of dosage for use in humans. Therapeutically effective dosages achieved in one animal model may be converted for use in another animal, including humans, using conversion factors known in the art (e.g., Freireich et al. (1966) *Cancer Chemother Reports* 50, 219-244) and Table 1 for Equivalent Surface Area Dosage Factors).

TABLE 1

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and sex, as well as the severity of the medical condition in the subject. The dosage may be determined by a physician and adjusted, as necessary, to suit observed effects of the treatment.

In one embodiment, a compound as disclosed herein, or a pharmaceutically acceptable salt or hydrate thereof, is administered in combination with another therapeutic agent. The other therapeutic agent can provide additive or synergistic value relative to the administration of a flavonoid compound alone. The therapeutic agent can be, for example, a statin, a PPAR agonist (e.g., a thiazolidinedione or fibrate), a bile-acid-binding-resin, niacini a RXR agonist, an anti-obesity drug, a hormone, a tyrophostine, a sulfonylurea-based drug, a biguanide, an alpha-glucosidase inhibitor, apolipoprotein E, a cardiovascular drug, an HDL-raising drug, an HDL enhancer, or a regulator of the apolipoprotein A-IV and/or apolipoprotein genes.

One embodiment provides methods for treating, preventing or mitigating inflammatory conditions and related disease states, characterized by altered expression of markers of inflammation such as VCAM-1, MCP-1 and/or SMC proliferation, in a mammal. In one embodiment, the inflammatory conditions and related disease states are those where inhibition of VCAM-1, MCP-1 and/or SMC proliferation is desirable.

Another embodiment provides methods for regulating-markers of inflammation, including vascular inflammation, and their use in the treatment and prevention of inflammatory and cardiovascular diseases and related disease states in a mammal.

In one embodiment, a method of treating, preventing or mitigating inflammatory conditions, such as cardiovascular or inflammatory disorders, comprises administering a therapeutically effective amount of a disclosed compound. The disclosed compound may be administered as a pharmaceutically acceptable composition, comprising a disclosed compound and a pharmaceutically acceptable carrier. In another embodiment, a compound of the present invention is administered as a pharmaceutically acceptable composition, pharmaceutically acceptable salt, or pharmaceutically acceptable formulation; optionally in a combination or alternation therapy with a therapeutic agent or at least one other compound of the present invention. In combination therapy, effective dosages of two or more agents are administered together, whereas during alternation therapy an effective dosage of each agent is administered serially.

In another embodiment, a compound of the present invention is administered as a pharmaceutical formulation, or prodrug; optionally in a combination or alternation therapy with a therapeutic agent or at least one other compound of the present invention.

Embodiments of the present invention provide methods for treating, preventing or mitigating cardiovascular disorders mediated by VCAM-1, MCP-1, and/or SMC proliferation, comprising administering to a patient a therapeutically effective amount of a compound of the invention, or in another embodiment, a composition comprising a compound of the invention and a pharmaceutically acceptable carrier.

"Cardiovascular disease" refers to diseases of the heart and circulatory system. Cardiovascular diseases that the compounds of the present invention are useful for preventing or treating include metabolic syndrome, arteriosclerosis, atherosclerosis, angina, stroke, ischemia, endothelial dysfunction (in particular those affecting blood vessel elasticity), peripheral vascular disease, coronary heart disease, myocardial infarction, cerebral infarction, obesity, reperfusion injury, angioplasty restenosis, hypertension, vascular complications of diabetes and thrombosis.

In a preferred embodiment, a compound of the present invention is administered to a patient in a therapeutically effective amount for treating, preventing or mitigating a cardiovascular disease. In another embodiment, the compound of the present invention is administered as a pharmaceutically acceptable composition, pharmaceutically acceptable salt, or pharmaceutically acceptable formulation; optionally in a combination or alternation therapy with a therapeutic agent or at least one other compound of the present invention.

In a preferred embodiment, a compound of the present invention is administered to a patient in a therapeutically effective amount for treating, preventing, or mitigating restenosis. In one embodiment, the restenosis is angioplasty restenosis. In another embodiment, the restenosis is post-angioplasty restenosis. In another embodiment, the compound of the present invention is administered as a pharmaceutically acceptable formulation, or prodrug; optionally in a combination or alternation therapy with a therapeutic agent or at least one other compound of the present invention.

Embodiments of the present invention provide methods for treating, preventing or mitigating inflammatory disorders mediated by VCAM-1 and/or MCP-1, comprising administering to a patient a therapeutically effective amount of a compound of the invention, or in another embodiment, a composition comprising a compound of the invention and a pharmaceutically acceptable carrier.

"Inflammatory disorders" includes diseases that are mediated by VCAM-1 and/or MCP-1. Inflammatory disorders that the compounds of the present invention are useful for preventing or treating include arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion-injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

In one embodiment, the inflammatory disorders that the compounds of the present invention are useful for preventing or treating comprise diseases, conditions and disorders mediated by VCAM-1, MCP-1, and/or SMC proliferation that are not disclosed in PCT/US2005/038048. For example, inflammatory disorders may not be ischemia-reperfusion injury, post-angioplasty restenosis, atherosclerosis, coronary artery disease, angina, and small artery disease.

In a preferred embodiment, a compound of the present invention is administered to a patient in a therapeutically effective amount for inhibition of VCAM-1 expression. In another embodiment, the compound of the present invention is administered as a pharmaceutically acceptable composition, a pharmaceutically acceptable salt, or a pharmaceutically acceptable formulation; optionally in a combination or alternation therapy with a therapeutic agent or at least one compound of the present invention.

In a preferred embodiment, a compound of the present invention is administered to a patient in a therapeutically effective amount for inhibition of MCP-1 expression. In another embodiment, the compound of the present invention is administered as a pharmaceutically acceptable composition, a pharmaceutically acceptable salt, or a pharmaceutically acceptable formulation; optionally in a combination or alternation therapy with a therapeutic agent or at least one compound of the present invention.

In a preferred embodiment, a compound of the present invention is administered to a patient in a therapeutically effective amount for inhibition of SMC proliferation. In another embodiment, the compound of the present invention is administered as a pharmaceutically acceptable composition, a pharmaceutically acceptable salt, or a pharmaceutically acceptable formulation; optionally in a combination or alternation therapy with a therapeutic agent or at least one compound of the present invention.

In a preferred embodiment, a compound of the present invention is administered to a patient in a therapeutically effective amount for inhibition of MCP-1 and VCAM-1 expression. In another embodiment, the compound of the present invention is administered as a pharmaceutically acceptable composition, a pharmaceutically acceptable salt, or a pharmaceutically acceptable formulation; optionally in a combination or alternation therapy with a therapeutic agent or at least one compound of the present invention.

In another aspect, the present invention provides for the use of the compounds of the present invention for the manufacture of a medicament for treating, preventing or mitigating diseases or disorders mediated by SMC proliferation wherein such compositions comprise an effective SMC proliferation-inhibiting amount of a compound of the present invention or a pharmaceutically acceptable salt thereof and/or a pharmaceutically acceptable composition.

In another aspect, the present invention provides a method for treating, preventing or mitigating a disease or disorder mediated by SMC proliferation comprising administering to a patient an effective SMC proliferation-inhibiting amount of a compound of the present invention or a pharmaceutically acceptable salt thereof and/or a pharmaceutically acceptable composition.

Embodiments of the present invention include the use of the disclosed compounds for the manufacture of a medicament for treating, preventing or mitigating inflammatory conditions.

Embodiments of the present invention include the use of the disclosed compounds for the manufacture of a medicament for treating, preventing or mitigating diseases or disorders mediated by VCAM-1 expression.

Embodiments of the present invention include the use of the disclosed compounds for the manufacture of a medicament for treating, preventing or mitigating diseases or disorders mediated by MCP-1 expression.

Embodiments of the present invention include the use of the disclosed compounds for the manufacture of a medicament for treating, preventing or mitigating diseases or disorders mediated by smooth muscle cell proliferation.

Stents

Given the correlation between physical injury to the vasculature and restenosis, for example that arising after angioplasty, it is explicitly contemplated that the compounds of the present invention are capable of being used before, contemporaneously with, or subsequent to angioplasty or other medical treatment expected to give rise to a vascular injury, localized vascular inflammatory response or vascular injury response.

In a preferred embodiment, a compound of the present invention is administered through the use of an intraluminal stent. In another embodiment, the compound of the present invention is administered as a pharmaceutically acceptable formulation, prodrug, as a pharmaceutically acceptable salt or in a combination or alternation therapy with a therapeutic agent or at least one compound of the present invention.

Compounds of the present invention may be eluted through a stent or alternatively may be coated on the stent allowing for controlled release to the local environment, as taught by U.S. Pat. Nos. 5,837,008, 5,824,048, 5,679,400, 5,464,650, 6,908,624, 6,890,583, and 6,790,228.

In another aspect, compounds of the present invention may be administered in a therapeutically effective amount for treatment of small vessel disease not otherwise treatable by surgery or angioplasty or other vascular disease in which surgery is not a preferred option. In a preferred embodiment a compound of the present invention is administered in a therapeutically effective amount systemically or local to the locus of the small vessel disease. In another embodiment, the compound of the present invention is administered as a pharmaceutically acceptable formulation, prodrug, pharmaceutically acceptable salt or in a combination or alternation therapy with a therapeutic agent or at least one compound of the present invention.

In a further aspect, compounds of the present invention can be administered in a therapeutically effective amount prior to revascularization therapy. In a preferred embodiment, a compound of the present invention is administered in a therapeutically effective amount systemically or local to the site of revascularization. In another embodiment, a compound of the present invention is administered as a pharmaceutically acceptable formulation, prodrug, pharmaceutically acceptable salt or in a combination or alternation therapy with a therapeutic agent or at least one compound of the present invention.

Treatment or Prevention of Other Related Diseases

In a preferred embodiment, a compound of the present invention is administered as a preventative measure to a patient having a nongenetic predisposition to a disease including a cardiovascular disease or an inflammatory disorder. Examples of such non-genetic predispositions include cardiac bypass surgery and PTCA (which can lead to restenosis), an accelerated form of atherosclerosis, diabetes in women, (which can lead to polycystic ovarian disease), and cardiovascular disease (which can lead to impotence). Accordingly, compositions of the invention may be used for the prevention of one disease or disorder and concurrently treating another (e.g., prevention of polycystic ovarian disease while treating diabetes; prevention of impotence while treating a cardiovascular disease).

Preparation of Compounds

The following examples demonstrate methods to synthesize compounds of the invention wherein each W is independently a nitrogen or carbon, and an R-group may be independently-selected from the aforementioned group of substituents. The chosen synthetic method may involve use of protecting groups, which can be selected from those known in the art (e.g., *Protective Groups in Organic Synthesis*, By T W Greene & P G M Wuts John Wiley & Sons, New York, 1991, 2nd ed). Compounds synthesized in the manner described below may additionally be modified by functional group manipulations (e.g., *Organic Synthesis* by M B Smith, McGraw-Hill, New York, 1994, Int. Ed. Chapter 2), including reduction, oxidation, alkylation, and acylation.

Flavonoid compounds may be represented by the general structure of Formula A.

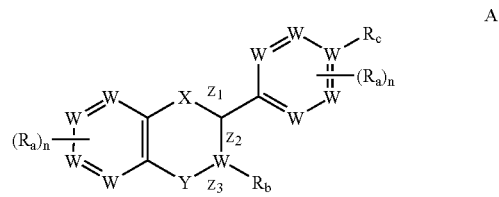

$R_a$ may be selected from groups including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. $R_b$ may be selected from groups including alkyl, amino, cyano, halogen and hydrogen. $R_c$ represents substituents such as alkyl, alkoxy, halogen, hydroxyl and hydrogen.

One of ordinary skill will appreciate that flavonoid compounds as disclosed herein may be synthesized from readily available starting materials as outlined below.

Formula B represents a general formula for flavonoid compounds comprising a phenyl-chromene:

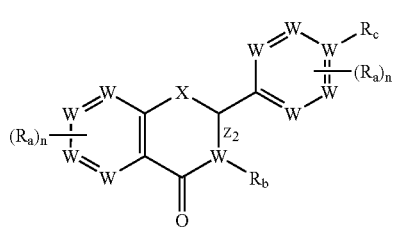

Flavonoids of Formula B can be synthesized by the procedure of Scheme 1:

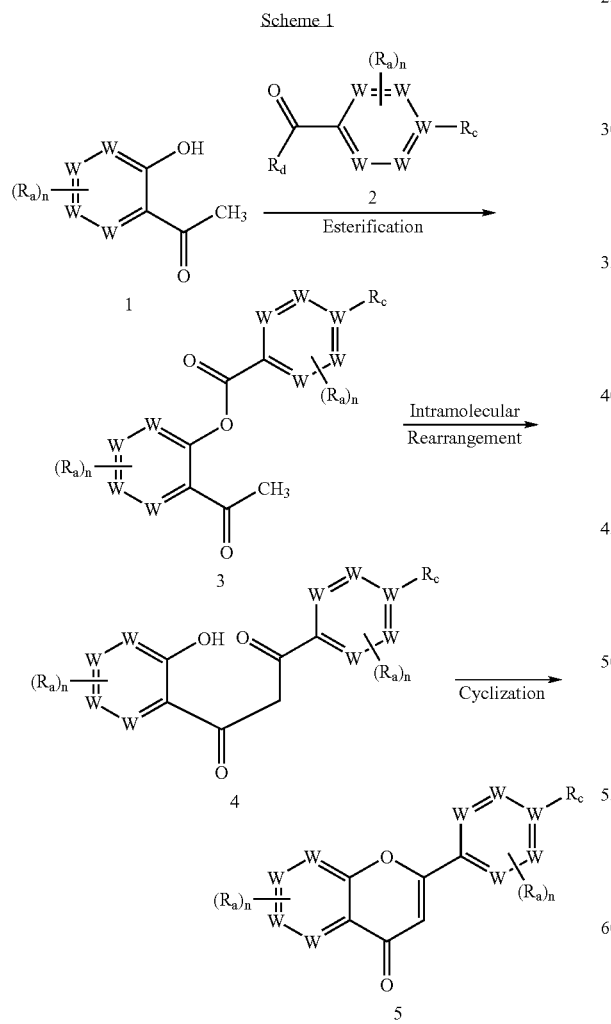

Acid chloride 2 ($R_d$=Cl) may be used directly in a reaction with acetophenone 1 to provide ester 3. The acid chloride may also be generated in situ by exposing the carboxylic acid 2 ($R_d$=OH) to a chlorinating agent such as $POCl_3$. Ester 3 can be converted into diketone 4 via intramolecular rearrangement. Rearrangement may be achieved using a catalytic amount of base, such as potassium t-butoxide, KOH, NaH and the like. Cyclization of phenol 4 to flavonoid 5 can be achieved by heating phenol 4 in the presence of a strong protic (HCl, AcOH, HI, AcOH, HBr, and mixtures thereof) or Lewis ($BBr_3$) acid.

Flavonoid compounds can be synthesized following the procedure of Scheme 2:

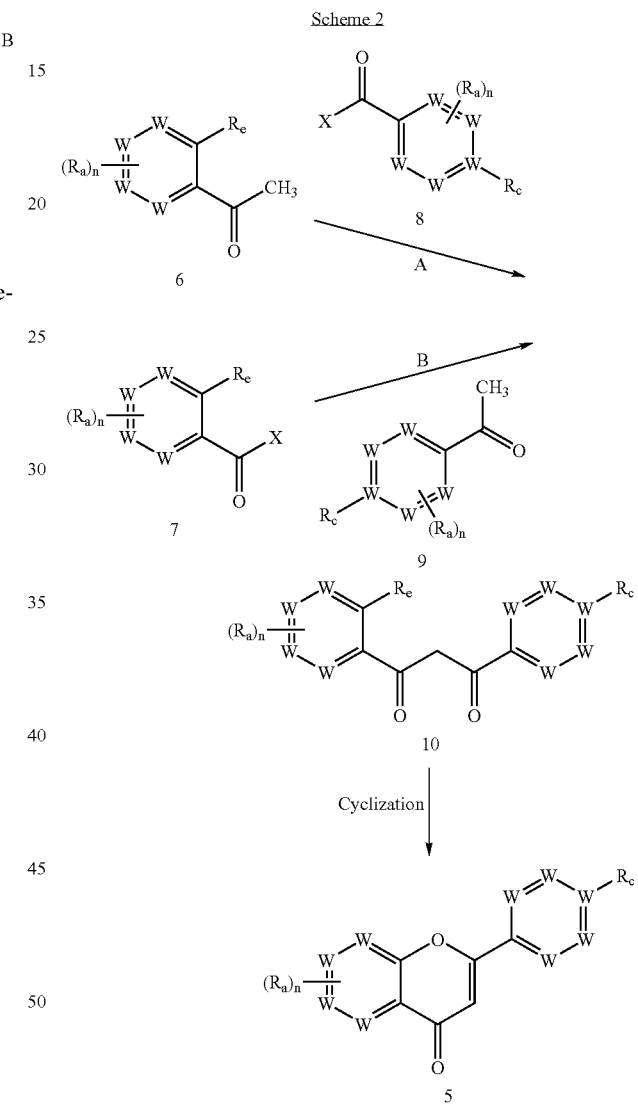

Diketone 10 may be prepared by first exposing methyl ketones 6 or 9 to basic conditions, such as potassium t-butoxide, KOH, NaH and the like, to form the corresponding enolate. Then, reaction with acyl halide 8 or 7 (X=Hal), respectively, affords diketone 10. Cyclization of diketone 10 to flavonoid 5 may likewise be accomplished by a number of methods. When $R_e$=F, exposure of 10 to heat and a polar solvent results in ring closure via nucleophilic aromatic substitution. Alternatively, strong protic or Lewis acids may be used when $R_e$=alkoxy, SH, or $NH_2$. Suitable acids include HCl, AcOH, HI, AcOH, HBr, $BBr_3$, and mixtures thereof.

Formula C represents flavonoid compounds comprising a naphthyl:

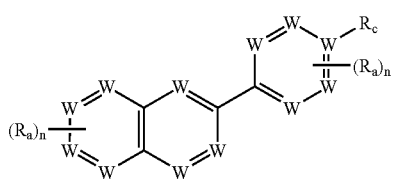

Flavonoids of Formula C can be prepared via the procedure of Scheme 3.

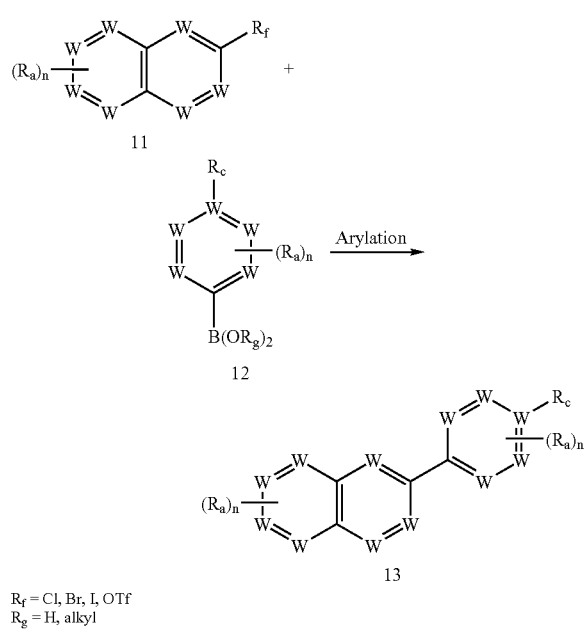

$R_f$ = Cl, Br, I, OTf
$R_g$ = H, alkyl

Arylation of naphthalene analog 11 with boronic acid (or boronic ester) 12 occurs by a Pd-catalyzed Suzuki coupling. Suitable Pd catalysts include $Pd(Ph_3)_4$ along with non-phosphine Pd catalysts, such palladium acetate. Other coupling procedures that may be used in the synthesis of flavonoid 13 include Stille coupling.

Prodrugs of flavonoid compounds can be prepared according to Scheme 4:

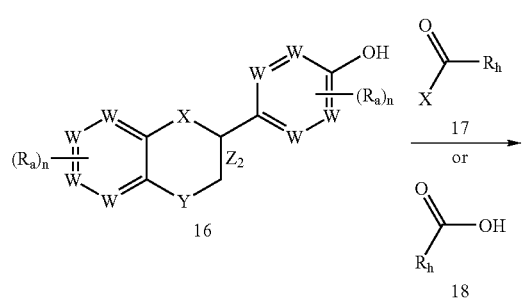

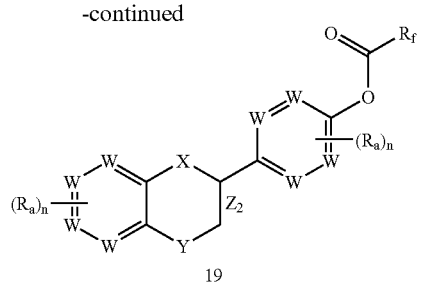

Prodrug esters 19 can be synthesized by treating phenol 16 with acid halide 17. Suitable acid halides include acid chlorides and bromides. Alternatively, esterification of phenol 16 with acid 18 in the presence of a carbodiimide, such as EDCl, affords ester 19.

The following compounds were obtained from commercially available sources: probucol (Sigma catalogue number P9672), resveratrol (Sigma, catalogue number R5010); taxol (USB catalogue number 10119; and rapamycin (Calbiochem catalogue number 553210). AG11067 was prepared according to known methods (Meng. et al., *J. Med. Chem.* 2004, 47, 6420-6432).

Abbreviations used herein denote the following compounds, reagents and substituents: acetic acid (AcOH); 2,2'-azobisisbbutyronitrile (AIBN); N-bromosuccinimide (NBS); N-tert-butoxycarbonyl (Boc); t-butyldimethylsilyl (TBDMS); m-chloroperoxybenzoic acid (mCPBA); dimethylaminopyridine (DMAP); dichloromethane (DCM); dimethylformamide (DMF); dimethylsulfoxide (DMSO); ethanol (EtOH); ethyl acetate (EtOAc); 1-ethyl-3-(3-dimethylaminopropyl)carbodiimide (EDCl); 1-hydroxybenzotriazole (HOBt); iodomethane (MeI); lithium hexamethyldisilazide (LHMDS); methanol (MeOH); methoxymethyl (MOM); tetrahydrofuran (THF).

EXAMPLES

Example 1

2-(4-Hydroxy-phenyl)-pyrano[2,3-b]pyridin-4-one

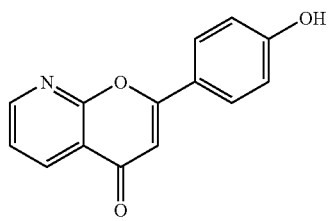 [SMILES: O=c1cc(-c2ccc(O)cc2)oc2ncccc12]

In a 500 mL dry round bottom flask with reflux condenser and magnetic stirrer was placed with 2-chloro-3-ethyl nicotinate (40.0 g, 215.5 mmol) in methanol (200 mL). $CH_3ONa$ in methanol (25%, 65 mL, 301.7 mmol) was added slowly and the reaction mixture was refluxed for 16 hours. The reaction was cooled to room temperature, quenched by addition of a saturated aqueous $NH_4Cl$ solution. The aqueous mixture was extracted with ethyl acetate. The combined organic layers were washed well with water, brine, dried over $Na_2SO_4$ and concentrated to give 35 g of 2-methoxy-3-methyl nicotinate with 97% yield. Sodium hydride (60% in oil, 9.21 g, 230.3 mmol) was added to a dry 500 mL round bottom flask followed by 100 mL DMF. 4-Methoxyacetophenone (31.45 g, 209.44 mmol) in 50 mL dry DMF was added drop-wise at 0° C. over 30 min. The reaction mixture was stirred for 1 h at room temperature. 2-Methoxynicotinic acid methyl ester (35 g, 209.44 mmol) was dissolved in 50 mL dry DMF and added slowly, keeping the temperature at 0° C. The mixture was stirred for 16 h at room temperature, then quenched by addition of a saturated aqueous NH$_4$Cl solution and diluted with water. The solid was filtered off, washed with water and dried to give 56.7 g diketo product in 95% yield.

The diketo compound (56.7 g, 198.9 mmol) was added to a 1 L round bottom flask together with pyridinium hydrochloride (345 g). The mixture was heated at 190° C. for 5 hours. The reaction mixture was cooled to room temperature and diluted with water. The solid was, isolated by filtration and purified by column chromatography using 5% methanol in CH$_2$Cl$_2$ to give 2-(4-hydroxy-phenyl)-pyrano[2,3-b]pyridin-4-one (23.25 g, 48.8% yield). MS (ES) m/z: 240.07 (M+1); $^{13}$C-NMR (DMSO-d$_6$): δ178.2, 164.2, 161.8, 160.8, 153.9, 136.3, 129.2, 123.2, 121.8, 116.8, 116.75, 116.74, 105.7.

Example 2

2-(4-Hydroxy-phenyl)-pyrano[3,2-b]pyridin-4-one

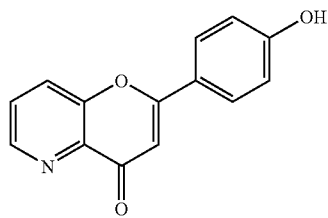 [SMILES: O=c1cc(-c2ccc(O)cc2)oc2cccnc12]

An example compound, (2-(4-hydroxy-phenyl)-pyrano[3,2-b]pyridin-4-one) was synthesized in the following way.

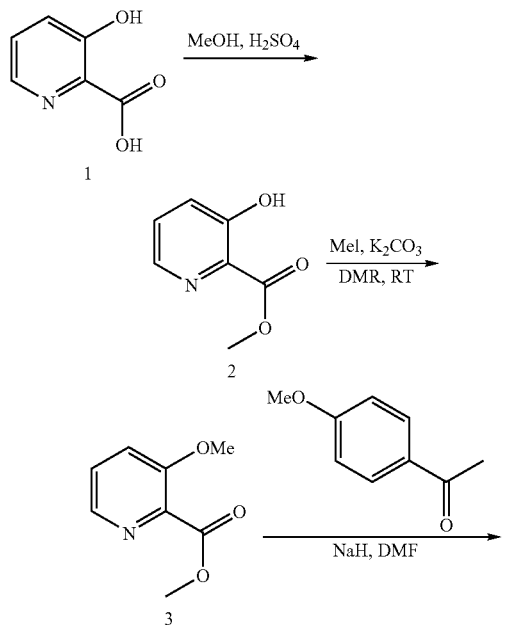

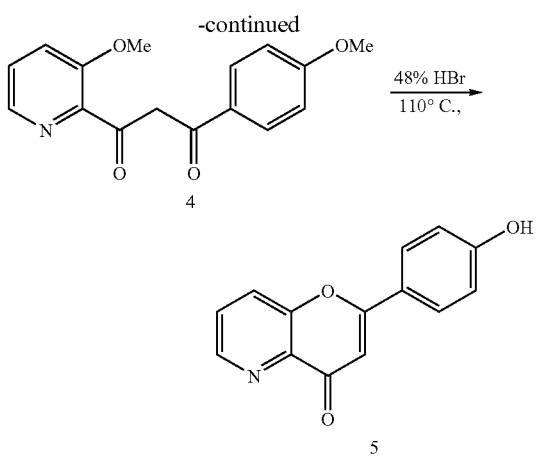

In a 500 mL round-bottomed flask fitted with a condenser and a magnetic stirrer were placed MeOH (250 mL), 3-hydroxypyridine-2-carboxylic acid 1 (10.0 g, 72 mmol) and concentrated H$_2$SO$_4$ (3 mL). The reaction mix was heated to 64° C. for 24 hours. The reaction mix was cooled to room temperature. The solvent was removed under reduced pressure; the residue was partitioned between ethyl acetate (150 mL) and water (20 mL). Solid sodium carbonate was added to adjust the pH to 6. The organic layer was separated, dried over Na$_2$SO$_4$, and concentrated to give crude 3.5 g of intermediate 2 (32% yield).

In a 50 mL round-bottomed flask fitted with a magnetic stirrer were placed intermediate 2 (3.5 g, 22.8 mmol), potassium carbonate (3.46 g, 25.0 mmol), methyl iodide (4.87 g, 34.3 mmol) and DMF (20 mL). The reaction mix was stirred for 18 h at room temperature under nitrogen. The reaction mix was diluted with ethyl acetate (30 mL) and water (10 mL). The organic layer was separated and aqueous layer was extracted with ethyl acetate. The combined organic extracts were dried over Na$_2$SO$_4$ and concentrated to give crude product, which was then purified by column chromatography using 30% ethyl acetate in hexane, to give 2.1 g of intermediate 3 (54% yield).

In 100 mL round-bottomed flask fitted with a magnetic stirrer were placed NaH (1.62 g of 60% suspension in mineral oil, 40 mmol) and a solution of intermediate 3 (3.5 g, 20 mmol) in anhydrous DMF (20 mL). The mixture was stirred for 15 min at room temperature under nitrogen. Then, a solution of 4-methoxyacetophenone (3.3 g, 22 mmol) was added via syringe. The reaction mix was stirred for overnight at room temperature. Then, a 10% aqueous solution of NaH$_2$SO$_4$ was used to adjust the pH to 7. The organic layer was separated and the aqueous layer was extracted with ethyl acetate. The combined organic extracts were dried over Na$_2$SO$_4$ and concentrated to give crude product, which was purified by column chromatography using 30% ethyl acetate in hexane, to give 4.68 g of intermediate 4 (80% yield).

In a 50 mL round-bottomed flask fitted with a magnetic stirrer were placed intermediate 4 (4.68 g, 16 mmol) and 45% HBr (25 mL). The reaction mix was refluxed for 3 h, then cooled to room temperature. Solid NaHCO$_3$ was used to adjust the pH to 7. Ethyl acetate (30 mL) was then added. The organic layer was separated and aqueous layer was extracted with ethyl acetate (2×30 mL). The combined organic extracts were dried over Na$_2$SO$_4$ and concentrated to give crude product, which was purified by column chromatography using 30% methanol in ethyl acetate to give 125 mg of 2-(4-hydroxy-phenyl)-pyrano[3,2-b]pyridin-4-one (3.2% yield); MS (ES) m/z: 240.09 (M+1), and 149.06.

Example 3

2-(4-Hydroxyphenyl)-pyrano[2,3-c]pyridin-one

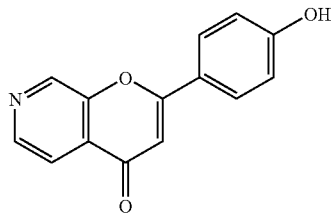 [SMILES: O=c1cc(-c2ccc(O)cc2)oc2cnccc12]

A 50 mL flask was charged with 5.0 g (0.0354 mol) 3-fluoroisonicotinic acid and thionyl chloride (3.88 mL, 0.053 mol). The mixture was heated to reflux for 1 h, then the excess thionyl chloride was evaporated under vacuum. Anhydrous methanol was added to the residue and the mixture was heated to reflux for one hour. The reaction mixture was poured into sodium bicarbonate solution and pH was adjusted to 7.0. The mixture was extracted with EtOAc and the organic layer was dry over sodium sulfate. The organic solvent was evaporated yielding the product (4.80 g, 88%). A 50 mL dry flask was charged with methyl 3-fluoroisonicotinate (3.50 g, 0.0227 mol), 4-methoxyacetophenone (3.60 g, 0.024 mol) and 10 mL dry DMF under nitrogen. Sodium hydride (1.82 g, 60% in oil) was added and the reaction was stirred for 30 min, then poured into ammonium chloride solution and extracted with EtOAc and dried over sodium sulfate. The solution was concentrated and the residue was pass through a column (EtOAc:hexane 1:3) to give the product (3.50 g, 54.0%). A 50 mL flask was charged with this product (0.5 g, 1.75 mmol) and pyridine hydrogen chloride (2.02 g, 17.5 mmol) and heat to 190° C. for 4 hours. The mixture was poured into a sodium bicarbonate solution and the solid was collected by filtration, washed with EtOAc and methanol to give 2-(4-hydroxyphenyl)-pyrano[2,3-c]pyridin-4-one as a yellow product (0.36 g, 86%). MS (ES) m/z: 240.90 (M+1), 239.89 (M); MP 294-296° C.

Example 4

2-(3-Fluoro-4-hydroxyphenyl)pyrano[2,3-b]pyridine-4-one

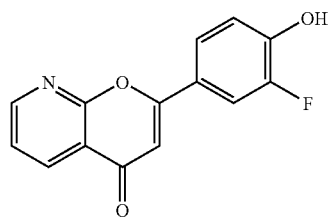

Methyl 2-methoxynicotinate was synthesized from ethyl 2-chloronicotinate with sodium methoxide as in Example 0.1. A 50 mL flask was charged with methyl 2-methoxynicotinate (2.50 g, 0.015 mol), 10 mL dry DMF and 60% NaH (0.745 g, 0.0186 mol) with magnetic stirring. 3'-Fluoro-4'-methoxyacetophenone (2.60 g, 0.0155 mol) in 6 mL anhydrous DMF was added over 5-10 min. After addition, the reaction mixture was stirred for 30 min. The mixture was poured into 50 mL NH₄Cl solution, the yellow solid was, filtered and further washed with water and purified by column chromatography (hexane:EtOAc 4:1) to get (3.0 g, 66.4%) of product. A 50 mL flask was charged with this product (0.8 g, 2.64 mmol) and pyridine hydrogen chloride (3.04 g, 26.4 mmol) and heated to 190° C. for 4 hours. The mixture was poured into sodium bicarbonate solution and the solid was collected by filtration, washed with EtOAc and MeOH and passed through a column (methanol:dichloromethane 1:4) to afford 400 mg of 2-(3-fluoro-4-hydroxyphenyl)pyrano[2,3-b]pyridine-4-one (59%). MS (ES) m/z: 257.85 (M); MP 267-268° C.

Example 5

2-(4-Hydroxy-3-methylphenyl)-4H-pyrano[2,3-b]pyridine-4-one

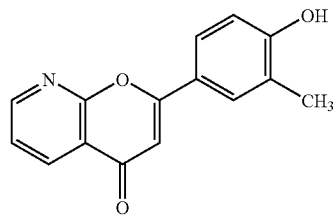 [SMILES: Cc1cc(-c2cc(=O)c3cccnc3o2)ccc1O]

Methyl 2-methoxynicotinate was synthesized from ethyl 2-chloronicotinate with sodium methoxide as described in Example 1. A 100 mL dry flask was charged with 2-methylanisole (7.92 g, 65 mmol), acetyl chloride (5.1 mL, 71 mmol), aluminum chloride (9.45 g, 71 mmol) and 40 mL of anhydrous dichloromethane. The reaction mixture was kept at reflux for 2 h, then poured into 15 mL of HCl (3 N) and extracted with 100 mL ether. The organic layer was further washed with sodium bicarbonate to pH 6-7, then further washed with brine and dried over sodium sulfate. The solvent was evaporated and the residue was dried under high vacuum to yield the intermediate (10.0 g, 93.85%). A 100 mL dry flask was charged with methyl 2-methoxynicotinate (2.50 g, 15 mmol), 10 mL anhydrous DMF and NaH (0.9 g, 22.5 mmol, 60% in oil). The intermediate (2.58 g, 15.7 mmol) in 3 mL anhydrous DMF was added and the reaction was stirred for 2 hours. The mixture was poured into 120 mL of water with 3 mL AcOH. The yellow solid was further wash with water and passed through a column (hexane:EtOAc 3:1) to give the methoxy intermediate (3.4 g, 75.7%). A 50 mL flask was charged with the methoxy intermediate (1.0 g, 3.3 mmol) and pyridine, hydrogen chloride (4.0 g, 33 mmol) and heated to 190° C. for 3 hours. The mixture was poured into a sodium bicarbonate solution and the solid was collected by filtration, washed with EtOAc and MeOH (20 mL each) to give 2-(4-hydroxy-3-methylphenyl)-4H-pyrano[2,3-b]pyridine-4-one (0.58 g, 69.4%). MS (ES) m/z: 254.0 (M+1); MP 300-302° C.

Example 6

2-(4-Hydroxyphenyl)-4H-pyrano[3,2-c]pyridin-4-one

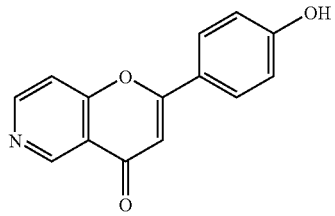 [SMILES: O=c1cc(-c2ccc(O)cc2)oc2ccncc12]

A solution of 4-chloropicolinic acid (3.09g, 19.04 mmol) in EtOH (100 mL) was mixed with $H_2SO_4$ (conc., 5 mL) and was stirred at reflux for 48 hours. The reaction mixture was cooled to room temperature and neutralized with NaOH (1 N) to adjust pH=8-9. The mixture was extract with dichloromethane (3×100 mL) and concentration to afforded ethyl 4-ethoxypicolinate (3.44 g, 93%).

To a solution of ethyl 4-ethoxypicolinate (3.44 g, 17.43 mmol) and 4-methoxy acetophenone (2.62 g, 17.43 mmol) in THF (100 mL) and DMSO (50 mL) was added NaH (1.4 g, 34.80 mmol). The resulting mixture was stirred at 95° C. for 6 hours. The reaction mixture was cooled to room temperature and quenched with water (100 mL). The mixture was extract with EtOAc (3×150 mL) and concentration to a yellow solid. The solid was washed with hexanes to afford the diketone (3.6 g, 69%).

The diketone (1 g, 3.34 mmol) was mixed with pyridine hydrochloride (10 g). This mixture was stirred at 190° C. under nitrogen for 12-hours. The mixture was then diluted with EtOAc (30 mL) and poured into a beaker of 200 mL ice water. NaOH (1 N) was used to adjust the pH to 9. The solid was then filtered off and washed with water, hexanes, dichloromethane, EtOAc sequentially to afford the brownish solid 2-(4-hydroxyphenyl)-4H-pyrano[3,2-c]pyridin-4-one (0.39 g, 49%). MS (ES) m/z: 240.92 (M+1), 239.89 (M); MP 306-308° C.

Example 7

2-(3-Chloro-4-hydroxyphenyl)-4H-pyrano[2,3-b]pyridine-4-one

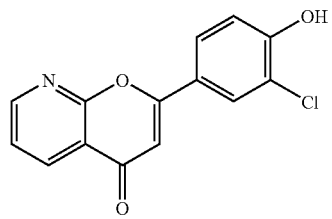 [SMILES: O=c1cc(-c2ccc(O)c(Cl)c2)oc2ncccc12]

Sodium methoxide (18 mL, 25 wt % in methanol) was added slowly to a solution of ethyl-2-chloronicotinate (11.134 g 60 mmol) in 60 mL anhydrous methanol. The reaction mixture was stirred under reflux for 15 h, then cooled to room temperature. Methanol was removed in vacuo. The residue was dissolved in EtOAc (200 mL) and saturated aqueous ammonium chloride (50 mL) was added. The organic layer was separated and dried over anhydrous $Na_2SO_4$. The solvent was removed to give ethyl-2-methoxynicotinate (8.58 g, 79%). Sodium hydride (60% in mineral oil, 0.48 g, 12 mmol) was dissolved in anhydrous DMF (10 mL). A solution of 3'-chloro-4'-methoxy acetophenone (1.85 g, 10 mmol) in anhydrous DMF (5 mL) was added drop-wise at 0° C. under nitrogen. The mixture was stirred at 0° C. for 5 min. and then at room temperature for 30 min. The mixture was cooled to 0° C. A solution of ethyl 2-methoxy nicotinate (1.81 g, 10 mmol) in anhydrous DMF (5 mL) was added slowly. The ice bath was removed and the mixture was stirring at room temperature under nitrogen for 20 hours. Water (20 mL) was added and the mixture was extracted with EtOAc (2×100 mL). The combined organic layers were washed with brine and dried over anhydrous $Na_2SO_4$. Removal of solvent gave a dark colored solid. Triturating with ether gave a yellow solid (1.64 g, 51%). The yellow solid (1.36 g, 4.21 mmol) and pyridinium hydrochloride (7.3 g, 63.2 mmol) were mixed together and stirred at 190° C. for 2 h, then cooled to room temperature. Water (100 mL) was added. The solid was separated by filtration, washed with water and dried under vacuum. The crude compound was purified by column chromatography (Silica Gel 230-400 mesh; 5% methanol in dichloromethane as an eluent to afford 2-(3-chloro-4-hydroxyphenyl)-4H-pyrano[2,3-b]pyridine-4-one (0.385 g, 33% yield) as yellow solid. MS (ES) m/z: 275.94+273.92 (two isotopes of M); MP 259-262° C.

Example 8

2-(4-Hydroxy-3-methoxyphenyl)-4H-pyrano[2,3-b]pyridine-4-one

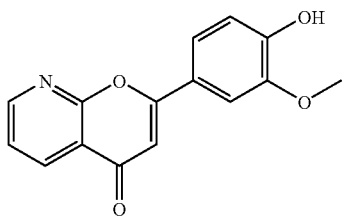 [SMILES: COc1cc(-c2cc(=O)c3cccnc3o2)ccc1O]

A solution of ethyl 2-chloronicotinitate (6.0 g, 0.0323 mol) in anhydrous methanol (10 mL) at room temperature was added sodium methoxide (10 mL, 25% in methanol). The reaction mixture was stirred for half hour then heated to reflux for one hour. The mixture was poured into water and extracted with ethyl acetate and the organic layer was washed with water until neutral, dried over sodium sulfate, and concentrated to give methyl 2-methoxynicotinitate (5.2 g, 96.3%).

A 100 mL dry flask was charged with acetovanillone (4.16 g, 0.025 mol) and anhydrous DMF (10 mL). Sodium hydride (1.05 g, 0.0263 mol, 60% in mineral oil) was added and the reaction mixture was stirred at room temperature followed by the dropwise addition of benzyl bromide (3.1 mL, 0.0263 mol). The reaction was carried out at room temperature for 2 h, then poured into water. Ethyl acetate (150 mL) was used to extract out the compound and the organic layer was washed with water (2×100 mL), brine, dried over sodium sulfate, and concentrated to give the benzyl intermediate (6.21 g, 966%), which was subsequently used without further purification.

A 100 mL dry flask was charged with methyl 2-methoxynicotinitate (2.2 g, 0.0131 mol), the benzyl intermediate (3.37 g, 0.0131 mol) and anhydrous DMF (10 mL). Sodium hydride (0.524 g, 0.0131 mol, 60% in mineral oil) was added and the reaction mixture was stirred for 2 hours at room temperature. The reaction mixture was poured into water and extracted with ethyl acetate (150 mL). The organic layer was washed with water (2×100 mL), brine (100 mL), dried over sodium sulfate, and concentrated to give the intermediate (5.0 g, 97.6%). This intermediate (4.0 g, 0.0102 mol) and pyridine hydrochloride (12.0 g, 0.102 mol) were mixed and heated to 170-190° C. for 20 min. The reaction mixture was cooled and poured into water (100 mL). The mixture was extracted with ethyl acetate (3×200 mL), and the combined organic layers were washed with brine (×3×100 mL), dried over sodium sulfate, and concentrated. The solid was further purified by refluxing with methanol (40 mL). The solution was cooled and filtered to yield 2-(4-hydroxy-3-methoxyphenyl)-4H-pyrano[2,3-b]pyridine-one (250 mg, 9.1%). MS (ES) m/z: 270.92, 269.91; MP 253-255° C.

Example 9

2-(4-Methoxyphenyl)-4H-pyrano[2,3-b]pyridine-4-one

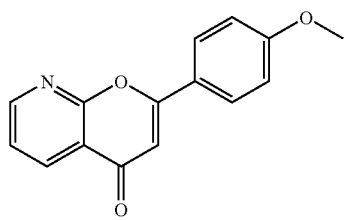 [SMILES: COc1ccc(-c2cc(=O)c3cccnc3o2)cc1]

In a 500 mL dry round bottom flask with reflux condenser and magnetic stirrer was placed with 2-chloro-3-ethyl nicotinate (40.0 g, 215.5 mmol) in methanol (200 mL), and sodium methoxide (65 mL, 301.7 mmol, 25% in methanol) was added slowly and the reaction mixture was refluxed for 16 hours. The reaction mixture was cooled to room temperature and the reaction was quenched by addition of saturated aqueous NH₄Cl solution, followed by extraction with ethyl acetate. The combined organic layers were washed well with water, brine, dried over Na₂SO₄ and concentrated to give 2-methoxy-3-methyl nicotinate (35 g, 97%). To a dry 500 mL round bottom flask was added NaH (9.21 g 230.3 mmol, 60% in mineral oil) in DMF (100 mL). 4-Methoxyacetophenone (31.45 g, 209.44 mmol) in dry DMF (50 mL) was added dropwise at 0° C. over 30 min. The reaction mixture was stirred for 1 h at room temperature. Then 2-methoxynicotinic acid methyl ester (35 g, 209.44 mmol) dissolved in dry DMF (50 mL) was added slowly on cooling. The mixture was stirred for 16 h at room temperature. The reaction was quenched by addition of saturated NH₄Cl solution and diluted with water. The solid was filtered off, washed with water and dried to give the diketo product (56.7 g, 95%). Polyphosphoric acid (8.0 g) was heated at 90° C. and the diketo compound (1.0 g, 3.50 mmol) was added slowly and heated at 90° C. for 1 hour. The reaction mixture was cooled to room temperature and diluted with water. The solid was isolated by filtration, washed with water and dried to give 2-(4-methoxyphenyl)-4H-pyrano[2,3-b]pyridine-4-one (570 mg, 64%). MS (ES) m/z: 254.89 (M+1), 253.90 (M); MP 269-270° C.

Example 10

2-(4-(2-Hydroxyethoxy)phenyl)-4H-pyrano[2,3-b]pyridine-4-one

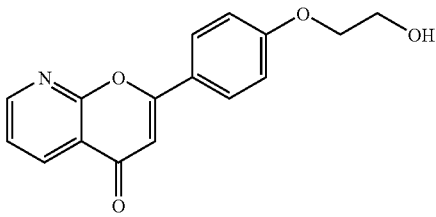 [SMILES: O=c1cc(-c2ccc(OCCO)cc2)oc2ncccc12]

In a 100 mL dry round bottom flask with reflux condenser and magnetic stirrer was placed 2-(4-hydroxy-phenyl)-pyrano[2,3-b]pyridin-4-one (1.0 g, 4.18 mmol) in EtOH (10 mL) and acetonitrile (50 mL). 2-Chloroethanol (2.05 g, 25.0 mmol) was added slowly and the reaction mixture was refluxed for 48 hours. The reaction mixture was cooled to room temperature and concentrated under reduced pressure. The crude product was purified by column chromatography, using 2% MeOH in dichloromethane to afford 2-(4-(2-hydroxyethoxy)phenyl)-4H-pyrano[2,3-b]pyridine-4-one (380 mg, 32% yield). MS (ES) m/z: 284.94 (M+1), 283.95 (M); MP 157-159° C.

Example 11

2-(5-Hydroxy-pyridin-2-yl)chromen-4-one

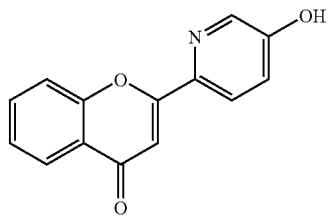

An example compound, 2-(5-hydroxy-pyridin-2-yl)-chromen-4-one was synthesized in the following way. In a 100 mL round-bottomed flask fitted with a condenser and a magnetic stirrer were placed 5-amino-2-cyano pyridine (1.0 g, 8.4 mmol), concentrated H₂SO₄ (4.2 mL), water (15 mL) and the mixture was cooled to 0° C. A solution of NaNO₂ (636 mg, 9.22 mmol) in water (5.7 mL) was added slowly at 0° C. Then, the reaction mix was stirred for 30 min. at 0° C. The reaction mix was poured into a boiling mixture of water (11 mL) and H₂SO₄ (1 mL) and stirred for 30 min. The mixture was cooled and extracted with ethyl acetate. The organic layer was washed with water, dried and concentrated to give 2 cyano-5-hydroxy pyridine (900 mg, 89%).

To a mixture of 2-cyano-5-hydroxy pyridine (200 mg, 1.66 mmol), DMF (10 mL) and K₂CO₃ (253 mg, 1.83 mmol), was added MeI (354 mg, 2.49 mmol) at room temperature and the reaction mix was stirred for 24 h at room temperature. The reaction mix was poured into water and extracted with ethyl acetate. The organic layer was separated, washed with water, dried and concentrated to give 2-cyano-5-methoxy pyridine (175 mg, 78% yield).

The 2-cyano-5-methoxy pyridine (170 mg, 1.26 mmol) was taken into 6N HCl (4 mL) and refluxed for 16 hours. The reaction mix was cooled to room temperature and diluted with water, neutralized, and extracted with ethyl acetate. The organic layer was washed with water, then brine, and was dried and concentrated to give crude 5-methoxy-2-nicotinic acid (290 mg).

In a 100 mL round-bottomed flask fitted with a condenser and a magnetic stirrer were placed 2'-hydroxy acetophenone (3.56 g, 26.1 mmol), 5-methoxy-2-nicotinic acid (4.0 g, 26.1 mmol) and pyridine (50 mL). POCl$_3$ (4 g, 26.1 mmol) was added slowly with cooling. Then, the reaction mix was stirred for 24 h at room temperature under nitrogen. The reaction mix was poured into ice-water and was extracted with ethyl acetate. The organic layer was washed with water, dried, and concentrated to give product (1.76 g, 24% yield). To a solution of this product (1.76 g, 6.5 mmol) in THF (30 mL), was added potassium t-butoxide (952 mg, 7.8 mmol) and the reaction mix was stirred for 24 h at room temperature under nitrogen. The reaction mix was poured into a saturated solution of NH$_4$Cl. The organic layer was separated, washed with water, dried and concentrated to give crude product, which was purified by using column chromatography using 50% ethyl acetate in hexane to give the diketone (870 mg, 49% yield). The diketone compound (870 mg, 3.2 mmol) was taken into a mixture of 48% HCl (1 mL) and acetic acid (10 mL) and heated at 100° C. for 1 hours. The reaction mix was cooled to room temperature, diluted with water, and extracted with ethyl acetate. The organic layer was washed with water, then brine, and was dried and concentrated to give the cyclized product (794 mg, 98%). A mixture of the 4'-methoxy flavone (790 mg, 3.12 mmol) in Hi (10 mL) and acetic acid (4 mL) was heated at reflux for 6 hours. The reaction mix was cooled to room temperature, diluted with water, neutralized, and extracted with ethyl acetate to give crude product. This was purified by column chromatography using 5% methanol in dichloromethane to give 2-(5-Hydroxy-pyridin-2-yl)-chromen-4-one (270 mg, 36%); MS (ES) m/z: 240.09 (M+1).

Example 12

2-Pyridin-4-yl-chromen-4-one

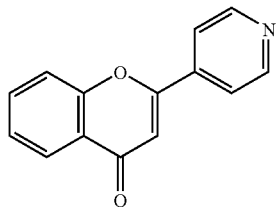 [SMILES: O=c1cc(-c2ccncc2)oc2ccccc12]

2-Hydroxyacetophenone (1.36 g, 10 mmol) and isonicotinyl chloride hydrochloride (1.78 g, 10 mmol) were dissolved in 20 mL anhydrous pyridine and stirred at room temperature for 15 h under nitrogen. Water (20 mL) was added and neutralized to pH 6 with 4N HCl. The formed solid was filtered off, washed with water and dried to give isonicotinic acid-2-acetyl phenyl ester as a white powder (2.32 g, 96%). To a solution of isonicotinic acid-2-acetyl phenyl ester (2.2 g, 9.12 mmol) in 20 mL anhydrous pyridine was added powdered potassium hydroxide (1.54 g, 27.36 mmol) and stirred at room temperature for 15 h under nitrogen. Water (50 mL) was added and the pH was adjusted to pH 6 with 4N HCl. The solid formed was filtered off, washed with water and dried to give a yellow powder (0.66 g). The aqueous phase was extracted with EtOAc. The organic layer was washed with brine, dried over anhydrous Na$_2$SO$_4$, and concentrated to give a yellow solid (1.32 g, 60%). The compound (0.64 g, 2.654 mmol) was suspended in 6 mL glacial AcOH. Three drops of conc. HCl was added and the mixture was stirred at 110° C. for 3 hours. The mixture was cooled to room temperature. Water (20 mL) was added and the mixture was neutralized to pH 6-7 with a 2 N NaOH solution. The white precipitate formed was filtered off, washed with water and dried under vacuum to give 2-pyridin-4-yl-chromen-4-one (0.56 g, 94.5%). MS (ES) m/z: 224.89 (M+1), 223.92 (M); MP 144-145° C.

Example 13

2-(6-Hydroxypyridin-3-yl)-chromen-4-one

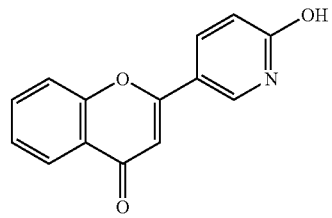 [SMILES: O=c1cc(-c2ccc(O)nc2)oc2ccccc12]

In a 100 mL round-bottomed flask fitted with condenser and magnetic stirrer were placed 2'-hydroxy-acetophenone (2.0 g, 14.69 mmol), 2-methoxy-5-pyridine carboxylic acid (2.0 g, 14.69 mmol) and pyridine (20 mL). POCl$_3$ (2.25 g, 14.69 mmol) was added slowly on cooling. The reaction mixture was stirred for 24 h at room temperature under nitrogen. The reaction mixture was poured into ice-water and extracted with EtOAc. The organic layer was washed with water, dried and concentrated to give product (2.82 g, 70%). To a solution of this product (2.8 g, 10.33 mmol) in THF (50 mL) was added potassium t-butoxide (1.51 g, 12.4 mmol) and the reaction mixture was stirred for 3 h at room temperature under nitrogen. The reaction mixture was poured into a saturated aqueous solution of NH$_4$Cl. The organic layer was separated, washed with water, dried and concentrated to give crude diketone (2.8 g, 99%). The diketone (2.8 g, 10.33 mmol) was dissolved in a mixture of 36% HCl (2 mL) and AcOH (25 mL) and heated at 100° C. for 1 hours. The reaction mixture was cooled to room temperature, diluted with water and extracted with EtOAc. The organic layer was washed with water, brine, dried and concentrated to give the crude cyclized product (1.96 g, 74%). A mixture of the cyclized product (500 mg, 1.97 mmol) and pyridinium hydrochloride (5 g) was heated at 190° C. for 1 hour. The reaction mixture was cooled to room temperature, diluted with water, neutralized with NaHCO$_3$ and filtered to give 2-(6-hydroxypyridin-3-yl)-chromen-4-one (480 mg, 98%). MS (ES) m/z: 240.92 (M+1), 239.89 (M); MP 296-297° C.

Example 14

2-(4-Hydroxy-phenyl)-1H-quinolin-4-one

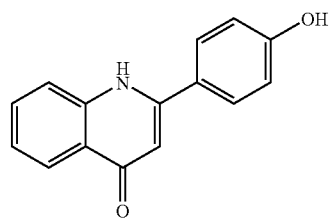 [SMILES: O=c1cc(-c2ccc(O)cc2)[nH]c2ccccc12]

In a 50 mL round-bottomed flask fitted with a condenser and a magnetic stirrer were placed 2-amino acetophenone (1.0 g, 7.4 mmol), THF (15 mL) and Et₃N (2.39 g, 23.6 mmol). To the solution, p-methoxy benzoyl chloride (1.32 g, 7.76 mmol) in THF (15 mL) was added slowly at 0° C. and stirred for 30 min at 0° C. Then the reaction mix was stirred for 24 h at room temperature under nitrogen. The reaction mix was poured into ice-water. The precipitate was collected and the crude product was purified by column chromatography using 25% ethyl acetate in hexane to give 1.865 g of product (93% yield). To a suspension of this product (0.865 g, 3.2 mmol) in t-butanol (12 mL), was added potassium t-butoxide (1.57 g, 12.8 mmol) and the reaction mix was heated to ~70° C. for ~24 h under nitrogen. The mixture was then cooled to room temperature and poured into 30 mL of a saturated solution of NH₄Cl. The solids were collected and purified by column chromatography using 10% methanol in dichloromethane to give 398 mg of product (49% yield). This methoxy compound (375 mg, 1.5 mmol) was taken into 48% HBr (15 mL) and refluxed for 16 hours. The solvent was removed at reduced pressure. The solids were taken into water and neutralized with NaHCO₃. Solids were collected and purified by column chromatography using 5% methanol in dichloromethane to give 350 mg of product (98% yield). MS (ES): m/z: 238.1 (M+1).

Example 15

4-Isoquinolin-3-yl-phenol

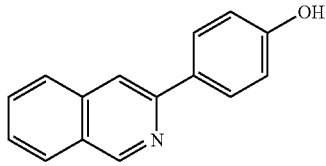 [SMILES: Oc1ccc(-c2cc3ccccc3cn2)cc1]

To a solution of 2-bromobenzaldehyde (1.85 g, 10 mmol) and 4-methoxyphenyl acetylene (1.58 g, 12 mmol) in 40 mL of triethylamine were added dichlorobis(triphenylphosphine)palladium(II) (140 mg, 2 mol %) and copper(I) iodide (20 mg, 1 mol %). The reaction mixture was heated at 50° C. under nitrogen for 3 hours. The reaction mixture was cooled to room temperature and the ammonium salt was removed by filtration. The filtrate was concentrated under reduced pressure. Purification of the crude compound by column chromatography (SilicaGel 230-400 mesh; 10% ethyl acetate in hexanes as eluent) afforded of 2-(4-methoxy phenylethynyl)benzaldehyde (2.1 g, 89%).

2-(4-Methoxy phenylethynyl)benzaldehyde (2.06 g, 8.73 mmol) and t-butylamine (3.83 g, 52.4 mmol) were stirred under nitrogen for 24 h at room temperature. The resulting mixture was extracted with ether and the organic layer was dried over anhydrous Na₂SO₄, concentrated to give the imine (2.4 g, 94%) which was used in the next step without further purification. To a solution of this imine (2.39 g, 8.2 mmol) in 100 mL anhydrous DMF was added (0.156 g, 0.82 mmol) copper(I) iodide and flushed with nitrogen. The reaction mixture was heated at 100° C. for 4 hours. The mixture was cooled to room temperature, and diluted with ether (200 mL). The organic layer was washed with saturated aqueous ammonium chloride (3×100 mL). The organic layer was dried over anhydrous Na₂SO₄ and concentrated to give the crude compound as a dark colored solid. Purification by column chromatography (SilicaGel 230-400 mesh; 10% ethylacetate in hexanes as eluent) afforded 3-(4-methoxyphenyl)isoquinoline (1.064 g, 55%) as a white solid. The 3-(4-methoxyphenyl)isoquinoline (1.05 g, 4.47 mmol) was suspended in 30 mL hydroiodic acid and 12 mL of acetic acid was added. The reaction mixture was stirred at 110° C. for 2 h, then cooled to room temperature. The precipitate formed was filtered off, washed with acetic acid (2×5 mL) and dried under vacuum to give a yellow solid. The crude compound was purified by triturating with 5% methanol in ether to give 4-isoquinolin-3-yl-phenol (0.83 g, 84%) as a white powder. MS (ES) m/z: 222.89 (M+1), 221.86 (M); MP 218-219° C.

Example 16

7-(3-Fluoro-4-hydroxyphenyl)-6-methyl-1,6-naphthyridin-5(6H)-one

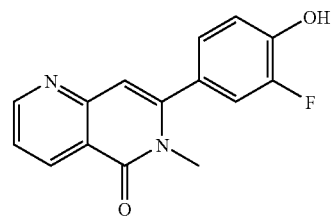 [SMILES: Cn1c(-c2ccc(O)c(F)c2)cc2ncccc2c1=O]

A suspension of 2-methyl nicotinic-acid (1.5 g, 10.94 mmol) in DCM (30 mL), triethylamine (1.16 g, 11.48 mmol) and oxalyl chloride (2.77 g, 21.87 mmol) were stirred at room temperature for 16 hours. The solvent and excess of oxalyl chloride were removed at reduced pressure. The solid was dissolved in DCM (10 mL) and methylamine hydrochloride (1.02 g, 32.81 mmol) was added on cooling followed by stirring at room temperature for 4 hours. The solvent was removed and the crude product was purified by chromatography by using 5% MeOH in DCM to give 1.4 g of the amide product (95%). To a solution of the amide (1.35 g, 8.99 mmol) in THF (25 mL), was slowly added n-butyl lithium (8.3 mL, 20.68 mmol, 2.5 M solution in hexane) under nitrogen with cooling (ice-salt bath), maintaining the temperature below 20° C. After addition, the mixture was stirred for 1 h at 0° C. The mixture was cooled to −50° C. and a solution of 4-methoxy-3-fluoro benzonitrile (1.63 g, 10.79 mmol) in THF (10 mL) was added quickly. The cooling bath was removed and the mixture was allowed to warm to room temperature. Saturated NH₄Cl solution was added under cooling, and the layers were separated. The organic layer was washed with water, brine, and dried over Na₂SO₄. After concentration, the crude product was purified by chromatography using 5% MeOH in DCM to give 918 mg of the enamine (34%). To a suspension of the enamine (400 mg, 1.33 mmol) in EtOH (15 mL) was added conc. HCl (2 mL). The mixture was heated at 80° C. for 2 hours. The reaction mixture was cooled to room temperature and the solvent was removed to give 400 mg of crude methoxy compound (94%). In a 50 mL flask were placed the methoxy compound (400 mg, 1.40 mmol) and pyridinium hydrochloride (6 g), followed by heating of the mixture at 190° C. for 4 hours. The flask was then cooled to room temperature, diluted with water, neutralized with NaHCO₃ and the solid was filtered to afford 160 mg of 7-(3-fluoro-4-hydroxyphenyl)-6-methyl-1,6-naphthyridin-5(6H)-one (42%). MS (ES) m/z: 271.97 (M+1), 270.96 (M); MP 182-184° C.

Example 17

2-Fluoro-4-(5-methoxy-1-(methylamino)isoquinolin-3-yl)phenol

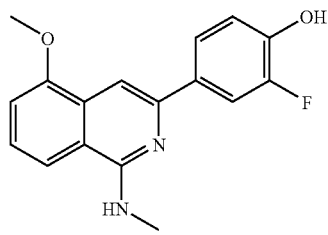 [SMILES: CNc1nc(-c2ccc(O)c(F)c2)cc2c(OC)cccc12]

To a suspension of 2-methyl-3-methoxy benzoic acid (2.0 g, 12.03 mmol) in CH$_2$Cl$_2$ (30 mL), oxalyl chloride (3.05 g, 24.07 mmol) was added and stirred at room temperature for 16 hours. The solvent and excess of oxalyl chloride were removed at reduced pressure. The solid was dissolved in CH$_2$Cl$_2$ (10 mL) and methyl amine (1.12 g, 36.1 mmol) was added on cooling and the mixture was stirred at room temperature for 4 hours. The solvent was removed and the crude product was purified by chromatography using 5% methanol in CH$_2$Cl$_2$ to give the amide product (1.67 g, 78%). To a solution of the amide (946 mg, 5.28 mmol) in THF (20 mL) was added n-butyl lithium (4.85 mL, 12.14 mmol, 2.5 M solution in hexane) was added slowly under nitrogen with cooling (ice-salt bath) maintaining temperature below −20° C. After completion of addition, the mixture was stirred for 1 h at 0° C., then cooled to −50° C. and a solution of 4-O-TBDMS-3-fluoro benzonitrile (1.46 g, 5.8 mmol) in THF (10 mL) was added quickly. The cooling bath was removed and the reaction mixture was allowed to warm to room temperature. Saturated NH$_4$Cl solution was added under cooling. The organic layer was washed with water, brine, dried over Na$_2$SO$_4$ and concentrated to give the crude product, which was purified by chromatography using 5% methanol in CH$_2$Cl$_2$, to give two products: an enamine (260 mg) and a cyclized product (450 mg). To a suspension of the enamine (400 mg, 1.33 mmol) in ethanol (15 mL), conc. HCl (2 mL) was added and heated at 80° C. for 2 hours. The reaction mixture was cooled to room temperature and the solvent was removed and neutralized by NaHCO$_3$ to give 2-fluoro-4-(5-methoxy-1-(methylamino)isoquinolin-3-yl)phenol (150 mg, 83%). MS (ES) m/z: 300.01 (M+1), 299.00 (M); MP 185-187° C.

Example 18

3-(3-Fluoro-4-hydroxyphenyl)-5-methoxyisoquinolin-1(2H)-one

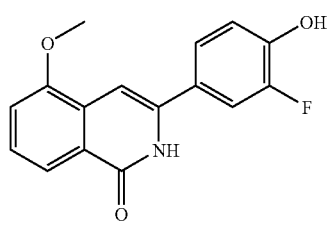 [SMILES: COc1cccc2c(=O)[nH]c(-c3ccc(O)c(F)c3)cc12]

To a suspension of 2-methyl-3-methoxy benzoic acid (2.0 g, 12.03 mmol) in DCM (30 mL), oxalyl chloride (3.05 g, 24.07 mmol) was added and stirred at room temperature for 16 hours. The solvent and excess of oxalyl chloride were removed at reduced pressure. The solid was dissolved in DCM (10 mL) and methyl amine (1.12 g, 36.1 mmol) was added on cooling and the mixture was stirred at room temperature for 4 hours. The solvent was removed and the crude product was purified by chromatography using 5% MeOH in DCM to give the amide product (1.67 g, 78%). To a solution of the amide (946 mg, 5.28 mmol) in THF (20 mL) was added n-butyl lithium (4.85 mL, 12.14 mmol, 2.5 M solution in hexane) was added slowly under nitrogen with cooling (ice-salt bath) maintaining temperature below −20° C. After completion of addition, the mixture was stirred for 1 h at 0° C., then cooled to −50° C. and a solution of 4-O-TBDMS-3-fluoro benzonitrile (1.46 g, 5.8 mmol) in THF (10 mL) was added quickly. The cooling bath was removed and the reaction mixture was allowed to warm to room temperature. Saturated NH$_4$Cl solution was added under cooling. The organic layer was washed with water, brine, dried over Na$_2$SO$_4$ and concentrated to give the crude product, which was purified by chromatography using 5% MeOH in DCM, to give two products: an enamine (260 mg) and a cyclized product (450 mg). To a suspension of the cyclized product (450 mg, 1.1 mmol) in EtOH (15 mL), conc. HCl (2 mL) was added and heated at 60° C. for 3 hours. The reaction mixture was cooled to room temperature and the solvent was removed and purified by chromatography using 5% MeOH in DCM to give 85 mg of product (26%). MS (ES) m/z: 286.11; MP 289-291° C.

Example 19

3-(4-Hydroxyphenyl)-6,8-dimethoxyisoquinolin-1(2H)-one

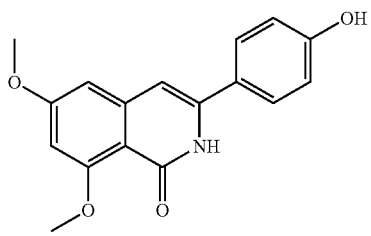 [SMILES: COc1cc(OC)c2c(=O)[nH]c(-c3ccc(O)cc3)cc2c1]

To a suspension of 2-methyl-4,6-dimethoxy benzoic acid (2.8 g, 14.27 mmol) in CH$_2$Cl$_2$ (30 mL), oxalyl chloride (3.62 g, 28.54 mmol) was added and the mixture was stirred at room temperature for 16 hours. The solvent and excess of oxalyl chloride were removed at reduced pressure. The solid was dissolved in CH$_2$Cl$_2$ (10 mL) and methyl amine hydrochloride (1.33 g, 42.81 mmol) was added on cooling and the mixture was stirred at room temperature for 4 hours. The solvent was removed and the crude product was purified by chromatography by using 5% methanol in CH$_2$Cl$_2$, to give 1.3 g of the amide intermediate in 43% yield. To a solution of the amide intermediate (1.29 g, 6.16 mmol) in THF (30 mL), n-butyl lithium (5.6 mL, 14.18 mmol, 2.5 M solution in hexane) was added slowly under nitrogen with cooling (ice-salt bath) maintaining the temperature below 20° C. The mixture was stirred for 1 h at 0° C., then cooled to −50° C. and a solution of 4-O-TBDMS-benzonitrile (1.58 g, 6.78 mmol) in THF (10 mL) was added quickly. The cooling bath was removed and allowed to warm to room temperature and stirred for 16 h at room temperature. Saturated aqueous NH$_4$Cl solution was added with cooling, and the layers were separated. The organic layer was washed with water, brine, dried over Na$_2$SO$_4$ and concentrated to give the crude intermediate, which was purified by chromatography using 5% methanol in CH$_2$Cl$_2$, to give two products (1) 678 mg of isoquinoline in 26% yield and (2) 780 mg of quinolone product in 27% yield. To a suspension of the above quinolone product (2) (780 mg, 1.65 mmol) in ethanol (20 mL), conc. HCl (2 mL) was added and the mixture was heated at 70° C. for 2 hours. The reaction mixture was cooled to room temperature and the solvent was removed and purified by chromatography using 5% methanol in CH$_2$Cl$_2$ to give 3-(4-hydroxyphenyl)-6,8-dimethoxyisoquinolin-1(2H)-one (215 mg, 44%). MS (ES) m/z: 297.93 (M); MP 245-247° C.

Example 20

2-(4-Hydroxy-phenyl)-[1,4]naphthoquinone

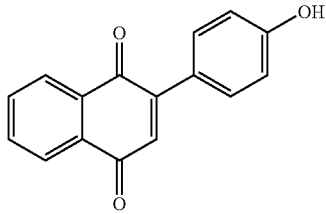 [SMILES: O=C1C=C(c2ccc(O)cc2)C(=O)c2ccccc21]

An example compound, 2-(4-hydroxy-phenyl)-[1,4]naphthoquinone was synthesized in the following way. To a mixture of 2-bromo-1,4-naphthoquinone (1.0 g, 4.22 mmol), 4-hydroxy phenyl boronic acid (640 mg, 4.64 mmol), potassium phosphate (3.135 g, 14.76 mmol), tri cyclo hexyl phosphine (118 mg, 0.422 mmol), toluene (20 mL) and water (1 mL) was added palladium acetate (47 mg, 0.21 mmol) under nitrogen. The reaction mix was heated to ~100° C. for 3 h and then cooled to room temperature. Water was added and the mixture was extracted with ethyl acetate. The organic layer was separated, washed with water, brine, dried and concentrated to give crude product, which was purified by column chromatography, using 10% ethyl acetate in hexane to give (480 mg, 45% yield) of 2-(4-Hydroxy-phenyl)-[1,4]naphthoquinone; MS (ES) m/z, 251.03 (M+1).

Example 21

3-(4-Hydroxyphenyl)-2H-isoquinolin-1-one

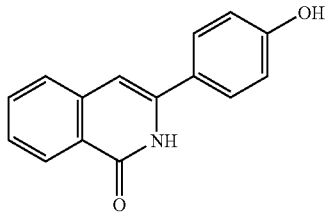 [SMILES: O=c1[nH]c(-c2ccc(O)cc2)cc2ccccc12]

To a solution of n-methyl-o-toluamide (2.0 g, 13.4 mmol) in THF (30 mL), n-butyl lithium (12.3 mL, 30.8 mmol, 2.5 M solution in hexane) was added slowly under nitrogen with cooling (ice-salt bath) maintaining the temperature below 20° C. After addition, the mixture was stirred for 1 h at 0° C., then cooled to –50° C. A solution of 4-methoxy benzonitrile (2.14 g, 16.08 mmol) in THF (5 mL) was added quickly. The cooling bath was removed and the reaction was allowed to warm to room temperature. A saturated aqueous NH$_4$Cl solution was added during cooling, and the solid was isolated by filtration to give the methoxy compound (2.2 g, 65%). The methoxy compound (750 mg, 2.98 mmol) was dissolved in a 50 mL flask and pyridinium hydrochloride (10 g) was added. The mixture was heated at 190° C. for 2 h, then cooled to room temperature. The reaction was then diluted with water, neutralized with NaHCO$_3$ and the solid was isolated by filtration to give 600 mg of 3-(4-hydroxyphenyl)-2H-isoquinolin-1-one (84%). MS (ES) m/z: 238.92 (M+1), 237.89 (M); MP 239-241° C.

Example 22

2-Phenyl-4H-pyrano[2,3-b]pyridin-4-one

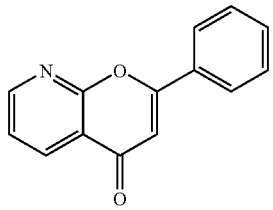 [SMILES: O=c1cc(-c2ccccc2)oc2ncccc12]

In a 250 mL dry round bottom flask with a reflux condenser and magnetic stirrer was placed with 2-chloro-3-ethyl nicotinate (12.0 g, 64.7 mmol) in dry methanol (200 mL), and CH$_3$ONa (21 mL, 97.0 mmol, 25% in methanol) were added slowly and the reaction mixture was refluxed for 16 hour. The reaction mixture was cooled to room temperature and quenched by addition of a saturated aqueous NH$_4$Cl solution and extracted with ethyl acetate. The combined organic layers were washed with water, brine, dried over Na$_2$SO$_4$ and concentrated to give 2-methoxy-3-methyl nicotinate (10.0 g, 93%). In a dry 500 mL round bottom flask NaH (549 mg, 13.7 mmol, 60% in mineral oil) was added in DMF (10 mL). Acetophenone (1.5 g, 12.5 mmol) in dry DMF (10 mL) was added drop-wise at 0° C. in 30 min. The reaction mixture was stirred for 1 h at room temperature. 2-Methoxy-3-methyl nicotinate (2.08 g, 12.5 mmol) dissolved into dry DMF (10 mL) was added slowly-on cooling. After addition the mixture was stirred for 16 h at room temperature. The reaction mixture was quenched by addition of a saturated aqueous NH$_4$Cl solution and diluted with water. The solid was filtered off, washed with water and dried to give the diketo product (2.94 g, 92%). Poly phosphoric acid (15.0 g) was heated at 90° C. and the diketo compound (1.5 g, 3.50 mmol) was added slowly and heated at 90° C. for 1 hours. The reaction mixture was cooled to room temperature and diluted with water. The solid was separated by filtration, washed with water and dried to give pure 2-phenyl-4H-pyrano[2,3-b]pyridin-4-one (655 mg, 50%); MS (ES) m/z: 224.94 (M+1), 223.95 (M); MP 103-105° C.

Example 23

2-(4-(hydroxymethyl)phenyl)-4H-pyrano[2,3-b]pyridin-4-one

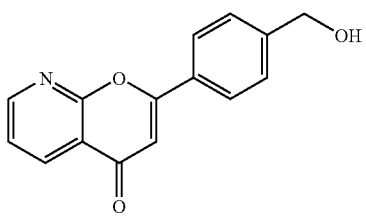 [SMILES: O=c1cc(-c2ccc(CO)cc2)oc2ncccc12]

In a 250 mL dry round bottom flask with reflux condenser and magnetic stirrer was placed 2-chloro-3-ethyl nicotinate (12.0 g, 64.7 mmol) in dry methanol (200 mL), and CH$_3$ONa (21 mL, 97.0 mmol, 25% in methanol) were added slowly and the reaction mixture was refluxed for 16 hour. The reaction mixture was cooled to room temperature and quenched by addition of a saturated aqueous NH$_4$Cl solution and extracted with ethyl acetate. The combined organic layers were washed with water, brine, dried over Na$_2$SO$_4$ and concentrated to give 2-methoxy-3-methyl nicotinate (10.0 g, 93%). In a dry 250 mL round bottom flask NaH (1.68 g, 41.0 mmol, 60% in mineral oil) was added in DMF (20 mL). 4'-Methyl acetophenone (5 g, 37.3 mmol) in dry DMF (10 mL) was added dropwise at 0° C. in 30 min. The reaction mixture was stirred for 1 h at room temperature. 2-Methoxy-3-methyl nicotinate (6.23 g, 37.3 mmol) dissolved in dry DMF (10 mL) was added slowly on cooling. After addition the mixture was stirred for 16 h at room temperature. The reaction mixture was quenched by addition of a saturated aqueous NH$_4$Cl solution and diluted with water. The solid was filtered off, washed with water and dried to give the diketo product (9.36 g, 92.5%). Poly phosphoric acid (30.0 g) was heated at 90° C. and the diketo compound (4.36 g, 16.1 mmol) was added slowly and heated at 90° C. for 1 hours. The reaction mixture was cooled to room temperature and diluted with water. The solids was separated by filtration, washed with water and dried to give 2-p-tolyl-4H-pyrano[2,3-b]pyridin-4-one (3.38 g, 89%). To a solution of 2-p-tolyl-4H-pyrano[2,3b]pyridin-4-one (1.0 g, 4.2 mmol) in CCl$_4$ (50 mL), NBS (788 mg, 4.44 mmol) was added under nitrogen, and heated under reflux for 4 h in presence of 600 w light. The reaction mixture was cooled to room temperature and filtered. The solids were dried and washed with water to give the bromide compound (698 mg, 52%). To a solution of the bromide compound (698 mg, 2.20 mmol) in DMF (20 mL), potassium acetate (649 mg, 6.62 mmol) was added. The mixture was heated at 100° C. for 1 hours. The reaction mixture was diluted with water and extracted with ethyl acetate. The combined organic layers were washed with water, brine, dried over Na$_2$SO$_4$ and concentrated to give the crude acetyl flavone (597 mg, 92%). To a solution of acetyl flavone (597 mg, 2.0 mmol) in methanol (15 mL), K$_2$CO$_3$ (840 mg, 6.07 mmol) was added and stirred for 2 h at room temperature. The solvent was removed and the product was taken into water and neutralized by dilute, HCl. The solid was isolated by, filtration, washed with water and purified by chromatography using 5% MeOH in dichloromethane to give 2-(4-(hydroxymethyl)phenyl)-4H-pyrano[2,3-b]pyridin-4-one (300 mg, 59%); MS (ES) m/z: 254.89 (M+1), 253.88 (M); MP 218-219° C.

Example 24

2-(4-hydroxy-3,5-dimethylphenyl)-4H-pyrano[2,3-b]pyridin-4-one

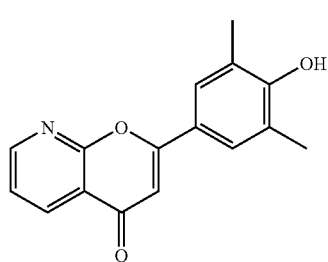 [SMILES: Cc1cc(-c2cc(=O)c3cccnc3o2)cc(C)c1O]

Ethyl-2-chloronicotinate (11.14g, 60 mmol) was dissolved in anhydrous methanol (60 mL). Sodium methoxide (18 mL, 25 wt-% in methanol) was added slowly at room temperature under nitrogen. The reaction mixture was stirred under reflux for 15 hours. Methanol was removed under vacuum. The residue was dissolved in ethyl acetate (200 mL). The organic layer was washed with a saturated aqueous NH$_4$Cl solution (1×100 mL) and brine (50 mL). Dried over anhydrous Na$_2$SO$_4$. Removal of solvent gave ethyl-2-methoxynicotinate as yellow oil (9.88 g, 91%). To a solution of 3,5-dimethyl-4-hydroxyacetophenone (2.46 g, 15 mmol) in anhydrous DMF (75 mL) was added imidazole (3.27 g, 48 mmol) and tert-butyldimethylsilylchloride (2.71 g, 18 mmol). The reaction mixture was stirred at room temperature under nitrogen for 15 hours. Water (200 mL) was added. The mixture was extracted with ethyl acetate (200 mL). The organic layer was washed with water (2×100 mL) and brine (100 mL), and dried over anhydrous Na$_2$SO$_4$. Removal of solvent gave 3,5-demthyl-4-tert-butyldimethylsilyloxy acetophenone as a colorless oil in quantitative yield (4.4 g). To a stirred solution of 3,5-demthyl-4-tert-butyldimethylsilyloxy acetophenone (1.58 g, 5.6 mmol) in anhydrous THF (15 mL) was added lithium bis (trimethylsilyl) amide (6.8 mL, 1.0M solution in THF) at −40° C. over a period of 15 min. under nitrogen. Stirring was continued at −40° C. for 15 min. A solution of ethyl-2-ethoxynicotinate in anhydrous THF (15 mL) was added slowly. Stirring was continued at 40° C. for 10 min. The mixture was allowed to warm to room temperature. Stirring was continued for another 15 h at room temperature. The reaction mixture was diluted with ethyl acetate (200 mL). A saturated aqueous NH$_4$Cl solution (50 mL) was added. The organic layer was separated and dried over anhydrous Na$_2$SO$_4$. Removal of solvent gave the desired crude compound (2.4 g) which was used in next step without purification. The above compound (2.31 g, 5.6 mmol) and pyridinium hydrochloride (6.47 g, 56 mmol) was mixed together and stirred at 190° C. for 3 hours. The mixture was cooled to room temperature. Water (100 mL) was added. The solid was filtered off, washed with water and dried under vacuum. The crude product was purified by column chromatography (SilicaGel 230-400 mesh; 2% methanol in CH$_2$Cl$_2$ as eluent) to give 2-(4-hydroxy-3,5-dimethylphenyl)-4H-pyrano[2,3-b]pyridin-4-one (0.598 g, 40% yield over two steps); MS (ES) m/z: 268.91 (M+1), 267.88 (M); MP 295-297 C Example 25

2-(pyridin-3-yl)-4H-chromen-4-one

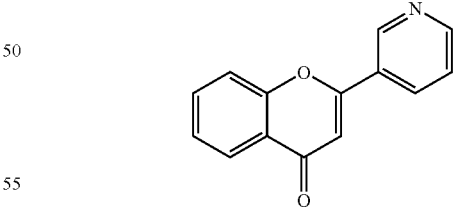

To a solution of nicotinic acid hydrochloride (0.5 g, 3.1 mmol) in CH$_2$Cl$_2$ (200 mL) at room temperature was added oxalyl chloride (0.42 mL, 4.8 mmol) and three drops of DMF. The reaction mixture was stirred at room temperature for 1 h and then concentrated using a rotary evaporator. The resulting residue was re-dissolved in toluene (50 ml), and then again concentrated using a rotary evaporator to afford nicotinic acid chloride hydrochloride (0.5 g, 90%). To a solution of 2'-hydroxyacetophenone (0.38 g, 2.8 mmol) in THF (50 mL) at room temperature was added nicotinic acid chloride hydrochloride (0.5 g, 2.8 mmol) and triethylamine (1.2 mL, 8.6 mmol). The reaction mixture was stirred at room temperature for 2 hours. The reaction was quenched with water (50 mL), extracted with $CH_2Cl_2$ (3×100 mL), concentrated using a rotary evaporator. The residue was purified by column chromatography (hexane:ethyl acetate 2:1) to provide the corresponding ester (0.42 g, 62%). A solution of the above ester (0.42 g, 1.73 mmol) in THF (50 mL) was mixed with t-BuOK (0.25 g, 2.25 mmol) and was stirred at room temperature for 16 hours. The reaction was quenched with water (50 mL) and the aqueous was acidified with HCl (0.5 N) to pH=6. The reaction mixture was extract with $CH_2Cl_2$ (3×100 mL), concentrated using a rotary evaporator, trituration in hexanes to afford a solid. This solid was collected by filtration and washed with hexanes to provide the diketone (0.3 g, 71%). A solution of the above diketone (0.3 g, 1.25 mmol) in HOAc (50 mL) and HCl (conc., 1 mL) was stirred at reflux for 2 hours. The solvent was removed using a rotary evaporator. The residue was purified by column (hexane:ethyl acetate: MeOH 3:3:1) to provide 2-(pyridin-3-yl)-4H-chromen-4-one as a light yellow solid (0.202 g, 73%); MS (ES) m/z: 224.90 (M+1), 223.92 (M); MP 122.8-124.0° C.

Example 26

7-((dimethylamino)methyl-2-(4-hydroxyphenyl)-4H-pyrano[2,3-b]pyridin-4-one dihydrochloride

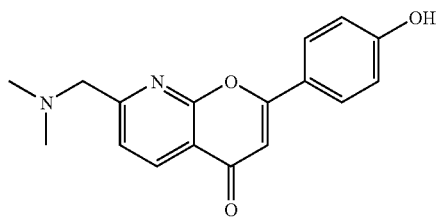 [SMILES: CN(C)Cc1ccc2c(=O)cc(-c3ccc(O)cc3)oc2n1]

In a 250 mL dry round bottom flask with reflux condenser and magnetic stirrer was placed with 2-chloro-6-methyl-3-methyl nicotinate (5.3 g, 28.6 mmol) in dry methanol (30 mL), and $CH_3ONa$ (9.2 mL, 42.8 mmol, 25% in methanol) were added slowly and the reaction mixture was refluxed for 16 hour. The reaction mixture was cooled to room temperature and quenched by addition of a saturated aqueous $NH_4Cl$ solution and extracted with ethyl acetate. The combined organic layers were washed with water, brine, dried over $Na_2SO_4$ and concentrated to give 2-methoxy-6-methyl-3-methyl nicotinate (4.37 g, 84%). In a dry 250 mL round bottom flask NaH (637 mg, 26.5 mmol, 60% in mineral oil) was added in DMF (20 mL). 4'-Methoxy acetophenone (3.62 g, 24.1 mmol) in dry DMF (10 mL) was added dropwise at 0° C. over 30 min. The reaction mixture was stirred for 1 h at room temperature. 2-Methoxy-6-methyl-3-methyl nicotinate (4.37 g, 24.1 mmol) dissolved in dry DMF (10 mL) was added slowly on cooling. After addition the mixture was stirred for 16 h at room temperature. The reaction mixture was quenched by addition of saturated aqueous $NH_4Cl$ solution and diluted with water. The solids were filtered off, washed with water and dried to give the diketo product (6.18 g, 86%). In a 50 mL flask were placed the diketo compound (3.0 g, 10.1 mmol) and pyridinium hydrochloride (25 g). The mixture was heated at 190° C. for 4 hours. The flask was cooled to room temperature, diluted with water, neutralized with $NaHCO_3$ and the solids were filtered off, dried and purified by chromatography using 5% MeOH in $CH_2Cl_2$ to give the desired intermediate (1.15 g, 46%). In a 50 mL round-bottomed flask fitted with condenser and magnetic stirrer were placed the desired intermediate (1.05 g, 4.13 mmol), $Ac_2O$ (463 mg, 4.54 mmol), pyridine (10 mL). The reaction mixture was stirred for 16 h at room temperature. The reaction mixture was poured into water. The solids were filtered off, washed with water and dried to give the acetylated product (1.157 g, 96%). To a solution of acetyl product (1.16 g, 3.92 mmol) in $CCl_4$ (50 mL), NBS (732 mg, 4.11 mmol) was added under nitrogen, and the reaction mixture was heated under reflux for 4 h in presence of 600 w light. The reaction mixture was cooled to room temperature and filtered. The solids were dried and washed well with water. The crude product was purified by chromatography using 25% ethyl acetate in dichloromethane to give the bromide compound (375 mg, 25%). To a solution of the bromide compound (375 mg, 1.00 mmol) in $CH_3CN$ (10 mL), was added dimethyl amine (181 mg, 4.02 mmol, 2 M solution in THF). The mixture was stirred at room temperature for 1 hours. The solvent was removed and the crude product was purified by chromatography using 5% MeOH in dichloromethane to give the free base. The free base was dissolved in dichloromethane (10 mL) and HCl solution in ether (1 N, 5 mL) was added. The solvent was removed and solids were dried to give 7-((dimethylamino)methyl)-2-(4-hydroxyphenyl)-4H-pyrano[2,3-b]pyridin-4-one as the dihydrochloride (275 mg, 74%). MS (ES) m/z: 296.94 (M); MP 205° C. at decomposition Example 27

2-(4-(2-(dimethylamino)ethoxy)phenyl)-4H-pyrano[2,3-b]pyridin-4-one dihydrochloride

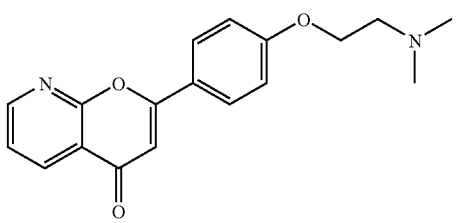 [SMILES: CN(C)CCOc1ccc(-c2cc(=O)c3cccnc3o2)cc1]

In a 500 mL dry round bottom flask with reflux condenser and magnetic stirrer was placed 2-chloro-3-ethyl nicotinate (40.0 g, 215.5 mmol) in methanol (200 mL), and $CH_3ONa$ (65 mL, 301.7 mmol, 25% in methanol) was added slowly and the reaction mixture was refluxed for 16 hour. The reaction mixture was cooled to room temperature, quenched by addition of saturated $NH_4Cl$ solution and extracted by ethyl acetate. The combined organic layer was washed well with water, brine, dried over $Na_2SO_4$ and concentrated to give 2-methoxy-3-methyl nicotinate (35 g, 970% yield). In a dry 500 mL round bottom flask sodium hydride (9.21 g, 230.3 mmol, 60%) was added in DMF (100 mL). 4-Methoxyacetophenone (31.5 g, 209 mmol) in dry DMF (50 mL) was added dropwise at 0° C. over 30 min. The reaction mixture was stirred for 1 h at room temperature. 2-Methoxynicotinic acid methyl ester (35 g, 209 mmol) dissolved in dry DMF (50 mL) was added slowly on cooling. After addition the mixture was stirred for 16 h at room temperature. The reaction mixture was quenched by addition of a saturated aqueous $NH_4Cl$ solution and diluted with water. The solids were filtered off, washed with water and dried to give the diketo product (56.7 g, 95%). The above diketo compound (56.7 g, 199 mmol) and pyridinium hydrochloride (345 g) were placed in a 1000 mL round bottom flask and the mixture was heated at 190° C. for 5 hours. The reaction mixture was cooled to room temperature and diluted with water. The solids were separated by filtration and purified by column chromatography using 5% methanol in CH$_2$Cl$_2$ to give 2-(4-Hydroxy-phenyl)-pyrano[2,3-b]pyridin-4-one (23.25 g, 48.8%). 2-(4-Hydroxy-phenyl)-pyrano[2,3-b]pyridin-4-one (0.48 g, 2.0 mmol) was suspended in anhydrous THF (25 mL). Triphenyl phosphene (0.577 g, 2.2 mmol), N,N-dimethylaminoethanol (0.213 g, 2.4 mmol) and N,N-diisopropylethylamine (0.37 g, 3.0 mmol), were added. To the stirred solution was added diethylazodicarboxylate (0.383 g, 2.2 mmol). After the addition of DEAD, the reaction mixture became a clear solution. The reaction mixture was stirred at room temperature overnight. Additional triphenyl phosphene (0.288 g, 1.1 mmol), N,N-dimethylaminoethanol (0.107 g, 1.2 mmol), N,N-diisopropylethylamine (0.185 g, 1.5 mmol), and diethylazodicarboxylate (0.191 g, 11.1 mmol) were added and stirring was continued for 15 hours. The solvent was removed under vacuum. The crude material was purified by column chromatography (Silica Gel 230-400 mesh; 2-5% methanol in CH$_2$Cl$_2$ as eluent) to give 2-[4-(2-dimethylamino ethoxy)phenyl]pyrano[2,3-b]pyridine-4-one as white solid (0.445 g, 72%). The above compound (0.2 g, 0.644 mmol) was dissolved in anhydrous Dichloromethane (10 mL). HCl in ether (3 mL, 1.0 M) was added dropwise. A yellow precipitate was formed. The reaction mixture was stirred at room temperature for 30 min. under nitrogen. The solvent was removed and the crude compound was triturated with ether to give 2-(4-(2-(dimethylamino)ethoxy)phenyl)-4H-pyrano[2,3-b]pyridinone dihydrochloride (0.24 g, 97%) as a pale yellow solid. MS (ES) m/z: 311.98 (M+1), 310.94 (M); MP 236-238° C.

Example 28

2-(4-hydroxy-3-(thiophen-2-yl)phenyl)-4H-pyrano[2,3-b]pyridin-one

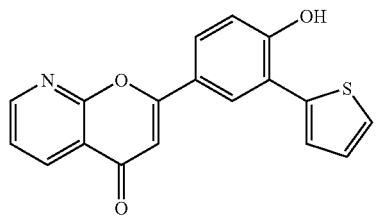 [SMILES: O=c1cc(-c2ccc(O)c(-c3cccs3)c2)oc2ncccc12]

To a solution of 4-hydroxyacetophenone (4.0 g, 30 mmol) in 50% (v/v) of ammonium hydroxide (250 mL) at room temperature was quickly added a solution of potassium iodide (24.2 g, 146 mmol) and iodine (7.66 g, 30 mmol) in water (300 mL). The resulting mixture was stirred at room temperature for 14 hours and then passed through a celite pad. The filtrate was cooled to 10° C. and acidified slowly with HCl (12 N) to pH=1. The yellow precipitate was collected by filtration, washed with water to get 4-hydroxy-3-iodoacetophenone (6.3 g, 80%). A solution of 4-hydroxy-3-iodoacetophenone (3 g, 11.5 mmol) and 2-thiophenylboronic acid (1.46 g, 11.5 mmol) in DMF (50 mL) was mixed with potassium carbonate (3.16 g, 22.9 mmol) and Pd(dppf)$_2$ (0.25 g, 0.344 mmol). The mixture was stirred at 90° C. for 14 hours, cooled to room temperature and passed through a celite pad. The filtrate was diluted with water and extracted with EtOAc (3×100 mL). The residue after concentration was purified by column (SiO$_2$, Hexanes/EtOAc=4:1) to provide 4-hydroxy-3-(2-thiophenyl)acetophenone (1.1 g, 44%) as a light yellow solid. To a solution of 4-hydroxy-3-(2-thiophenyl)acetophenone (0.5 g, 2.29 mmol) in THF (50 mL) at –78° C. was added LDA in heptane-THF (2.6 mL, 4.7 mmol) and the solution was stirred for 1 hours. 2-Chloronicotinyl chloride (0.202 g, 1.15 mmol) was added and the resulting mixture was stirred at –78° C. for 1 h and 1 h at room temperature. The reaction was quenched with aqueous HCl (0.5 N) and extracted with CH$_2$Cl$_2$ (×3×100 mL). The residue after concentration was purified by column (SiO$_2$, Hexanes/EtOAc=2:1) to provide the corresponding diketone (0.31 g, 76%). The above diketone (0.28 g, 0.78 mmol) was dissolved in HOAc (50 mL) and stirred at, 10° C. for 2 hours. It was poured into icy water. The solid was collected by filtration, washed with CH$_2$Cl$_2$ to afford 2-(4-hydroxy-3-(thiophen-2-yl)phenyl)-4H-pyrano[2,3-b]pyridin-4-one (0.146 g, 58%) as a grey solid; MS (ES) m/z: 322.93 (M+1), 321.93 (M); MP 273.5-275° C.

Example 29

2-(2,6-dimethyl-4-(4-oxo-4H-pyrano[2,3-b]pyridin-2-yl)phenoxy)acetic Acid

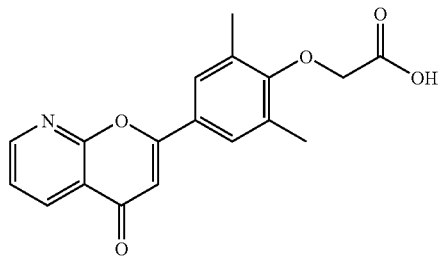 [SMILES: Cc1cc(-c2cc(=O)c3cccnc3o2)cc(C)c1OCC(=O)O]

Ethyl 2-chloronicotinate (11.14 g, 60 mmol) was dissolved in anhydrous methanol (60 mL). Sodium methoxide (18 mL, 25 wt % in methanol) was added slowly at room temperature under nitrogen. The reaction mixture was stirred under reflux for 15 hours. Methanol was removed under vacuum. The residue was dissolved in ethyl acetate (200 mL). The organic layer was washed with a saturated aqueous NH$_4$Cl solution (1×100 mL) and brine (50 mL), and dried over anhydrous Na$_2$SO$_4$—Removal of solvent gave ethyl-2-methoxynicotinate (9.88 g, 91%) as yellow oil. To a solution of 3,5-dimethyl-4-hydroxyacetophenone (2.46 g, 15 mmol) in anhydrous DMF (75 mL) were added imidazole (3.27 g, 48 mmol) and tert-butyldimethylsilylchloride (2.7 g, 18 mmol). The reaction mixture was stirred at room temperature under nitrogen for 15 hours. Water (200 mL) was added. The mixture was extracted with ethyl acetate (200 mL). The organic layer was washed with water (2×100 mL) and brine (100 mL), and dried over anhydrous Na$_2$SO$_4$. Removal of solvent gave 3,5-demthyl-4-tert-utyldimethylsilyloxy acetophenone as a colorless oil in quantitative yield (4.4 g). To a stirred solution of 3,5-demthyl-4-tert-butyldimethylsilyloxy acetophenone (1.58 g, 5.6 mmol) in anhydrous THF (15 mL) was added lithium bis(trimethylsilyl)amide (6.8 mL, 1.0 M solution in THF) at –40° C. under nitrogen over a period of 15 min. Stirring was continued at –40° C. for 15 min. A solution of ethyl-2-methoxynicotinate in anhydrous THF (15 mL) was added slowly. Stirring was continued at –40° C. for 10 min, then allowed to warm to room temperature. Stirring was continued for another 15 h at room temperature. The reaction mixture was diluted with ethyl acetate (200 mL). A saturated aqueous NH₄Cl solution (50 mL) was added. The organic layer was separated and dried over anhydrous Na₂SO₄. Removal of solvent gave the desired crude compound (2.4 g) which was used in next step without purification. The above compound (2.31 g, 5.6 mmol) and pyridinium hydrochloride (6.47 g, 56 mmol) was mixed together and stirred at 190° C. for 3 hours. The mixture was cooled to room temperature. Water (100 mL) was added. The solid was isolated, washed with water and dried under vacuum. The crude product was purified by column chromatography (SilicaGel 230-400 mesh; 2% methanol in CH₂Cl₂ as eluent) to give the desired intermediate (0.598 g, 40% over two steps) as an off-white solid. To a solution of the desired intermediate (0.53 g, 2.0 mmol) in anhydrous DMF (10 mL) sodium hydride (0.88 g, 2.2 mmol) was added in portions. The reaction mixture was stirred at room temperature for 10 min. Ethyl-2-bromo acetate (0.367 g, 2.2 mmol) was added and stirring was continued at room temperature for 15 h under nitrogen. Water (30 mL) was added, and the solid was filtered off, washed with water and dried under vacuum to give [2,6-dimethyl-4-(4-oxo-4H-pyrano[2,3-b]pyridin-2-yl)phenoxy]acetic acid ethyl ester (0.69 g, 97%). The above compound (0.35 g, 1.0 mmol) was suspended in THF (10 mL). An, aqueous solution of sodium hydroxide (0.08 g, 2.0 mmol) in water (1 mL) was added and the mixture was stirred at room temperature for 24 h (progress of the reaction was monitored by TLC). The solvent was evaporated to dryness. The crude compound was washed with THF. The residue was dissolved in water (10 mL) and acidified to pH ~2. The formed precipitate was filtered off and dried under vacuum the crude compound was purified by column chromatography (Silica Gel 230-400 mesh; 5% MeOH in CH₂Cl₂ as eluent) to give 2-(2,6-dimethyl-4-(4-oxo-4H-pyrano[2,3-b]pyridin-2-yl)phenoxy)acetic acid (0.21 g, 64%) as pale yellow solid; MS (ES) m/z: 326.91 (M+1), 325.90 (M); MP 280° C. at decomposition.

Example 30

2-(pyridin-4-yl)-4H-pyrano[2,3-b]pyridin-4-one hydrochloride

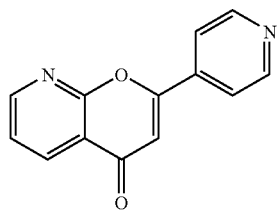 [SMILES: O=c1cc(-c2ccncc2)oc2ncccc12]

In a dry 250 mL round bottom flask NaH (519 mg, 12.98 mmol, 60% in mineral oil) was added in DMF (10 mL). 4-Acetyl pyridine (1.43 g, 11.8 mmol) in dry DMF (5 mL) was added dropwise at 0° C. over 30 min. The reaction mixture was stirred for 1 h at room temperature. Methyl 2-methoxynicotinate (1.98 g, 1.1.8 mmol) dissolved in dry DMF (5 mL) was added slowly on cooling. After addition, the mixture was stirred for 16 h at room temperature. The reaction mixture was quenched by addition of a saturated aqueous NH₄Cl solution and diluted with water. The product was extracted with ethyl acetate and the combined organic layers were washed with water, brine, dried over Na₂SO₄ and concentrated to give 350 mg of the crude diketone. The diketone (350 mg, 1.36 mmol) and polyphosphoric acid (5 g) were placed in a 50 mL flask and the mixture was heated at 100° C. for 1 hours. The reaction flask was cooled to room temperature, the mixture was diluted with water, neutralized with 1 N NaOH solution and extracted with ethyl acetate. The combined organic layers were washed with water, brine, dried over Na₂SO₄ and concentrated to give the crude product, which dissolved in CH₂Cl₂ and treated with 2N HCl solution in ether. The solids were dissolved in CH₂Cl₂ (10 mL) and 2N HCl solution in ether was added. The solids were filtered and dried to give 2-(pyridin-4-yl)-4H-pyrano[2,3-b]pyridin-4-one hydrochloride (134 mg, 38%); MS (ES) m/z: 224.90 (M); MP 248-250° C.

Example 31

2-(3,5-dimethyl-4-(2-morpholinoethoxy)phenyl)-4H-pyrano[2,3-b]pyridin-4-one hydrochloride

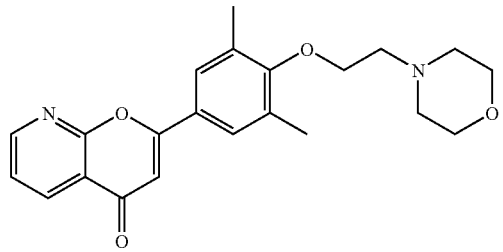 [SMILES: Cc1cc(-c2cc(=O)c3cccnc3o2)cc(C)c1OCCN1CCOCC1]

Ethyl-2-chloronicotinate (11.1 g, 60 mmol) was dissolved in anhydrous methanol (60 mL). Sodium methoxide (18 mL, 25 wt % in methanol) was added slowly at room temperature under nitrogen. The reaction mixture was stirred under reflux for 15 h. The methanol was removed under vacuum. The residue was taken into ethyl acetate (200 mL). The organic layer was washed with a saturated aqueous NH₄Cl solution (1×100 mL) and brine (50 mL), and dried over anhydrous Na₂SO₄. Removal of solvent gave ethyl-2-methoxynicotinate (9.9 g, 91%) as yellow oil. To a solution of 3,5-dimethyl-4-hydroxyacetophenone (2.5 g, 15 mmol) in anhydrous DMF (75 mL) was added imidazole (3.3 g, 48 mmol) and tert-butyldimethylsilylchloride (2.7 g, 18 mmol). The reaction mixture was stirred at room temperature under nitrogen for 15 hours. Water (200 mL) was added. The mixture was extracted with ethyl acetate (200 mL). The organic layer was washed with water (2×100 mL), brine (100 mL), and dried over anhydrous Na₂SO₄. Removal of solvent gave a colorless oil in quantitative yield (4.4 g). To a stirred solution of the 3,5-dimethyl-4-tert-butyldimethylsilyloxy acetophenone (1.6 g, 5.6 mmol) in anhydrous THF (15 mL) was added lithium bis(trimethylsilyl) amide (6.8 mL, 1.0 M solution in THF) at −40° C. over a period of 15 min. under nitrogen. The stirring continued at 40° C. for 15 min. A solution of ethyl-2-methoxynicotinate in anhydrous THF (15 mL) was added slowly. The stirring was continued at −40° C. for 10 min. Then allowed to warm to room temperature and stirred for another 15 h at room temperature. The reaction mixture was diluted with ethyl acetate (200 mL). A saturated aqueous NH₄Cl solution (50 mL) was added. The organic layer was separated and dried over anhydrous Na₂SO₄. Removal of solvent gave the crude product (2.4 g), which was used in next step without purification. The above compound (2.31 g, 5.6 mmol) and pyridinium hydrochloride (6.5 g, 56 mmol) was mixed together and stirred at 190° C. for 3 hours. The mixture was cooled to room temperature and water (100 mL) was added. The solid was separated by filtration, washed with water and dried under vacuum. The crude product was purified by column chromatography (SilicaGel 230-400 mesh; 2% methanol in CH$_2$Cl$_2$ as eluent) to give the desired intermediate in (0.6 g, 40% yield from two steps) as an off-white solid. To a solution of the desired intermediate (0.86 g, 3.2 mmol) in anhydrous DMF (20 mL) was added sodium hydride (0.180 g, 4.49 mmol, 60% suspension in mineral oil) in small portions and stirred for 15 min. under nitrogen. A solution of 1-chloro-2-iodoethane (0.765 g, 4.02 mmol) in anhydrous DMF (5 mL) was added dropwise. The reaction mixture was stirred for 3 days (progress of the reaction mixture was monitored by TLC). Water (100 mL) was added. The mixture was extracted with THF and ethyl acetate (1:2, 150 mL). The organic layer was washed with brine (50 mL) and dried over anhydrous Na$_2$SO$_4$. The crude material was purified by column chromatography (Silica Gel 230-400 mesh; 2-5% MeOH in CH$_2$Cl$_2$ as eluent) to give 2-[-(2-chloroethoxy)-3,5-dimethylphenyl] pyrano[2,3-b]pyridine-4-one (0.4g, 38%) of as a pale yellow solid. The above compound (0.19 g, 0.58 mmol) was dissolved in anhydrous DMSO (5 mL). Morpholine (0.25 g, 2.9 mmol) and triethylamine (0.29 g, 2.9 mmol) were added and the reaction mixture was stirred at 110° C. for 15 h. The reaction mixture was cooled to room temperature and water (20 mL) was added. A solid precipitated out and was isolated by filtration. It was washed with water and dried under vacuum. The crude compound was purified by column chromatography (Silica Gel 230-400 mesh; 2-5% MeOH in CH$_2$Cl$_2$ as eluent) to give 2-[3,5-dimethyl-4-(2-morpholinylethoxy)phenyl]pyrano[2,3-b]pyridine-4-one (0.11 g, 50%) as a pale yellow solid. To a solution of above compound (0.098 g, 0.26 mmol) in anhydrous CH$_2$Cl$_2$ (5 mL) was added hydrogen chloride (1 mL, 1.0 M solution in ether) dropwise. The reaction mixture was stirred at room temperature for 2 hours. The solvent was removed and the solid was triturated with 10% methanol in ether to give 2-(3,5-dimethyl-4-(2-morpholinoethoxy)phenyl)-4H-pyrano[2,3-b]pyridin-4-one (0.09 g 77%) as the hydrochloride; MS (ES) m/z: 381.03 (M+1); MP 276-278° C.

Example 32

2-(3-Bromo-4-hydroxyphenyl)-4H-pyrano[2,3-b]pyridin-4-one

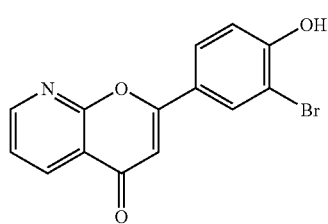

Sodium methoxide (18 mL, 25 wt % in methanol) was added slowly to a solution of ethyl-2-chloronicotinate (11.14 g 60 mmol) in anhydrous methanol (60 mL). The reaction mixture was stirred under reflux for 15 h, then cooled to room temperature. The methanol was removed in vacuo. The residue was dissolved in EtOAc (200 mL) and sat. ammonium chloride solution (50 mL) was added. The organic layer was separated and dried over anhydrous Na$_2$SO$_4$. Removal of solvent gave ethyl-2-methoxynicotinate (8.58 g, 79%) as yellow oil. Sodium hydride (0.21 g, 60% in mineral oil, 5.16 mmol) was mixed with anhydrous DMF (5 mL). A solution of 3'-bromo-4'-methoxyacetophenone (0.99 g, 4.3 mmol) in anhydrous DMF (3 mL) was added drop-wise at 0° C. under nitrogen. The mixture was stirred at 0° C. for 5 min. and then at room temperature for 30 min. The mixture was cooled to 0° C. A solution of ethyl 2-methoxy nicotinate (1.81 g, 10 mmol) in anhydrous DMF (3 mL) was added slowly. The ice bath was removed and the stirring continued at room temperature under nitrogen for 20 hours. Water (20 mL) was added and the mixture was extracted with EtOAc (2×1.00 mL). The organic layer was washed with brine and dried over anhydrous Na$_2$SO$_4$. Removal of the solvent gave a dark solid. Triturating with ether gave a yellow solid (1.329 g, 84%). The solid (1.31 g, 3.6 mmol) and pyridinium hydrochloride (6.24g, 54 mmol) were mixed together and stirred at 190° C. for 3 h, The reaction mixture was then cooled to room temperature, followed by the addition of water (200 mL). The solid was isolated by filtration, washed with water and dried under vacuum. The crude compound was purified by column chromatography (Silica Gel 230-400 mesh; 5:4:1 hexanes, EtOAc and methanol as an eluent) to give 2-(3-bromo-4-hydroxyphenyl)-4H-pyrano[2,3-b]pyridinone (0.453 g, 40%) of as yellow solid. MS (ES) m/z: 317.84, 239.9; Mp. 267-272° C.

Example 33

2-(4-hydroxy-3,5-dimethylphenyl)-6-(pyrrolidin-1-ylmethyl)-4H-pyrano[2,3-b]pyridin-4-one dihydrochloride

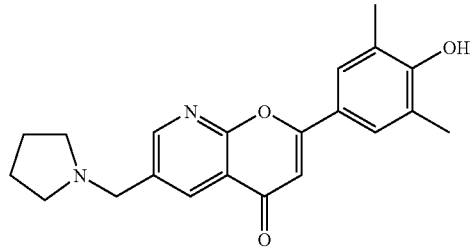 [SMILES: Cc1cc(-c2cc(=O)c3cc(CN4CCCC4)cnc3o2)cc(C)c1O]

A solution of oxalyl chloride (32.8 g, 0.258 mol) in 1,2-dichloroethane (50 mL) was added dropwise to a stirred, cooled (0° C.) solution of dimethylformamide (43.2 g, 0.591 mol) in 1,2-dichloroethane (70 mL) so that the temperature of the reaction mixture did not exceed 10° C. The resulting mixture was stirred at 0-5° C. for a further 1.75 hours then allowed to reach room temperature. 2-Methylmalonic acid (14.0 g, 0.118 mol) was added to the stirred mixture. The mixture was stirred at reflux temperature for 6 hours then at room temperature overnight. The solvent was evaporated (keeping bath temperature at 25° C. or less) and replaced with dry methanol. Methylcyanoacetate (12.9 g, 0.130 mol) was added and the mixture was stirred. Sodium methoxide (86.6 mL, 25% in methanol) was added ensuring that the reaction mixture temperature did not exceed 30° C. The cooled mixture was stirred for 30 min. then at room temperature for 3.5 hours. T solvent was removed by evaporation and replaced with dichloroethane. The mixture was washed with water, dried and evaporated. The crude product was triturated with cold methanol (30 mL) to yield the desired methyl 5-(N,N-dimethylamino)-2-cyano-4-methylpent-2,4-dienoate (17.0 g, 66.0%) as a yellow solid. MP 163-164° C. Hydrogen chloride gas was bubbled through a suspension of methyl 5-(N, N-dimethylamino)-2-cyano-4-methylpent-2,4-dienoate (17.0 g, 0.078 mol) in 1,2-dichloroethane for 6 hours. Further saturation of the suspension with HCl gas was followed by stirring at room temperature overnight. Excess HCl was blown out of the reaction mixture with nitrogen gas. The mixture was washed with water, dried and evaporated. The resulting oil crystallized on standing to yield an orange solid (14.4 g, 99%). The orange solid (14.0 g, 0.0754 mol) in anhydrous methanol (40 mL) was added to a 250 mL dry flask with reflux condenser. Sodium methoxide (31 mL, 0.14 mol, 25% in methanol) was added to the solution and the reaction was carried out at reflux overnight. Acetic acid was added to the mixture until pH 7.0 and the methanol was removed. The residue was poured into water and extracted with dichloromethane. The organic layer was further washed with water, brine and dried over sodium sulfate. Dichloromethane was removed to yield the desired intermediate (13.5 g, 98.0%). The intermediate (8.65 g, 0.048 mol) was dissolved in dry carbon tetrachloride (80 mL) and NBS (8.95 g, 0.050 mol) was added. The reaction mixture was heated to reflux under a lamp for 3 hour. After cooling, the solvent Was removed and the residue was further washed with hot water to get ride of the succinimide. The solid was purified by column (DCM: ethyl acetate 30:1) to yield the desired intermediate (7.77 g, 62.2%). The intermediate (0.85 g, 0.00327 mol), pyrrolidine (0.93 g, 0.0131 mol) and anhydrous THF (10 mL) was heated to reflux for 2 hours. The solvent was evaporated. The residue was purified by column (ethyl acetate to ethyl acetate:MeOH 9:1) to give the desired advanced intermediate (0.60 g, 73.4%). 3,5-Dimethyl-4-hydroxyacetophenone (5.3 g, 0.032 mol) and dry DMF (12 mL) was charged in a 100 mL flask. Sodium hydride (1.28 g, 0.032 mol, 60% in mineral oil) was added followed by benzyl bromide (4.0 mL, 0.032 mol) and the reaction mixture was kept stirring for overnight. The reaction mixture was poured into water (150 mL) and dichloromethane (150 mL) was added. The organic phase was separated and further washed with water (3×120 mL), brine and dried over sodium sulfate. The DCM was removed and the desired compound was solidified and further washed with hexane to yield the desired building block (7.30 g, 89.7%). The advanced intermediate from above (0.60 g, 0.0024 mol) and the building block described above (0.61 g, 0.0024 mol) were added to a 50 mL flask with anhydrous DMF (5 mL). Sodium hydride (0.2 g, 60% in mineral oil) was added and the reaction mixture was kept overnight at room temperature. The mixture was poured into water (80 mL) and extracted with DCM (3×80 mL) after pH was adjusted to 7.0. The organic phase was further washed with water, brine and dried over sodium sulfate. Evaporation of the solvent left 1.0 g (88.2%) of the crude product. The crude product (1.0 g, 0.0021 mol) and pyridine hydrogen chloride (2.0 g, 0.0169 mol) were mixed in a 50 mL flask and heat to 190° C. for 4 h. The mixture was cooled and poured into methanol (8 mL), then filtered. The collected solid was further washed with ethyl acetate and dry to get the hydrochloride 2-(4-hydroxy-3,5-dimethylphenyl)-6-(pyrrolidin-1-ylmethyl)-4H-pyrano[2,3-b]pyridin-4-one dihydrochloride (0.50 g, 58.7%); MS (ES) m/z: 351.03 (M); MP 337-338° C.

Example 34

5,7-dimethoxy-2-(pyridin-4-yl)-4H-chromen-4-one hydrochloride

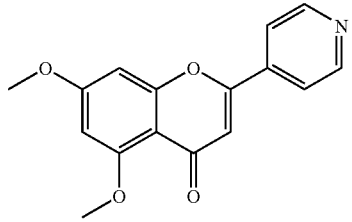 [SMILES: COc1cc(OC)c2c(=O)cc(-c3ccncc3)oc2c1]

To a mixture of 2-hydroxy-4,6-dimethoxy acetophenone (2.00 g, 10.2 mmol), isonicotinic acid (1.25 g, 10.2 mmol) in pyridine (30 mL) was added POCl$_3$ (1.72 g, 11.2 mmol) slowly at 0° C. The reaction was stirred at room temperature for 16 hours. Water (50 mL) was added, and the solid was separated by filtration and dried to give isonicotinic acid-2-acetyl-3,5-dimethoxypheanyl ester (2.72 g, 86%).

To a solution of isonicotinic acid-2-acetyl-3,5-dimethoxyphenyl ester (2.72 g, 9.03 mmol) in anhydrous THF (50 mL) was added potassium tert-butoxide (1.21 g, 10.8 mmol) in small portions. The reaction mixture was stirred at room temperature for 24 hours. A sat. NH$_4$Cl solution (20 mL) was added. The organic layer was separated and aqueous phase was extracted with ethyl acetate (100 mL). The combined organic phase were washed with water, brine and dried over anhydrous Na$_2$SO$_4$. Removal of solvent gave 1-(2-hydroxy-4,6-dimethoxyphenyl)-3-pyridin-4-yl-propane-1,3-dione (2.4 g, 88%). To a mixture of 1-(2-hydroxy-4,6-dimethoxyphenyl)-3-pyridin-4-yl-propane-1,3-dione (2.4 g, 7.96° mmol) acetic acid (10 mL) and conc. HCl (1 mL) was heated at 100° C. for 1 hours. The reaction mixture was cooled to room temperature, diluted with water, neutralized with a sat. aqueous NaHCO$_3$ solution. The solid was filtered off and dissolved in CH$_2$Cl$_2$ (120 mL) and hydrogen chloride in ether (5 mL, 2.0M solution) was added. The formed solid was isolated by filtration, washed with 10% methanol in ether and ether to give 5,7-dimethoxy-2-(pyridin-4-yl))-4H-chromen-4-one hydrochloride (0.335 g, 13%) as a yellow solid; MS (ES) m/z: 283.94 (M); MP 234-235° C.

Example 35

2-phenyl-6-(pyrrolidin-1-ylmethyl)-4H-pyrano[2,3-b]pyridin-4-one hydrochloride

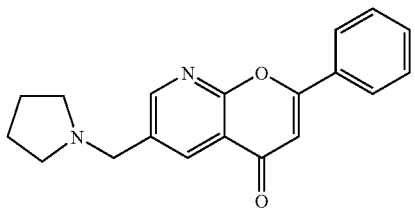 [SMILES: O=c1cc(-c2ccccc2)oc2ncc(CN3CCCC3)cc12]

A solution of oxalyl chloride (32.8 g, 0.258 mol) in 1,2-dichloroethane (50 mL) was added dropwise to a stirred, cooled-(0° C.) solution of dimethylformamide (43.2 g, 0.59 mol) in 1,2-dichloroethane (70 mL) so that the temperature of the reaction mixture did not exceed 10° C. The resulting mixture was stirred at 0-5° C. for 1.75 hours then allowed to reach room temperature. 2-Methylmalonic acid (14.0 g, 0.12 mol) was added to the stirred mixture. When gas evolution ceased, the mixture was stirred at reflux temperature for 6 hours then at room temperature overnight. The solvent was evaporated (keeping bath temperature at 25° C. or less) and replaced with dry methanol. Methylcyanoacetate (12.86 g, 0.130 mol) was added and the mixture was stirred. Sodium methoxide (86.6 mL 25% in methanol) was added ensuring that the reaction mixture temperature did not exceed 30° C. The cooled mixture was stirred for 30 min. then at room temperature for 3.5 hours. The solvent was removed by evaporation and replaced with dichloroethane. The mixture was then washed with water, dried and concentrated. The crude product was triturated with cold methanol (30 mL) to yield methyl 5-N,N-dimethylamino)-2-cyano-4-methylpent-2,4-dienoate as a yellow solid (17.0 g 66%). M.p. 163-164° C. Hydrogen chloride gas was bubbled through a suspension of methyl 5-(N,N-dimethylamino)-2-cyano-4-methylpent-2,4-dienoate (17.0 g, 0.078 mol) in 1,2-dichloroethane for 6 hours. Further saturation of the suspension with HCl gas was followed by stirring at room temperature overnight. Excess HCl was blown out of the reaction mixture with nitrogen gas.

The mixture was washed with water, dried and concentrated. The resulting oil crystallized on standing to yield an orange solid (14.4 g, 99%). The orange solid (14.0 g, 0.075 mol) was dissolved in anhydrous methanol (40 mL) in a 250 mL dry flask with reflux condenser. Sodium methoxide (31 mL, 0.143 mol, 25% in methanol) was added to the solution and the reaction was carried out at reflux overnight. Acetic acid was added to the mixture to pH 7.0 and methanol was removed. The residue was poured into water and extracted with dichloromethane. The organic layer was further washed with water, brine and dried over sodium sulfate. Dichloromethane was removed to yield the desired intermediate (13.5 g, 98.0%). The intermediate (8.65 g, 0.048 mol) was dissolved in dry carbon tetrachloride (80 mL) followed by addition of NBS (8.95 g, 0.050 mol). The reaction mixture was heated to reflux under a lamp for 3 hour. After cooling the solvent was removed and the residue was further washed with hot water to get rid of succinimide. The solid was then purified by column (DCM: ethyl acetate 30:1) to yield the desired intermediate (7.77 g, 62.2%). A mixture of the intermediate (4.4 g, 0.017 mol), pyrrolidine (4.81 g, 0.068 mol) and anhydrous THF (20 mL) was heated to reflux for 2 hours. The solvent was evaporated. The residue was purified by column (ethyl acetate to ethyl acetate:MeOH 9:1) to give the desired intermediate (3.50 g, 82.8%). The intermediate (0.50 g, 0.002 mol) and acetophenone (0.24 g, 0.002 mol) were added to a 50 mL flask with anhydrous DMF (4 mL). Sodium hydride (0.16 g, 60% in mineral oil) was added and the reaction mixture was kept overnight at room temperature. The mixture was poured into water (80 mL) and extracted with DCM (3×80 mL) after pH was adjusted to 7.0. The organic layer was further washed with water and brine. The organic layer was dried over sodium sulfate and concentrated to yield the desired intermediate (0.45 g, 66.5%). A 50 mL flask was charged with the intermediate (0.45 g, 0.00133 mol) and pyridine hydrogen chloride (1.54 g, 0.0133 mol) and heat to 190° C. for 1 h. The mixture was cooled and poured into methanol (4 mL) then filtered, the collected solid was further washed with ethyl acetate and dried to give 2-phenyl-6-(pyrrolidin-1-ylmethyl)-4H-pyrano[2,3-b]pyridin-4-one (0.190 g, 41.7%) as the hydrochloride salt. MS (ES) m/z: 306 (M); MP 294-296° C.

Example 36

6-(4-oxo-4H-chromen-2-yl)benzo[d]oxazol-2(3H)-one

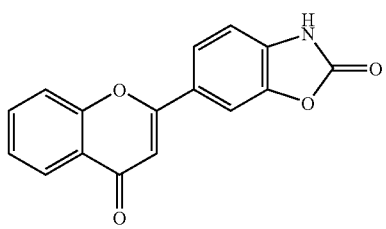 [SMILES: O=c1[nH]c2ccc(-c3cc(=O)c4ccccc4o3)cc2o1]

Step 1: To a round bottomed flask was added methyl 4-amino-3-hydroxybenzoate (4.0 g, 23.9 mmol) under nitrogen. Dry dichloromethane (100 mL) was added with stirring. Triethyl amine (7.3 mL, 52.6 mmol), was added, followed by slow addition of triphosgene (2.84 g, 9.56 mmol). The reaction mixture was stirred at room temperature overnight. The solvent was evaporated and the reaction mixture was diluted with ethyl acetate. The organic layer was washed successively with water, diluted sodium bicarbonate; water, 1 N HCl, water, brine and dried over sodium sulfate. The solvent was evaporated in vacuo to leave a residue, which was recrystallized from ethyl acetate and hexane afforded 3.4 g (81%) of desired intermediate.

Step 2: The product (1.64 g, 8.47 mmol) from step 1 was dissolved in a mixture of methanol (5 mL) and tetrahydrofuran 5 mL. Potassium hydroxide (1.25 g, 22.28 mmol) in water (6 mL) was added. The reaction mixture was refluxed at 70° C. for 3 days and 80° C. for 2 days. The solvent was evaporated in vacuo. Water was added and the reaction mixture was acidified with 1 N HCl (pH 4-5) and extracted with ethyl acetate. The solvent was evaporated in vacuo to leave 1.43 g (94%) of pure compound. The compound was used for the following reaction without further purification.

Step 3: The product from step 2 (0.108 g, 0.6-mmol) and 2-hydroxyacetophenone (0.09 g, 0.66 mmol) were added to a round bottomed flask under nitrogen. Anhydrous pyridine (5 mL was added to it with stirring. The reaction mixture was cooled down using an ice bath. Phosphorus oxychloride (0.15 g, 0.99 mmol) was added and the reaction mixture was stirred at room temperature overnight. Pyridine was removed under vacuum and the residue was acidified with 1 N HCl (pH 4~5) and extracted with ethyl acetate. The solvent was evaporated in vacuo to leave a residue which was purified by silica gel column chromatography (15 g). The eluent was a mixture of ethyl acetate and hexane in 1:1. Fraction 1 was evaporated affording pure compound (0.0192 g, 11%).

Step 4: The product from step 3 (0.25 g, 0.84 mmol) was taken in a three-necked round bottomed flask under nitrogen. Anhydrous tetrahydrofuran (15 mL) was added, followed by potassium tert-butoxide (0.142 g, 1.26 mmol). The reaction mixture was stirred at room temperature for 24 hours. Water (20 mL) was added and the reaction mixture was quenched with 1 N HCl and extracted with ethyl acetate. The solvent was evaporated in vacuo to leave a residue, which was purified by silica gel column chromatography (25 g) using gradient elution technique (20%-50% ethyl acetate in hexane), giving the desired compound (0.183 g, 73%).

Step 5: The compound from step 4 (0.18 g, 0.61 mmol) was dissolved in acetic acid (30 mL), followed by addition of conc. HCl (2 mL). The reaction mixture was refluxed for 2 hours (bath temp. 130° C.). Acetic acid was evaporated in vacuo and water was added. The solid was filtered off and dried under vacuum to give 6-(4-oxo-4H-chromen-2-yl)benzo[d]oxazol-2(3H)-one (0.119 g, 70%); MS (ES) m/z: 279.84 (M); MP 347.6-348.2° C.

Example 37

2-(4-fluorophenyl)-6-(pyrrolidin-1-ylmethyl)-4H-pyrano[2,3-b]pyridin-4-one hydrochloride

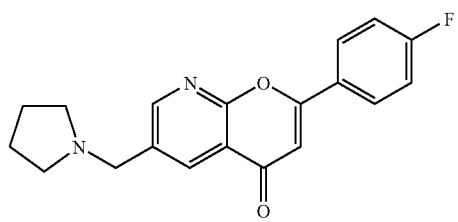 [SMILES: O=c1cc(-c2ccc(F)cc2)oc2ncc(CN3CCCC3)cc12]

To a stirred solution of 2-methoxy-5-pyrrolidin-1-ylmethyl nicotinic acid methyl ester (0.5 g, 2.0 mmol) and 1-(4-fluorophenyl)ethanone (0.276 g, 2.0 mmol) in anhydrous DMF (3 mL), sodium hydride (0.160 g, 2.0 mmol, 60% suspension in mineral oil) was added in small portions under nitrogen. The reaction mixture was stirred overnight at room temperature. A saturated aqueous NH₄Cl solution (30 mL) was added. The mixture was extracted with ethyl acetate (100 mL). The organic layer was washed with water (30 mL) and brine (30 mL), and dried over anhydrous Na₂SO₄. Removal of solvent gave a brown solid (0.45 g) which was used in next step without further purification. The above compound (0.45 g, 1.26 mmol) and pyridine hydrochloride (1.6 g, 12.6 mmol) were mixed together and stirred at 190° C. for 4 hours. Cooled to room temperature. Water (10 mL) was added, neutralized to pH ~9 with sat. aqueous NaHCO₃ solution. The solid was separated by filtration. The solid was dissolved in 1:1 CH₂Cl₂-methanol (5 mL). Hydrogen chloride in ether (1 mL, 1.0M solution) was added and the reaction mixture was stirred at room temperature for 1 hours. The solvent was removed under reduced pressure. The residue was triturated with 100% methanol in ether to give 2-(4-fluorophenyl)-6-(pyrrolidin-1-ylmethyl 4H-pyrano[2,3-b]pyridin-4-one hydrochloride (205 mg, 51%) as yellow solid. MS (ES) m/z: 324.89 (M); MP 265-268° C.

Example 38

2-(4-aminophenyl)-4H-pyrano[2,3-b]pyridin-4-one hydrochloride

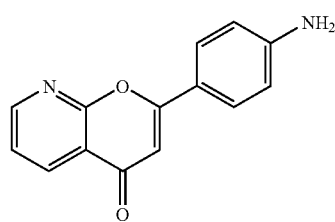 [SMILES: Nc1ccc(-c2cc(=O)c3cccnc3o2)cc1]

To a solution of 2-(4-amino phenyl)pyrano[2,3-b]pyridine-4-one (0.115 g, 0.483 mmol) in dichloromethane (10 mL) and methanol (1 mL) was added of hydrogen chloride in ether (1.0 mL, 1.0M solution) dropwise. A orange precipitate was formed. Stirred under nitrogen for 1 hours. The solvent was removed and the solid was triturated with 10% methanol in ether to give 2-(4-aminophenyl-4H-pyrano[2,3-b]pyridin-4-one (0.13 g, 98%) as the orange hydrochloride; MS (ES) m/z: 238 (M); MP 254-255° C.

Example 39

2-(4-isopropoxyphenyl)-6-(pyrrolidin-1-ylmethyl)-4H-pyrano[2,3-b]pyridinone hydrochloride

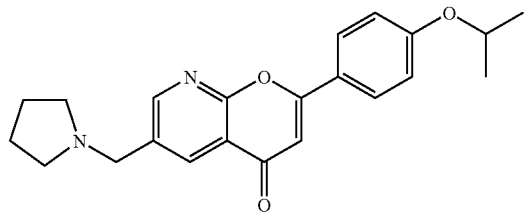 [SMILES: CC(C)Oc1ccc(-c2cc(=O)c3cc(CN4CCCC4)cnc3o2)cc1]

Sodium hydride (1.32 g, 33 mmol, 60% suspension in mineral oil) was suspended in anhydrous DMF (20 mL). A solution of 4-hydroxy acetophenone (4.08 g, 30 mmol) in anhydrous DMF (20 mL) was added dropwise at room temperature. The reaction mixture was stirred at room temperature for 30 min. A solution of 2-bromopropane (4.61 g, 37.5 mmol) in anhydrous DMF (10 mL) was added slowly. The reaction mixture was stirred at room temperature overnight. Water (100 mL) was added. The mixture was extracted with ethyl acetate (2×100 mL). The organic layer was washed with water (3×50 mL) and brine (50 mL). Dried over anhydrous Na₂SO₄. Removal of solvent gave 1-(4-isopropoxy phenyl) ethanone as a pale yellow solid (3.52 g, 66%). To a stirred solution of 2-methoxy-5-pyrrolidin-1-ylmethyl nicotinic acid methyl ester (0.5 g, 2.0 mmol) and 1-(4-isopropoxy phenyl)ethanone in anhydrous DMF (10 mL), sodium hydride (96 mg, 2.4 mmol, 60% suspension in mineral oil) was added in small portions under nitrogen. The reaction mixture was stirred overnight at room temperature. Reaction mixture was stirred at 80° C. for 1 hours. Water (30 mL) was added. The mixture was extracted with chloroform (150 mL). The organic layer was washed with water (30 mL) and brine (30 mL). Dried over anhydrous Na₂SO₄. Removal of solvent gave brown solid (0.66 g) which was used in next step without further purification. The above solid (0.626 g, 1.58 mmol) and pyridine hydrochloride (1.18 g, 15.8 mmol) were mixed together and stirred at 190° C. for 20 min. Cooled to room temperature. Water (10 mL) was added, neutralized to pH ~9. The mixture was extracted with chloroform (2×100 mL). The organic layer was washed with brine (50 mL) and dried (Na₂SO₄). Removal of the solvent gave 2-(4-isopropoxy phenyl)-6-pyrrolidin-1-ylmethyl pyrano[2,3-b]pyridine-one (0.237 g, 41%) as yellow solid. To a solution of the above compound in anhydrous CH₂Cl₂ (10 mL) was added 1.0 M solution of hydrogen chloride in ether dropwise. The reaction mixture was stirred for 10 min. The solvent was removed under reduced pressure. The residue was washed with hexane and ether. Purified by triturating with 10% methanol in ether to give 2-(4-isopropoxyphenyl)-6-(pyrrolidin-1-ylmethyl)-4H-pyrano[2,3-b]pyridin-4-one hydrochloride (0.20 g, 83%) as yellow solid. MS (ES) m/z: 264 (M); MP 261-263° C.

Example 40

7-(4-hydroxy-3,5-dimethylphenyl)-1,6-naphthyridin-5(6H)-one hydrochloride

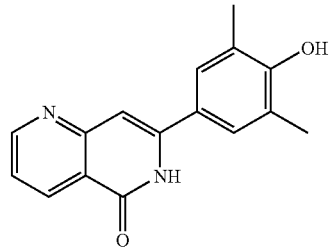 [SMILES: Cc1cc(-c2cc3ncccc3c(=O)[nH]2)cc(C)c1O]

Oxalyl chloride (1.90 mL, 21.8 mmol) was added to 2-methyl nicotinic acid (1.50 g, 10.9 mmol) in anhydrous dichloromethane (20 mL) with triethylamine (1.6 mL, 11.5 mmol) and the reaction mixture was kept at room temperature overnight and the solvent was removed. THF was added to the residue and ammonia gas was bubbled into for 2 hours. THF was removed and the residue was dissolved into methanol and water and adjusted pH to 10.0 by potassium carbonate and concentrated. After column chromatography the desired amide was isolated (1.10 g, 73.8%). NaH (0.428 g, 10.7 mmol, 60% in mineral oil) was added to 4-hydroxy-3,5-dimethylbenzonitrile (1.50 g, 10 mmol) in anhydrous DMF (8 mL) and then benzyl bromide (1.83 g, 10.7 mmol) was added and the reaction was kept at room temperature overnight. The reaction mixture was poured into water and filter the solid was further washed with hexane to yield the desired ether (2.0 g, 84.3%). It was used for next step reaction without further purification. The above amide (0.65 g, 4.77 mmol) in anhydrous THF (15 mL) was added dropwise to BuLi (7.5 mL, 1.60 M) at −20° C. The reaction mixture was kept at this temperature for one hour and then the above described ether (1.13 g, 4.77 mmol) in THF (20 mL) was added drop-wise at −20° C. and the reaction was further kept for 1.5 hours. The reaction temperature was increased to room temperature and kept for another hour. Water (20 mL) was added and the mixture was stirred for a while and the solvent was removed and the residue was purified by column to yield the desired intermediate (0.50 g, 29.4%). In a 50 mL flask was charged with the above described intermediate (0.50 g, 0.0014 mol) and pyridine hydrogen chloride (2.4 g, 0.014 mol) and the mixture was heated to 180° C. for 1.5 hour. The mixture was cooled and poured into methanol (4 mL) then filtered. The collected solid was further washed with ethyl acetate and dried to give 7-(4-hydroxy-3,5-dimethylphenyl)-1,6-naphthyridin-5(6H)-one (350 mg, 82.7%) as the hydrochloride salt; MS (ES) m/z: 266 (M); MP >350° C.

Example 41

2-hydroxy-7-(4-hydroxy-3,5-dimethylphenyl)-4-methoxy-1,6-naphthyridin-5(6H)-one dihydrochloride

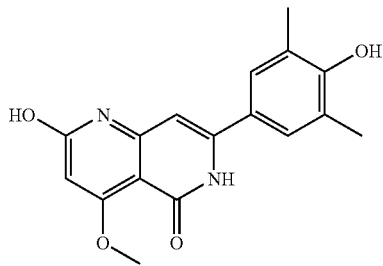 [SMILES: COc1cc(O)nc2cc(-c3cc(C)c(O)c(C)c3)[nH]c(=O)c12]

A mixture of malonic acid (20 g, 192 mmol), 2,4,6-trichlorophenol (72 g, 365 mmol), and phosphorus oxychloride (38 mL, 403.2 mmol) was stirred at reflux for 12 hours. The reaction mixture was cooled to 70° C. and poured into ice water. The solid was collected by filtration, washed with water, and air dried to give malonic acid bis-(2,4,6-trichlorophenyl) ester (85 g, 95%). A solution of malonic acid bis-(2,4,6-trichloro-phenyl) ester (85 g, 183.6 mmol) and ethyl 3-aminocrotonate (26.1 g, 202 mmol) in bromobenzene (100 mL) was stirred at reflux for 50 min. The reaction mixture was cooled to 50° C. and diluted with EtOAc (260 mL). The solid was collected by filtration, washed with water, and air dried to give 4,6-dihydroxy-2-methyl nicotinic acid ethyl ester (31 g, 86%).

A solution of 4,6-dihydroxy-2-methyl nicotinic acid ethyl ester (31 g, 157 mmol) in phosphorus oxychloride (60 mL, 629 mmol) was stirred at reflux for 1.5 hours. The extra phosphorus oxychloride was removed using a rotary evaporator and the reaction mixture was purred into icy water. The solid was removed by filtration. The filtrate was extracted with dichloromethane (3×100 mL), and concentrated using a rotary evaporator. The residue was further purified by column (SiO$_2$, Hexanes/EtOAc=5:1) to yield 4,6-dichloro-2-methyl nicotinic acid ethyl ester (16.9 g, 46%). A solution of 4,6-dichloro-2-methyl nicotinic acid ethyl ester (16.9 g, 71.3 mmol) in MeOH (60 mL) was mixed with sodium methoxide (58 mL, 257 mmol) and stirred at reflux for 12 hours. The reaction was quenched by adding AcOH (50 mL), diluted with water (200 mL), extracted with dichloromethane (3×100 mL), and concentrated using a rotary evaporator. The residue was further purified by column (SiO$_2$, Hexanes/EtOAc=6:1) to yield 4,6-dimethoxy-2-methyl nicotinic acid methyl ester (10 g, 67%). A solution of 4,6-dimethoxy-2-methyl nicotinic acid methyl ester (2.6 g, 12.3 mmol) and lithium hydroxide (1.0-6 g 44.1 mmol) in water (40 mL), MeOH (30 mL) and THF (20 mL) was stirred at reflux for 4 hours. The reaction mixture was concentrated using a rotary evaporator to dryness. The residue was mixed with HCl (conc.) (20 mL) and was concentrated again on high vacuum to dryness to yield crude 4,6-dimethoxy-2-methyl nicotinic acid (quantitative). To a solution of 4,6-dimethoxy-2-methyl nicotinic acid (2.5 g, 12.0 mmol) in dichloromethane (50 mL) and THF (50 mL) at room temperature was added oxalyl chloride (2.57 mL, 29.4 mmol) and DMF (3 drops). The reaction mixture was stirred at room temperature for 30 min, concentrated to dryness using a rotary evaporator to afford 4,6-dimethoxy-2-methyl nicotinic acid chloride HCl salt (2.8 g). A solution of 4,6-dimethoxy-2-methyl nicotinic acid chloride HCl salt (8.5 g, 33.73 mmol) in dichloromethane (20 mL) and THF (20 mL) at room temperature was mixed with methylamine in THF (50 mL, 98 mmol) and stirred at 20° C. for 1 hour. The reaction mixture was diluted with water (100 mL), extracted with dichloromethane (3×100 mL), and concentrated using a rotary evaporator to yield 4,6-dimethoxy-2,N-dimethyl-nicotinamide (4.2 g, 66%) as a light yellow solid. A solution of 4-hydroxy-3,5-dimethylbenzonitrile (2 g, 13.6 mmol) in DMF (20 mL) at room temperature was mixed with sodium hydride (0.706 g, 17.6 mmol) and stirred for 30 min. Benzyl bromide (1.62 mL, 13.59 mmol) was then added and the reaction mixture was stirred at room temperature for 24 hours. The reaction was quenched by adding water (200 mL), extracted with EtOAc (3×100 mL), and concentrated using a rotary evaporator. The residue was further purified by column (SiO$_2$, Hexanes/EtOAc=6:1) to yield 4-benzyloxy-3,5-dimethylbenzonitrile (3.25 g, 100%) as a white solid. To a solution of 4,6-dimethoxy-2,N-dimethyl-nicotinamide (0.54 g, 2.57 mmol) in THF (50 mL) at −20° C. was added n-BuLi (3.54 mL, 5.67 mmol). The reaction was stirred at −20° C.~0° C. for 2 hours and then was cooled to −78° C. At −78° C. 4-benzyloxy-3,5-dimethylbenzonitrile (0.49 g, 2.057 mmol) was added, the cooling bath was removed, and the reaction was allowed to warm up gradually to room temperature. After stirring at room temperature for 14 hours the reaction was quenched by adding water (100 mL), extracted with dichloromethane (×3×100 mL), and concentrated using a rotary evaporator. The residue was further purified by column (SiO$_2$, Hexanes/EtOAc=1:5) to yield 7-(4-benzyloxy-3,5-dimethylphenyl)-2,4-dimethoxy-6H-[1,6]naphthyridin-5-one (0.32 g, 37%). A solution of 7-(4-benzyloxy-3,5-dimethyl-phenyl)-2,4-dimethoxy-6H-[1,6]naphthyridin-5-one (0.25 g, 0.6 mmol) in dichloromethane (100 mL) was mixed with BBr$_3$ (3 mL, 3 mmol) and stirred at room temperature for 16 hours. The reaction was quenched by adding water (20 mL). The resulting solid was collected by filtration, washed with water and DCM to yield a light yellow solid. This solid was mixed with HCl in ether (10 mL, 10 mmol), stirred for 1 hour, filtered to afford 2-hydroxy-7-(4-hydroxy-3,5-dimethylphenyl)-4-

Example 42

3-(4-(2-hydroxy-2-methylpropoxy)-3,5-dimethylphenyl)-6,8-dimethoxyisoquinolin-1(2H)-one

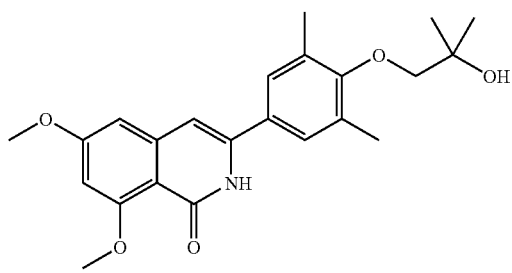 [SMILES: COc1cc(OC)c2c(=O)[nH]c(-c3cc(C)c(OCC(C)(C)O)c(C)c3)cc2c1]

To a solution of 4-hydroxy-3,5-dimethylbenzonitrile (2.00 g, 13.5 mmol) and 1-chloro-2-methyl propan-2-ol (8.85 g, 81.5 mmol) in ethanol (50 mL) was added potassium carbonate (7.5 g, 54 mmol) and water (5 mL). The reaction mixture was stirred at reflux for 24 hours. Cooled to room temperature. The precipitated solid was filtered off and washed with water. The solid was dissolved in ethyl acetate (100 mL), washed with water (50 mL), brine (50 mL) and dried over anhydrous $Na_2SO_4$. Removal of solvent gave 4-(2-hydroxy-2-methylpropoxy)-3,5-dimethyl benzonitrile (2.9 g, 97%) as a white solid. To a solution of 4-(2-hydroxy-2-methylpropoxy) 3,5-dimethyl benzonitrile (2.90 g, 13.2 mmol) in anhydrous DMF (20 mL) was added imidazole (2.7 g, 40 mmol) and tert-butyldimethylsilylchloride (2.19 g, 14.6 mmol). The reaction mixture was stirred at room temperature under nitrogen for 3 days. Water (200 mL) was added and the mixture was extracted with ethyl acetate (200 mL). The organic layer was washed with water (2×100 mL) and brine (100 mL), and dried over anhydrous $Na_2SO_4$. The solvent was removed under reduced pressure and the crude compound was purified by column chromatography (Silica Gel 230-400 mesh; 10% ethyl acetate in hexanes as eluent) to give 4[2-(tert-butyldimethylsilyloxy)-2-methylpropoxy]-3,5-dimethylbenzonitrile (2.24 g, 54%). n-Butyl lithium (6.2 mL, 6.6 mmol, 1.6 M solution in hexanes) was added to a solution of 2,4-dimethoxy-6-N-dimethylbenzamide (0.9 g, 4.3 mmol) in anhydrous THF (10 mL) dropwise at −10° C. over a period of 10 min under nitrogen. The stirring was continued at 0° C. for 1 hour. The reaction mixture was cooled to −50° C. A solution of 4-[2-(tert-butyldimethylsilanyloxy)-2-methylpropoxy]-3,5-dimethylbenzonitrile (1.58 g, 4.73 mmol) in anhydrous THF (5 mL) was quickly added. The cooling bath was removed and the reaction mixture was allowed to warm to room temperature. The stirring was continued at room temperature for 1 hour. Aqueous ammonium chloride solution (10 mL) was added. Ethyl acetate (100 mL) was added. The organic layer was separated, washed with water (10 mL) and dried ($Na_2SO_4$). The solvent was removed under reduced pressure and the crude compound was purified by column chromatography (Silica Gel 230-400 mesh; 0-5% methanol in $CH_2Cl_2$ as eluent) to give 3-{4-[2-(tert-butyldimethylsilanyloxy)-2-methylpropoxy]-3,5-dimethylphenyl}-6,8-dimethoxy-2H-isoquinolin-1-one (0.82 g, 37%) of as white solid. The above compound (0.42 g, 0.82 mmol) was dissolved in anhydrous THF (20 mL). Tetrabutyl ammonium fluoride (4.1 mL, 11.0M solution in THF) was added at 0° C. The reaction mixture was stirred at 0° C. for 10 min, then at room temperature for 2 h and then stirred at 70° C. for 24 hours. The mixture was cooled to room temperature. Saturated aqueous ammonium chloride (30 mL) was added. The organic phase was separated, washed with water, brine and dried over anhydrous $Na_2SO_4$. The solvent was removed under reduced pressure. The crude product was purified by column chromatography (Silica Gel 230-400 mesh; 0-4% methanol in $CH_2Cl_2$ as eluent) to give 3-(4-(2-hydroxy-2-methylpropoxy)-3,5-dimethylphenyl)-6,8-dimethoxyisoquinolin-1(2H)one (0.15 g, 46%) as a white solid. MS (ES) m/z: 398.96 (M+1); MP 252-254° C.

Example 43

2,6-dimethyl-4-(1-(methylamino)-7-((4-methylpiperazin-1-yl)methyl)isoquinolin-3-yl)phenol trihydrochloride

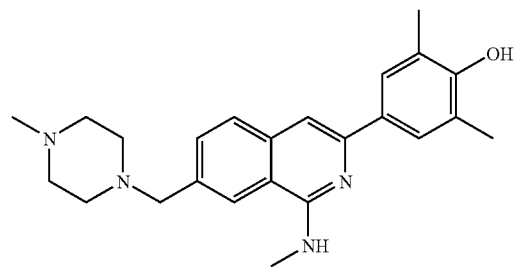

To a solution of 5-bromomethyl-2,N-dimethylbenzamide (4.94 g, 24 mmol) in anhydrous THF (75 mL) was added N-methylpiperazine (5.3 mL, 4.81 g, 48 mmol). A white precipitate was formed. Stirring continued overnight. Water (100 mL) was added, and the mixture was extracted with ethyl acetate (200 mL). The organic layer was washed with brine and dried over anhydrous $Na_2SO_4$. Purification by column chromatography (Silica Gel 230-400 mesh; 0-5% methanol (containing 7.0 M ammonia) in $CH_2Cl_2$ as eluent) to give 2,N-dimethyl-5-(4-methylpiperazin-1-ylmethyl)benzamide (2.4 g, 38%) of as a gummy material. n-Butyl lithium (9.1 mL, 14.64 mmol, 1.6 M solution in hexanes) was added to a solution of 2,N-dimethyl-5-(4-methylpiperazin-1-ylmethyl)benzamide (0.87 g, 3.33 mmol) in anhydrous THF (10 mL) dropwise at −10° C. over a period of 10 min under nitrogen. Color changed to orange-red. Stirring continued at 0° C. for 1 hour. The reaction mixture was cooled to −50° C. A solution of 4-(tert-butyldimethylsilanyloxy)-3,5-dimethylbenzonitrile (1.09 g, 4.16 mmol) in anhydrous THF (5 mL) was quickly added. Cooling bath was removed and the reaction mixture was allowed to warm to room temperature. Stirring was continued at room temperature for 1 hour. The reaction mixture became dark colored. An aqueous ammonium chloride solution (20 mL) was added. The color changed to pale yellow. Ethyl acetate (50 mL) was added. The organic layer was separated, washed with water (10 mL) and dried ($Na_2SO_4$). Removal of the solvent gave a yellow gummy material, which was used in next step without further purification. The above compound (1.87 g) was dissolved in anhydrous THF (10 mL). Tetrabutyl ammonium fluoride (6.8 mL, 1.0M solution in THF) was added at 0° C. The reaction mixture was stirred at 0° C. for 30 min. and then at room temperature for 1 hour. Saturated aqueous ammonium chloride (30 mL) was added. The mixture was extracted with ethyl acetate (100 mL) and the organic layer was separated and dried over anhydrous Na$_2$SO$_4$. The solvent was removed under reduced pressure, the crude product was purified by column chromatography (Silica Gel 230-400 mesh; 0-5% methanol (containing 7.0 M ammonia) in CH$_2$Cl$_2$ as eluent) to give 2,6-dimethyl-4-[1-methylamino-7-(4-methylpiperazin-1-ylmethyl) isoquinolin-3-yl]phenol (0.487 g, 33%) as purple solid. To a solution of above compound (0.17 g, 0.43 mmol) in CH$_2$Cl$_2$ (10 mL) was added hydrogen chloride in ether (2.0 mL, 1.0 M solution) dropwise under nitrogen. A yellow precipitate was formed. The reaction mixture was stirred at room temperature for 11 hour. Solvent was removed under reduced pressure and dried under vacuum to give 2,6-dimethyl-4-(1-(methylamino)-7-((4-methylpiperazin-1-yl) methyl)isoquinolin-3-yl)phenol (0.178 g, 97%) as the trihydrochloride; MS (ES) m/z: 391.10 (M+1); MP 264-266° C.

Example 44

2-(quinoxalin-6-yl)-4H-pyrano[2,3-b]pyridin-4-one

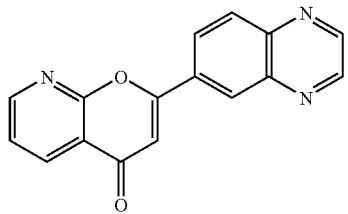 [SMILES: O=c1cc(-c2ccc3nccnc3c2)oc2ncccc12]

A mixture of quinoxaline-6-carboxylic acid (2 g, 11.49 mmol) and thionyl chloride (30 mL) was stirred at reflux for 2 hours. The reaction mixture was concentrated to dryness using a rotary evaporator to afford quinoxaline-6-carboxylic acid chloride (crude quantitative). A solution of the above acid chloride (11.49 mmol) in DCM (50 mL) and pyridine (20 mL) was mixed with N,O-dimethyl hydroxylamine HCl salt (2.24 g, 23 mmol) and stirred at room temperature for 12 hours. The reaction was quenched by adding aqueous HCl (50 mL, 1 N), extracted with DCM (3×100 mL), concentrated using a rotary evaporator. The residue was further purified by column (SiO$_2$, Hexanes/EtOAc=1:3) to yield quinoxaline-6-carboxylic acid methoxy-methyl-amide (2 g, 80%). To a solution of the above Weinreb amide (2.0 g, 9.2 mmol) in THF (30 mL) at 0° C. was added methyl magnesium bromide (3.9 mL, 11.6 mmol). The reaction mixture was stirred at 0° C. for 2 hours and then 1 hour at room temperature, quenched by adding aqueous HCl (20 mL, 1 N), extracted with DCM (3×100 mL), concentrated using a rotary evaporator. The residue was further purified by column (SiO$_2$, Hexanes/EtOAc=1:3) to yield 6-acetylquinoxaline (1.17 g, 74%). A solution of 2-chloronicotinic acid ethyl ester (5.0 g, 27 mmol) in MeOH (25 mL) was mixed with sodium methoxide (25.6 mL, 112.5 mmol) and stirred at reflux for 12 hours. The reaction was quenched by adding water (100 mL), extracted with DCM (3×100 mL), concentrated using a rotary evaporator to afford 2-methoxynicotinic acid methyl ester (3.2 g, 71%). A solution of 6-acetylquinoxaline (0.62 g, 3.6 mmol), 2-methoxynicotinic acid methyl ester (0.64 g, 3.8 mmol), and sodium hydride (0.46 g, 11.4 mmol) in THF (100 mL) was stirred at room temperature for 16 hours. The reaction was quenched by adding water (100 mL) and AcOH (20 mL), extracted with dichloromethane (3×100 mL), and concentrated using a rotary evaporator. The residue was re-dissolved in DCM (5 mL) and MeOH (3 mL) and was diluted with Hexanes (50 mL). The solid was removed by filtration and the filtrate was concentrated to afford the diketo compound (0.7 g, 60%). A solution of the above diketone (0.4 g, 1.3 mmol) in AcOH (50 mL) and sulfuric acid (conc., 15 drops) was stirred at reflux for 1 hour. Most of the solvent was removed using a rotary evaporator. The residue was re-dissolved in MeOH and neutralized with potassium carbonate to pH=8. The solid residue was removed by filtration, washed with MeOH and DCM. The filtrate was extracted with CH$_2$Cl$_2$ (3×100 mL) and concentrated using a rotary evaporator. The solid residue was purified by column (SiO$_2$, Hexanes/EtOAc/MeOH=2:2:1) to afford 2-(quinoxalin-6-yl)-4H-pyrano[2,3-b]pyridin-4-one (90 mg, 24%); MS (ES) m/z: 276 (M+1); MP 272.3-274.8° C.

Example 45

4-(5-amino-2,4-dimethoxy-1,6-naphthyridin-7-yl)-2,6-dimethylphenol

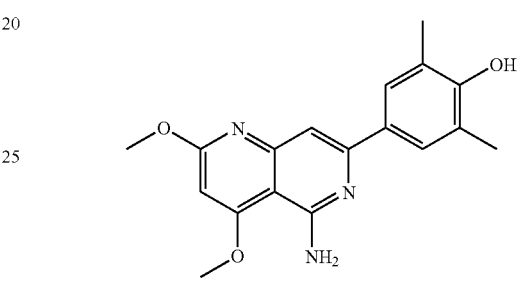

A mixture of malonic acid (20 g, 192 mmol), 2,4,6-trichlorophenol (72 g, 365 mmol), and phosphorus oxychloride (38 mL, 403.2 mmol) was stirred at reflux for 12 hours. The reaction mixture was cooled to 70° C. and poured into icy water. The solid was collected by filtration, washed with water, and air dried to give malonic acid bis-(2,4,6-trichlorophenyl) ester (85 g, 95%). A solution of malonic acid bis-(2,4,6-trichloro-phenyl) ester (85 g, 184 mmol) and ethyl 3-aminocrotonate (26.08 g, 202 mmol) in bromobenzene (100 mL) was stirred at reflux for 50 min. The reaction mixture was cooled to 50° C. and diluted with EtOAc (260 mL). The solid was collected by filtration, washed with water, and air dried to give 4,6-dihydroxy-2-methyl nicotinic acid ethyl ester (31 g, 86%). A solution of 4,6-dihydroxy-2-methyl nicotinic acid ethyl ester (31.0 g, 157 mmol) in phosphorus oxychloride (60.0 mL, 629 mmol) was stirred at reflux for 1.5 hours. The extra phosphorus oxychloride was removed using a rotary evaporator and the reaction mixture was poured into icy water. The solid was removed by filtration. The filtrate was extracted with dichloromethane (3×100 mL), and concentrated using a rotary evaporator. The residue was further purified by column (SiO$_2$, Hexanes/EtOAc=5:1) to yield 4,6-dichloro-2-methyl nicotinic acid ethyl ester (16.9 g, 46%). A solution of 4,6-dichloro-2-methyl nicotinic acid ethyl ester (16.9 g, 71.3 mmol) in MeOH (60 mL) was mixed with sodium methoxide (58 mL, 257 mmol) and stirred at reflux for 12 hours. The reaction was quenched by adding AcOH (50 mL), diluted with water (200 mL), extracted with dichloromethane (3×100 mL), and concentrated using a rotary evaporator. The residue was further purified by column (SiO$_2$, Hexanes/EtOAc=6:1) to yield 4,6-dimethoxy-2-methyl nicotinic acid methyl ester (10 g, 67%). A solution of 4,6-dimethoxy-2-methyl nicotinic acid methyl ester (2.6 g, 12.3 mmol) and lithium hydroxide (1.06 g, 44.1 mmol) in water (40 mL), MeOH (30 mL) and THF (20 mL) was stirred at reflux for 4 hours. The reaction mixture was concentrated using a rotary evaporator to dryness. The residue was mixed with conc. HCl (20 mL) and was concentrated again on high vacuum to dryness to yield crude 4,6-dimethoxy-2-methyl nicotinic acid. To a solution of 4,6-dimethoxy-2-methyl nicotinic acid (2.5 g, 12.0 mmol) in dichloromethane (50 mL) and THF (50 mL) at room temperature was added oxalyl chloride (2.57 mL, 29.4 mmol) and DMF (3 drops). The reaction mixture was stirred at room temperature for 30 min., concentrated to dryness using a rotary evaporator to afford crude 4,6-dimethoxy-2-methyl nicotinic-acid chloride HCl salt (2.8 g). A solution of 4,6-dimethoxy-2-methyl nicotinic acid chloride HCl salt (4.8 g, 23.5 mmol) in dichloromethane (100 mL) at room temperature was poured in to a beaker of ammonium hydroxide (200 mL). The reaction mixture was stirred at room temperature for 1 hour, extracted with dichloromethane (3×100 mL), and concentrated using a rotary evaporator to yield 4,6-dimethoxy-2-methyl-nicotinamide (2.4 g, 52%) as a light yellow solid. A solution of 4-hydroxy-3,5-dimethyl-benzonitrile (2 g, 13.6 mmol) in DMF (20 mL) at room temperature was mixed with sodium hydride (0.706 g, 17.6 mmol) and stirred for 30 min. Benzyl bromide (1.62 mL, 13.6 mmol) was then added and the reaction mixture was stirred at room temperature for 24 hours. The reaction was quenched by adding water (200 mL), extracted with EtOAc (3×100 mL), and concentrated using a rotary evaporator. The residue was further purified by column (SiO$_2$, Hexanes/EtOAc=6:1) to yield 4-benzyloxy-3,5-dimethylbenzonitrile (3.25 g, 100%) as a white solid. To a solution of 4,6-dimethoxy-2-methyl-nicotinamide (1 g, 5.1 mmol) in THF (120 mL) at −20° C. was added n-BuLi (9.6 mL, 15.3 mmol). The reaction was stirred at −20° C.-0° C. for 2.5 hours and then was cooled to −78° C. At −78° C. 4-benzyloxy-3,5-dimethylbenzonitrile (1.21 g, 5.1 mmol) was added, the cooling bath was removed, and the reaction was allowed to warm up gradually to room temperature. After stirring at room temperature for 20 hours the reaction was quenched by adding water (100 mL), extracted with dichloromethane (3×100 mL), and concentrated using a rotary evaporator. The residue was further purified by column (SiO$_2$, Hexanes/EtOAc/MeOH 3:2:1) to yield 7-(4-benzyloxy-3,5-dimethyl-phenyl)-2,4-dimethoxy-[1,6]naphthyridin-5-ylamine (0.4 g, 19%) and 7-(4-benzyloxy-3,5-dimethyl-phenyl)-2,4-dimethoxy-6H-[1,6]naphthyridin-5-one (0.34 g, 16%). A solution of 7-(4-benzyloxy-3,5-dimethyl-phenyl)-2,4-dimethoxy-[1,6]naphthyridin-5-ylamine (0.4 g, 0.96 mmol) in DMF (100 mL) and MeOH (50 mL) was mixed with palladium/carbon (0.1 g) and subjected to hydrogenation (50 psi) for 2 hours. The mixture was filtered through a celite-pad. The filtrate was concentrated on high vacuum to afford 4-(5-amino-2,4-dimethoxy-1,6-naphthyridin-7-yl)-2,6-dimethylphenol (0.31 g, 100%); MS (ES) m/z: 326 (M+1); MP 163.2-165.5° C.

Example 46

2-(4-fluorophenyl)-6-(morpholinomethyl)quinazolin-4(3H)-one

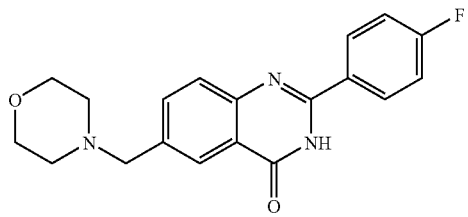 [SMILES: O=c1[nH]c(-c2ccc(F)cc2)nc2ccc(CN3CCOCC3)cc12]

A mixture of 2-amino-5-methylbenzamide (1.0 g, 6.7 mmol), 4-fluorobenzaldehyde (0.83 g, 6.7 mmol), iodine (2.03 g, 8.0 mmol), and potassium carbonate (1.38 g, 10 mmol) in DMF (50 mL) was stirred at 80° C. for 16 hours. The reaction mixture was cooled to 20° C. and poured into icy water. The solid was collected by filtration, washed with water, and air dried to give 2-(4-fluoro-phenyl)-6-methyl-3H-quinazolin-4-one (1.41 g, 83%). A solution of 2-(4-fluoro-phenyl)-6-methyl-3H-quinazolin-4-one (1.4 g, 5.5 mmol), NBS (0.98 g, 5.6 mmol), and benzoyl peroxide (67.0 mg, 0.276 mmol) in AcOH (150 mL) and chloroform (150 mL) was stirred at 80° C. for 5 hours with light shedding on. The reaction mixture was cooled to 20° C. and concentrated using a rotary evaporator to yield the crude bromide. A solution of the above crude bromide in DMF (20 mL) and 1,4-dioxane (100 mL) was mixed with morpholine (10 mL) and stirred at 80° C. for 4 hours. The reaction was quenched by adding water (200 mL), extracted with dichloromethane (3×100 mL), and concentrated using a rotary evaporator. The residue was further purified by column (SiO$_2$, Hexanes/EtOAc/MeOH=4:3:1) to yield 2-4-fluoro-phenyl)-6-morpholin-4-ylmethyl-3H-quinazolin-4-one (0.89 g, 48% over two steps). A solution of 2-(4-fluoro-phenyl)-6-morpholin-4-ylmethyl-3H-quinazolin-4-one (0.89 g, 2.62 mmol) in dichloromethane (100 mL) and MeOH (50 mL) was mixed with HCl in ether (8 mL, 16 mmol) and stirred for 1 hour. The reaction was concentrated using a rotary evaporator. The solid was rinsed with DCM (50 mL) and MeOH (5 mL), collected by filtration, washed with DCM-MeOH (10:1) to afford 2-(4-fluorophenyl)-6-(morpholinomethyl)quinazolin-4(3H)-one (0.82 g, 76%) as an off-white solid; MS (ES) m/z: 340 (M+1); MP 321.8-323.3° C.

Example 47

2-(1H-indazol-5-yl)-6-(morpholinomethyl)-4H-pyrano[2,3-b]pyridin-4-one

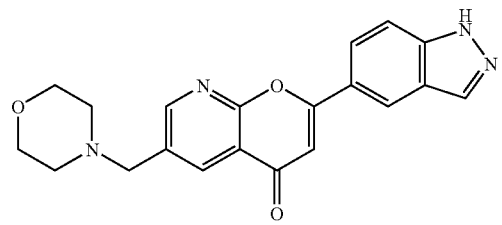 [SMILES: O=c1cc(-c2ccc3[nH]ncc3c2)oc2ncc(CN3CCOCC3)cc12]

Methyl 2-methoxy-5-(morpholinomethyl)nicotinate (0.413 g, 1.55 mmol) and 1-(2-(4-methoxybenzyl)-2H-indazol-5-yl)ethanone (0.436 g, 1.55 mmol) were dissolved in anhydrous DMF (5 mL) under nitrogen. Sodium hydride (0.093 g, 2.3 mmol) was added with stirring at room temperature. The color of the reaction mixture changed from colorless to brown to orange. The reaction mixture was stirred at room temperature overnight before pouring into water (100 mL), adjusted pH ~7 by adding acetic acid. The mixture was stirred for an hour and the solid (0.1 g) was filtered off, washed with water and hexane. The mother liquor was extracted with ethyl acetate, evaporated and dried. The two solids were combined and purified by silica gel (50 g) column chromatography employing 2-5% methanol in dichloromethane as eluents to give the desired diketo compound (0.2704 g). The diketo compound (0.270 g, 0.525 mmol) was taken in a round bottomed flask. Glacial acetic acid (50 mL) was added, followed by conc. HCl (2 mL). The reaction mixture was refluxed for 2 hours (bath temp. 130° C.). Acetic acid was evaporated in vacuo and methanol was added. The solvent was removed in vacuo, water was added, basified with NaHCO$_3$ and extracted with ethyl acetate. The solvent was evaporated in vacuo to leave a crude product (0.218 g, 86%) which was used for the next step without further purification. The compound from above (0.218 g, 0.45 mmol) was taken into trifluoroacetic acid (10 mL) and the reaction mixture was refluxed (bath temperature 80° C.) for 24 hours. The solvent was evaporated in vacuo and the residue was dissolved in NaOH (20 mL, 0.25 N), acidified with acetic acid. The formed solid was filtered off and washed with water and hexane. This impure material was further purified by silica gel (25 g) column chromatography employing 2-5% methanol in hexane/ethyl acetate as eluents to give the desired intermediate (0.2359 g). The above compound was dissolved in 5% methanol in dichloromethane. A solution of hydrogen chloride in diethyl ether was added dropwise. The flask was kept standing for 0.5 h and the solid was filtered off and dried to give 2-(1H-indazol-5-yl)-6-(morpholinomethyl)-4H-pyrano[2,3-b]pyridin-4-one (0.1217 g, 34%). MS (ES) m/z: 363 (M+1); MP 293.1-293.2° C.

Example 48

3-(3,5-dimethyl-4-(2-morpholinoethoxy)phenyl)-6,8-dimethoxyisoquinolin-1(2H)-one

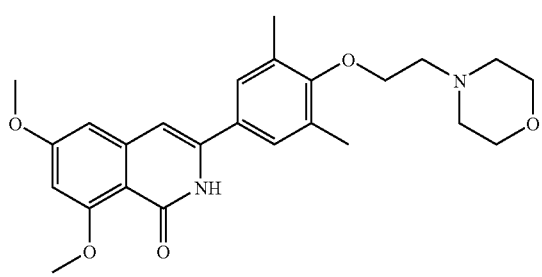 [SMILES: COc1cc(OC)c2c(=O)[nH]c(-c3cc(C)c(OCCN4CCOCC4)c(C)c3)cc2c1]

(3,5-Dimethoxy-phenyl)-acetic acid (10.0 g, 50.96 mmol) was dissolved in anhydrous methanol (100 mL) and H$_2$SO$_4$ (1 mL) was added dropwise. The reaction mixture was refluxed overnight. Cooled to room temperature. The solvent was removed and the residue was dissolved in ethyl acetate and washed with a saturated aqueous NaHCO$_3$ solution, water and dried (Na$_2$SO$_4$). The solvent was evaporated in vacuo to obtain (3,5-dimethoxy-phenyl)-acetic acid methyl ester (10.4 g, 97%). To a solution of (3,5-dimethoxy-phenyl)-acetic acid methyl ester (10.4 g, 49.5 mmol) in dimethyl formamide (40 mL), POCl$_3$ (5.4 mL, 59.4 mmol) was added at 55° C. After the addition, the reaction mixture was heated at 100° C. for 10 min. and then stirred at room temperature overnight. The reaction mixture was poured into ice-water and extracted with ethyl acetate, washed with water, brine, dried over anhydrous Na$_2$SO$_4$ and evaporated in vacuo to obtain (2-formyl-3,5-dimethoxy-phenyl)-acetic acid methyl ester (10.0 g, 85%). (2-Formyl-3,5-dimethoxy-phenyl)-acetic acid methyl ester (5.0 g, 21.0 mmol) was dissolved in CH$_3$CN (100 mL), NaH$_2$PO$_4$ (0.655 g, 5.46 mmol) in water (2 mL) and H$_2$O$_2$ (2.3 mL, 20.99 mmol, 30%) were added. The reaction mixture was cooled to 0° C. and a solution of NaO$_2$Cl (2.65 g, 29.4 mmol) in water (5 mL) was added slowly. The reaction mixture was stirred at room temperature for 4' hours before being quenched by the addition of Na$_2$SO$_3$ solution. The mixture was acidified with 2 N HCl and extracted with ethyl acetate. The solvent was evaporated in vacuo to obtain 2,4-dimethoxy-6-methoxycarbonylmethyl-benzoic acid (5.25 g, 98%). To a solution of 2,4-dimethoxy-6-methoxycarbonylmethyl-benzoic acid (5.25 g, 20.6 mmol) in methanol (50 mL), a solution of NaOH (4.12 g, 103 mmol) in water (20 mL) was added and the reaction mixture was allowed to stir at room temperature for 3 hours. The solvent was removed, diluted with water and acidified with 2 N HCl. The compound was extracted with ethyl acetate, washed with water, brine, dried over anhydrous Na$_2$SO$_4$ and evaporated in vacuo to obtain 2-carboxymethyl-4,6-dimethoxy-benzoic acid (4.65 g, 94%). To a suspension of 2-carboxymethyl-4,6-dimethoxy-benzoic acid (4.65 g, 19.36 mmol) in toluene (50 mL) and acetic anhydride (2.01 mL, 21.3 mmol) were refluxed for 2 hours. After cooling to 0° C., the precipitated solid was filtered off and washed with heptane and hexane to obtain 6,8-dimethoxy-isochroman-1,3-dione (3.56 g, 83%).

To a solution of 3,5-dimethylhydroxy-benzoic acid (3.0 g, 18.05 mmol) in pyridine (7 mL), acetic anhydride (2.05 mL, 21.66 mmol) was added and the reaction mixture was stirred at room temperature for 16 hours. Water was added and the compound was extracted with ethyl acetate, washed with water, brine and dried over anhydrous Na$_2$SO$_4$. The solvent was evaporated in vacuo to obtain 4-acetoxy-3,5-dimethyl-benzoic acid (3.52 g, 94%). To a solution of 4-acetoxy-3,5-dimethyl-benzoic acid (6.02 g, 28.91 mmol) in CH$_2$Cl$_2$ (80 mL), oxalyl chloride (5.04 mL, 57.83 mmol) was added slowly, followed by a drop of dimethylformamide. The reaction mixture was stirred at room temperature for 2 hours. The solvent was removed and the solid acid chloride was dried under vacuum (6.37 g, 97%). To a solution of N,N,N,N-tetramethyl guanidine (2.77 mL, 22.078 mmol) in CH$_3$CN (50 mL), a solution of 6,8-dimethoxy-isochroman-1,3-dione (4.46 g, 20.1 mmol) in CH$_3$CN (100 mL) was added slowly at <0° C. (bath temperature −20° C.) over 30 min. Et$_3$N (1 eq.) was added in one portion, followed by a solution of acetic acid 4-chlorocarbonyl-2,6-dimethyl-phenyl ester (6.37 g, 28.1 mmol) in CH$_3$CN (50 mL) and stirred for 30 min. at <0° C. The reaction mixture was stirred at room temperature for 16 hour before being refluxed for 3 hour. After cooling to room temperature, the reaction mixture was quenched with 1 N HCl. The precipitated solid was filtered off to give a mixture of acetic acid 4-(6,8-dimethoxy-1,3-dioxo-isochroman-4-carbonyl-2,6-dimethyl-phenyl ester and acetic acid 4-(6,8-dimethoxy-1-oxo-1H-isochromen-3-yl)-2,6-dimethyl-phenyl ester (combined 6.0 g). The above mixture of compounds (6.0 g) was dissolved in 30% H$_2$SO$_4$ (30 mL) and heated at 100° C. for 2 hours. The reaction mixture was cooled to room temperature and the precipitated solid was filtered off to obtain a mixture of acetic acid 4-(6,8-dimethoxy-1-oxo-1H-isochromen-3-yl-2,6-dimethyl-phenyl ester and 3-(4-hydroxy-3,5-dimethyl-phenyl)-6,8-dimethoxy-isochromen-1-one (5.5 g). The above mixture (5.5 g) was dissolved in methanol (30 mL) and K$_2$CO$_3$ (3.09 g, 22.4 mmol) and water (10 mL) were added. The reaction mixture was stirred at room temperature for 6 hours. The solvent was removed and the mixture was acidified with diluted HCl. The compound was extracted with ethyl acetate, washed with water, brine and dried over anhydrous Na$_2$SO$_4$. The solvent was evaporated in vacuo to leave a residue which was purified by chromatography (Silica Gel, 230-250 mesh; 2% methanol in dichloromethane) to obtain 3-(4-hydroxy-3,5-dimethyl-phenyl)-6,8-dimethoxy-isochromen-1-one (1.46 g). To a solution of compound 3-(4-hydroxy-3,5-dimethyl-phenyl)-6,8-dimethoxy-isochromen-1-one (0.875 g, 2.68 mmol) in DMF (5 mL), NaH (0.129 g, 3.22 mmol) was added and the mixture was stirred for 1 hour. To the reaction mixture was added 1-chloro-2-iodo-ethane (1.23 mL, 13.4 mmol) and the mixture was stirred at room temperature for 16 hour. The reaction mixture was heated at 80° C. before being quenched with 1 N HCl at room temperature. The crude was purified by column chromatography (Silica Gel, 230-250 mesh; 2% methanol in dichloromethane) to give 3-[4-(2-chloro-ethoxy)-3,5-dimethyl-phenyl]-6,8-dimethoxy-isochromen-1-one (0.36 g, 35%). The compound 3-[4-(2-chloro-ethoxy)-3,5-dimethyl-phenyl]-6,8-dimethoxy-isochromen-1-one (0.36 g, 0.93 mmol) was dissolved in DMSO (5 mL) and morpholine (0.4 mL, 4.63 mmol) and Et₃N (0.64 mL, 4.63 mmol) were added. The reaction mixture was heated at 110 C for 16 h before being cooled to room temperature. Water was added and the compound was extracted with ethyl acetate. The solvent was evaporated in vacuo to leave a residue which was purified by chromatography (Silica Gel, 230-250 mesh) to give 3-[3,5-dimethyl-4-(2-morpholin-4-yl-ethoxy)-phenyl]-6,8-dimethoxy-isochromen-1-one (0.13 g, 31%). The compound 3-[3,5-dimethyl-4-(2-morpholinyl-ethoxy)-phenyl]-6,8-dimethoxy-isochromen-1-one (0.13 g, 0.29 mmol) and NH₃ (2.0 M solution in ethanol, 30 mL), were mixed in a steel bomb and heated at 130° C. for 16 hours. The solvent was removed and the crude compound was purified by chromatography (Silica Gel, 230-250 mesh). The compound was then converted into a salt by treatment with HCl in ether to give 3-(3,5-dimethyl-4-(2-morpholinoethoxy)phenyl)-6,8-dimethoxyisoquinolin-1(2H)-one (80 mg, 59%); MS (ES) m/z: 349 (M+1); MP 196-198° C.

Example 49

5-methyl-2-(pyridin-yl)-4H-chromen-4-one

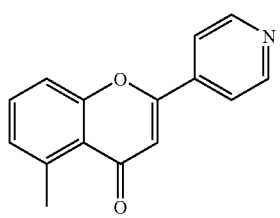 [SMILES: Cc1cccc2oc(-c3ccncc3)cc(=O)c12]

In a solution of 2-methoxy-6-methylbenzoic acid ethyl ester (5 g, 25.77 mmol) and NaOH (6.18 g, 154.64 mmol) in EtOH (100 mL) and water (40 mL) was stirred at reflux for 24 hours. EtOH was then removed using a rotary evaporator and the aqueous was acidified with HCl (1 N) to pH=4. Extract with CH₂Cl₂ (3×100 mL) followed by concentration using a rotary evaporator afforded 4.25 g, of 2-methoxy-6-methylbenzoic acid (100%) as a white solid. To a solution of 2-methoxy-6-methylbenzoic acid (1.66 g, 10 mmol) in CH₂Cl₂ (80 mL) at room temperature was added BBr₃ in CH₂Cl₂ (20 mL, 20 mmol). The reaction mixture was stirred at room temperature for 20 hour and then concentrated using a rotary evaporator. The resulting residue was re-dissolved in CH₂Cl₂ (50 mL), diluted with HCl (0.5 N), extracted with CH₂Cl₂ (3×100 mL) and concentrated using a rotary evaporator to afford 1.52 g of 2-hydroxy-6-methylbenzoic acid (100%). To a solution of 2-hydroxy-6-methylbenzoic acid (1.52 g, 10 mmol) in THF (50 mL) at room temperature was slowly added CH₃Li in ether (22 mL, 35 mmol) and the suspension was stirred at 60° C. for 6 hour. The reaction was quenched with HCl (0.5 N) aqueous and extracted with CH₂Cl₂ (3×100 mL). Concentration using a rotary evaporator afforded 1 g of 2'-hydroxy-6'-methylacetophenone (67%) as a brown oil. A solution of 2'-hydroxy-6'-methylacetophenone (1.0 g, 6.67 mmol) in CH₂Cl₂ (50 mL) at room temperature was mixed with isonicotinoyl chloride hydrochloride (2.136 g, 12 mmol) and triethylamine (3.9 mL, 28 mmol) sequentially. The resulting mixture was stirred at room temperature for 2 hours, quenched with water, and extracted with CH₂Cl₂ (3×100 mL) The volume was reduced using a rotary evaporator to minimal and triturated with hexanes. The solid was collected by filtration to afford 1.2 g of the corresponding isonicotinic aryl ester (70%). A solution of the above isonicotinic aryl ester (1.2 g, 4.70 mmol) in THF (50 mL) was mixed with potassium tert-butoxide (2.24 g, 20 mmol) and stirred at 65° C. for 2hours. The reaction was quenched with water and acidified with HCl (0.5 N) to pH=6. Extract with CH₂Cl₂ (3×100 mL) followed by concentration using a rotary evaporator afforded a yellow solid residue. It was purified by column (SiO₂, hexane/EtOAc=1:1) to provide 0.72 g of the diketone (60%). A solution of the above diketone (0.7 g, 2.745 mmol) in HOAc (50 mL) was stirred at reflux for 2 hours. All the solvent was removed using a rotary evaporator to afford a solid residue. It was then diluted with water and neutralized with NaOH (0.5 N) to pH=8. The solid was collected by filtration and washed with water and hexanes sequentially to afford 0.32 g of 5-methyl-2-(pyridin-4-yl)-4H-chromen-4-one as a light yellow solid (49%).

Example 50

6-((dimethylamino)methyl)-2-(pyridinyl)-4H-chromen-4-one

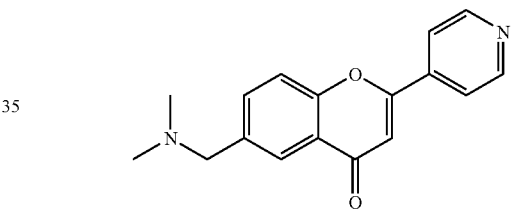

In a solution of 2'-hydroxyacetophenone (10 g, 73.53 mmol) in 12 N HCl (160 mL) at room temperature was mixed with paraformaldehyde (2.43 g, 80.88 mmol) and stirred at 40° C. for 8 hours. The reaction was diluted with water, extracted with CH₂Cl₂ (3×100 mL), and concentrated using a rotary evaporator to provide 13 g of 5'-chloromethyl-2'-hydroxyacetophenone (98%). To a solution of 5'-chloromethyl-2'-hydroxyacetophenone (4 g, 21.74 mmol) in THF (50 mL) at room temperature was added dimethylamine in THF (13 mL, 26 mmol). The reaction mixture was stirred at 60° C. for 6 hours. It was quenched with water and neutralized with potassium carbonate to pH=8. Extract with CH₂Cl₂ (3×100 mL) followed by concentration using a rotary evaporator provided 3.86 g of 5'-(N,N-dimethylaminomethy)-2'-hydroxyacetophenone (92%). A solution of 5'-(N,N-dimethylaminomethy)-2'-hydroxyacetophenone (1.4 g, 7.25 mmol) and ethyl isonicotinate (1.1 g, 7.25 mmol) in THF (100 mL) at room temperature was mixed with NaH (1.02 g, 25.375 mmol) and was stirred at reflux for 6 hours. The reaction was quenched with water and extracted with CH₂Cl₂ (3×100 mL). The volume was reduced using a rotary evaporator to minimal and triturated with hexanes. The solid was collected by filtration to afford 1.85 g of the corresponding diketone (86%). A solution of the above diketone (1.85 g, 26.19 mmol) in HOAc (100 mL) was stirred at reflux for 2 hours. All the solvent was removed using a rotary evaporator to afford a solid residue. It was then re-dissolved in CH₂Cl₂, diluted with water and neutralized with potassium carbonate to pH=8, extracted with CH₂Cl₂ (3×100 mL) and concentrated using a rotary evaporator The solid residue was purified by column (SiO2, hexanes/EtOAc/MeOH=2:2:1) to afford 1.4 g of the intermediate (80%). A solution of the above intermediate (0.7 g, 2.34 mmol) in CH₂Cl₂ (20 mL) was mixed with HCl in ether (10 mL, 20 mmol) and stirred at room temperature for 30 min. The solid was collected by filtration and washed with CH₂Cl₂ and MeOH sequentially to obtain 0.48 g of the 6-((dimethylamino)methyl)-2-(pyridin-4-yl)-4H-chromen-4-one hydrochloride (60%) as an off-white solid.

Example 51

5-(hydroxymethyl)-2-(pyridin-4-yl)-4H-chromen-4-one

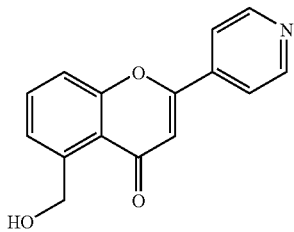

In a solution of 2-methoxy-6-methylbenzoic acid ethyl ester (5 g, 25.77 mmol) and NaOH (6.18 g, 154.64 mmol) in EtOH (100 mL) and water (40 mL) was stirred at reflux for 24 hours. EtOH was then removed using a rotary evaporator and the aqueous was acidified with HCl (1 N) to pH=4. Extract with CH₂Cl₂ (3×100 mL) followed by concentration using a rotary evaporator afforded 4.25 g of 2-methoxy-6-methylbenzoic acid (100%) as a white solid. To a solution of 2-methoxy-6-methylbenzoic acid (3.5 g, 21 mmol) in CH₂Cl₂ (100 mL) at room temperature was added BBr₃ in CH₂Cl₂ (42 mL, 42 mmol). The reaction mixture was stirred at room temperature for 14 hrs and then concentrated using a rotary evaporator. The resulting residue was re-dissolved in CH₂Cl₂ (50 mL), diluted with HCl (0.5 N), extracted with CH₂Cl₂ (3×100 mL) and concentrated using a rotary evaporator to afford 3.3 g of 2-hydroxy-6-methylbenzoic acid (100%). To a solution of 2-hydroxy-6-methylbenzoic acid (3.3 g, 21.7 mmol) in THF (200 mL) at room temperature was slowly added CH₃Li in ether (47 mL, 76 mmol) and the suspension was stirred at 60° C. for 6 hour. The reaction was quenched with HCl (0.5 N) aqueous and extracted with CH₂Cl₂ (3×100 mL). Concentration using a rotary evaporator afforded an oily residue. It was purified by column (SiO₂, hexane/EtOAc=4:1) to provide 3 g of 2'-hydroxy-6'-methylacetophenone (92%) as a light yellow oil. A solution of 2'-hydroxy-6'-methylacetophenone (1.5 g, 10 mmol) in CH₂Cl₂ (50 mL) at room temperature was mixed with isonicotinoyl chloride hydrochloride (2.0 g, 11 mmol) and triethylamine (4.9 mL, 35 mmol) sequentially. The resulting mixture was stirred at room temperature for 14 hours, quenched with water, and extracted with CH₂Cl₂ (3×100 mL). Concentration using a rotary evaporator afforded a solid residue. It was purified by column (SiO2, hexane/EtOAc=3:1) to provide 1.5 g of the corresponding isonicotinic aryl ester (59%) as a light yellow solid. A solution of the above isonicotinic aryl ester (1.5 g, 5.88 mmol) in THF (100 mL) was mixed with potassium tert-butoxide (1.384 g, 12.35 mmol) and stirred at reflux for 2 hours. The reaction was quenched with water and acidified with HCl (0.5 N) to pH=6. Extract with CH₂Cl₂ (3×100 mL) followed by concentration using a rotary evaporator afforded a yellow solid residue. It was purified by column (SiO2, hexane/EtOAc=1:1) to provide 1.2 g of the diketone (80%). A solution of the above diketone (1.2 g, 24.71 mmol) in HOAc (100 mL) was stirred at reflux for 2 hours. All the solvent was removed using a rotary evaporator to afford a solid residue. It was then diluted with water and neutralized with NaOH (0.5 N) to pH=8. The solid was collected by filtration and washed with water and hexanes sequentially to afford 1 g of 5-methyl-2-(pyridin-4-yl)-4H-chromen-4-one as a light yellow solid (89%). A solution of 5-methyl-2-(pyridin-4-yl)-4H-chromen-4-one (0.85 g, 3.59 mmol) in dry carbon tetrachloride (250 mL) was mixed with NBS (0.67 g, 3.77 mmol) and benzyl peroxide (0.1 g, 0.422 mmol). The reaction mixture was stirred at reflux for 6 hours. After cooling the solvent was removed and the residue was further washed with hot water to get rid of succinimide. The solid was then purified by column (SiO₂, hexanes/EtOAc=1:1) to yield 0.61 g of bromide (54%). A solution of the above bromide (0.61 g, 1.93 mmol) and NaOAc (1.82 g, 22.15 mmol) in HOAc (50 mL) was stirred at reflux for 6 hours. All the solvent was removed using a rotary evaporator to afford a solid residue. It was then diluted with water, extracted with CH₂Cl₂ (3×100 mL), and concentrated using a rotary evaporator. The solid was purified by column (SiO2, hexanes/EtOAc/MeOH=2:2:1) to yield 0.3 g of the corresponding acetate (53%). A solution of the above acetate (0.3 g, 1.01 mmol) and potassium carbonate (0.414 g, 3.0 mmol) in MeOH (30 mL) and water (3 mL) was stirred at room temperature for 48 hours. MeOH was removed using a rotary evaporator and the resulting mixture was further diluted with water (25 mL) to get a suspension. The solid was collected by filtration and washed with water and hexanes to yield 0.16 g of 5-hydroxymethyl intermediate (65%) as a light yellow solid. A suspension of the above intermediate (0.114 g, 0.45 mmol) in ethyl ether (10 mL) was mixed with HCl in ether (10 mL, 20 mmol) and the mixture was stirred at room temperature for 2 hours to get a even finer suspension. The solid was collected by filtration and washed with hexanes to yield 0.126 g of 5-(hydroxymethyl)-2-(pyridinyl)-4H-chromen-4-one (96%) as a light yellow solid.

The ability of a compound of the present invention to inhibit the expression of VCAM-1, MCP-1, and/or SMC proliferation, or in the treatment of diseases in a host can be assessed using methods known to those skilled in the art, including those described below.

Example 52

MCP-1 and VCAM-1 Assays

Compounds were dissolved in DMSO, aliquoted, and stored at −20° C. Cultured human vascular endothelial cells (HUVECs) were seeded in 96-well plates in complete EGM-2 media (~100 μL/well); cells were plated at ~2-3×10⁵/mL, and were from passage 8 to 12. Cells were incubated overnight. On the following day cells are stimulated with TNF-α (~1 ng/mL) in the presence or absence of compounds dissolved in DMSO. Triplicate wells were used for each test. To establish a dose curve and an IC₅₀, multiple concentrations in 2- to 5-fold increments were used. Cells were exposed to TNF-α and compounds for approximately 16 hours. The next day, cells were visually examined via light microscopy to score for visual signs of toxicity. Cell culture media was analyzed using an MCP-1 ELISA. Cells were refed (~100 μL/well) with 20% CellTiter 96. Aqueous One Cell Proliferation Solution (Promega), 80% EGM-2 medium. Media optical density (at 490 nm) was determined after 1 hour. Plates were aspirated and cell lysates were prepared and these lysates were tested using a VCAM-1 ELISA.

In Table 2, a positive result (+) was defined as at least 50% inhibition of the protein levels MCP-1 or VCAM-1, as determined by the ELISA. For comparison, resveratrol, a naturally occurring polyphenol, demonstrated 47% inhibition of MCP-1 and 54% inhibition of VCAM-1.

Example 53

Smooth Muscle Cell Proliferation Protocol

Compounds were dissolved in DMSO, aliquoted, and stored at −20° C. Human coronary artery smooth muscle cells (CASMCs) were plated in 96-well plates and were grown in SmBM-2 media. After 1-2 hours, media was aspirated and replaced with serum-free ME/F12 media, except the controls. Cells were incubated for a further 48 hours. Compounds were diluted in DME/F12 containing 10% FBS. Media was aspirated from the plates and compounds in DME/F12 containing 10% FBS. Six wells were used per condition and duplicate plates were used. Cells were incubated for a further 72 hours. Media was aspirated from one set of plates; those cells were refed (~100 μL/well) with 20% CellTiter 96 Aqueous One Cell Proliferation Solution (Promega), 80% EGM-2 medium. Media optical density (at 490 nm) was determined after 3-4 hours. In the second set of plates, serum-free DME/F12 media (20 μL) was added to each well. Part of the supernatant (50 μL) was removed and placed in an ELISA plate and was stored temporarily at 4° C. The remaining media and cells in the second set of plates were freeze-thawed for four cycles. The lysates and supernatants were mixed and centrifuged. Part of the supernatant (50 μL) was removed and placed in an ELISA plate. The Promega Cytotox assay was performed on the ELISA plates. The ratio of supernatant OD to supernatant+cell lysate OD was determined.

In Table 2, a positive result (+) was defined as at least 40% inhibition of the proliferation of SMC, as determined by the assay. For comparison, rapamycin, a known inhibitor of SMC proliferation, demonstrated 43% inhibition.

TABLE 2

| Name of Compound | Structure | Concentration | VCAM-1 (% Inhibition) | MCP-1 (% Inhibition) | % Inhibition of SMC Proliferation |
|---|---|---|---|---|---|
| COMPARATIVE COMPOUNDS | | | | | |
| Resveratrol | | 50 uM | 54 | 47 | n/a |
| Probucol | | 10 uM | 19 | 15 | n/a |
| AGI1067 | | 5 uM | 68 | 60 | n/z |
| Taxol | | 100 nM | n/z | n/z | 19 |
| Rapamycin | | 50 uM | n/a | n/a | 43 |
| INVENTIVE COMPOUNDS | | | | | |
| EXAMPLE 1 | 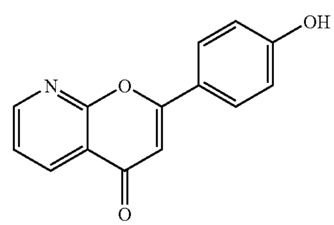 [SMILES: O=c1cc(-c2ccc(O)cc2)oc2ncccc12] | 50 uM | + | − | − |
| EXAMPLE 21 | 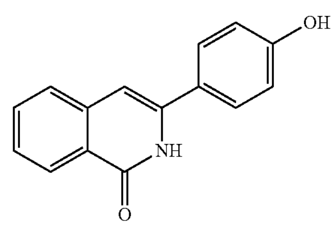 [SMILES: O=c1[nH]c(-c2ccc(O)cc2)cc2ccccc12] | 50 uM | + | + | + |
| EXAMPLE 15 | 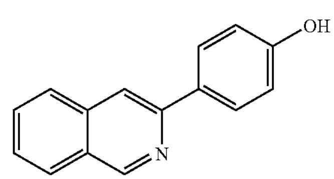 [SMILES: Oc1ccc(-c2cc3ccccc3cn2)cc1] | 50 uM | + | − | − |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 18 | 3-(3-fluoro-4-hydroxyphenyl)-5-methoxy-isoquinolin-1(2H)-one | 50 uM | + | + | + |
| EXAMPLE 32 | 2-(3-bromo-4-hydroxyphenyl)-4H-pyrano[2,3-b]pyridin-4-one | 50 uM | + | — | + |
| EXAMPLE 8 | 2-(4-hydroxy-3-methoxyphenyl)-4H-pyrano[2,3-b]pyridin-4-one | 50 uM | + | — | — |
| EXAMPLE 13 | 2-(6-hydroxypyridin-3-yl)-4H-chromen-4-one | 50 uM | + | — | + |
| EXAMPLE 5 | 2-(4-hydroxy-3-methylphenyl)-4H-pyrano[2,3-b]pyridin-4-one | 10 uM | — | — | — |
| EXAMPLE 11 | 2-(5-hydroxypyridin-2-yl)-4H-chromen-4-one | 50 uM | — | — | — |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 20 | 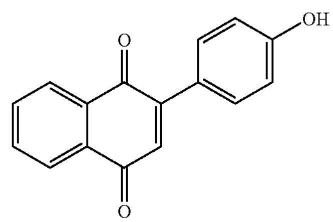 [SMILES: O=C1C=C(c2ccc(O)cc2)C(=O)c2ccccc21] | 10 uM | + | − | − |
| EXAMPLE 49 | 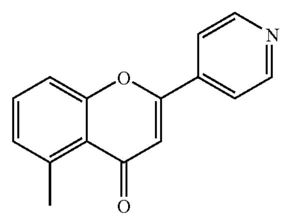 [SMILES: Cc1cccc2oc(-c3ccncc3)cc(=O)c12] | 10 uM | − | − | − |
| EXAMPLE 4 | 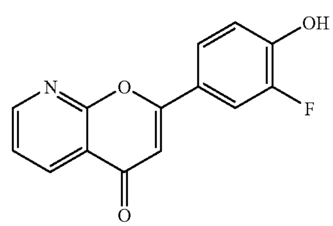 | 50 uM | + | − | − |
| EXAMPLE 7 | 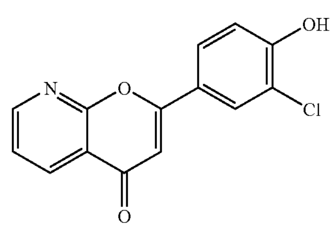 | 50 uM | + | + | + |
| EXAMPLE 28 | 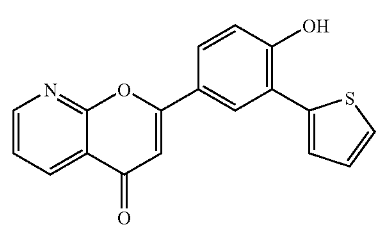 [SMILES: O=c1cc(-c2ccc(O)c(-c3cccs3)c2)oc2ncccc12] | 50 uM | + | − | − |
| EXAMPLE 16 | 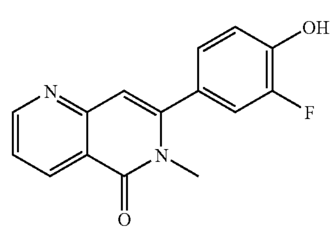 [SMILES: Cn1c(-c2ccc(O)c(F)c2)cc2ncccc2c1=O] | 50 uM | − | − | − |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 17 | 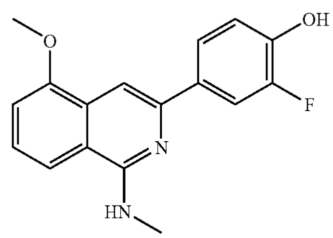 [SMILES: CNc1nc(-c2ccc(O)c(F)c2)cc2c(OC)cccc12] | 50 uM | + | + | − |
| EXAMPLE 51 | 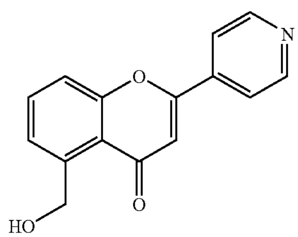 [SMILES: O=c1cc(-c2ccncc2)oc2cccc(CO)c12] | 50 uM | − | − | − |
| EXAMPLE 14 | 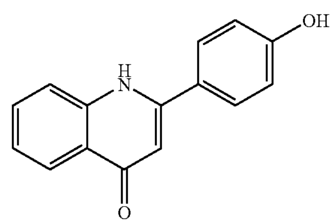 [SMILES: O=c1cc(-c2ccc(O)cc2)[nH]c2ccccc12] | 50 uM | + | + | − |
| EXAMPLE 2 | 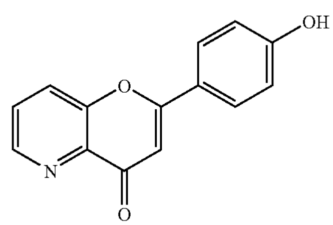 [SMILES: O=c1cc(-c2ccc(O)cc2)oc2cccnc12] | 50 uM | − | − | + |
| EXAMPLE 12 | 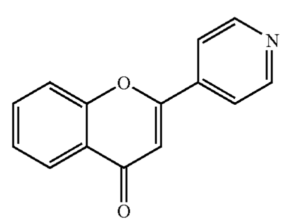 | 50 uM | + | + | + |
| EXAMPLE 3 | 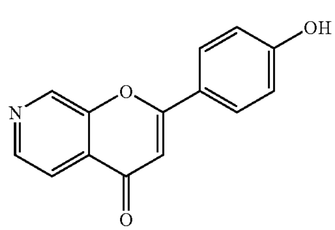 [SMILES: O=c1cc(-c2ccc(O)cc2)oc2cnccc12] | 50 uM | − | − | + |

TABLE 2-continued

| Name of Compound | Structure | Concentration | VCAM-1 (% Inhibition) | MCP-1 (% Inhibition) | % Inhibition of SMC Proliferation |
| --- | --- | --- | --- | --- | --- |
| EXAMPLE 6 | 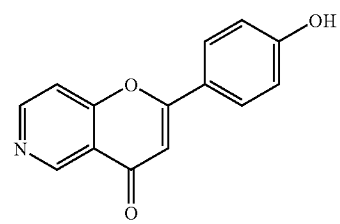 [SMILES: O=c1cc(-c2ccc(O)cc2)oc2ccncc12] | 50 uM | + | − | + |
| EXAMPLE 9 | 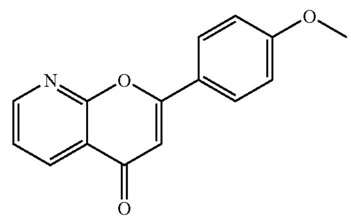 [SMILES: COc1ccc(-c2cc(=O)c3cccnc3o2)cc1] | 50 uM | − | − | + |
| EXAMPLE 10 | 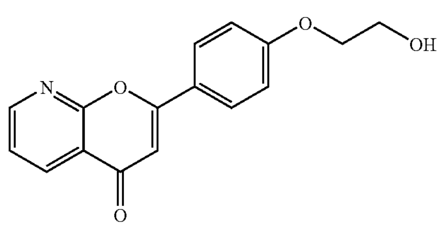 [SMILES: O=c1cc(-c2ccc(OCCO)cc2)oc2ncccc12] | 50 uM | − | − | + |
| EXAMPLE 19 | 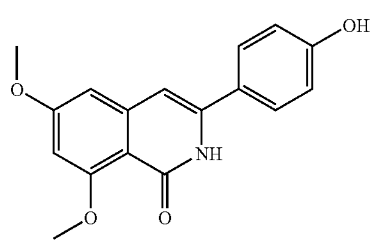 [SMILES: COc1cc(OC)c2c(=O)[nH]c(-c3ccc(O)cc3)cc2c1] | 50 uM | − | + | + |
| EXAMPLE 22 | 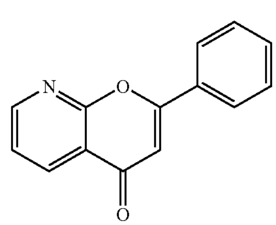 [SMILES: O=c1cc(-c2ccccc2)oc2ncccc12] | 50 uM | − | − | + |
| EXAMPLE 23 | 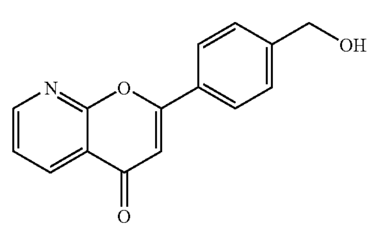 [SMILES: O=c1cc(-c2ccc(CO)cc2)oc2ncccc12] | 50 uM | − | − | + |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 24 | 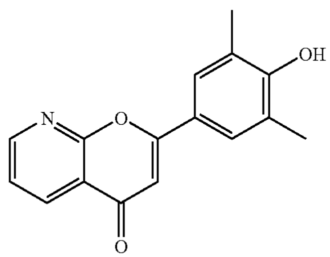 [SMILES: Cc1cc(-c2cc(=O)c3cccnc3o2)cc(C)c1O] | 50 uM | + | + | + |
| EXAMPLE 25 | 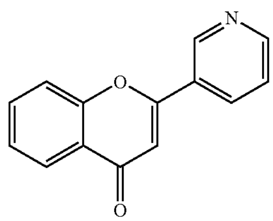 [SMILES: O=c1cc(-c2cccnc2)oc2ccccc12] | 50 uM | − | − | + |
| EXAMPLE 26 | 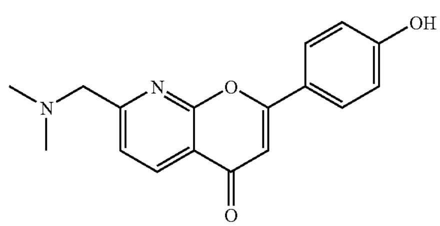 [SMILES: CN(C)Cc1ccc2c(=O)cc(-c3ccc(O)cc3)oc2n1] | 50 uM | − | − | + |
| EXAMPLE 27 | 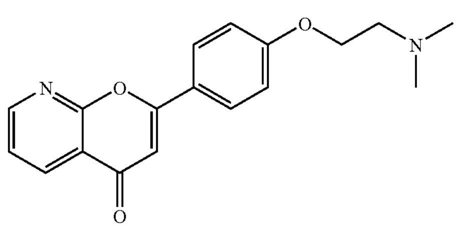 [SMILES: CN(C)CCOc1ccc(-c2cc(=O)c3cccnc3o2)cc1] | 50 uM | − | − | + |
| EXAMPLE 29 | 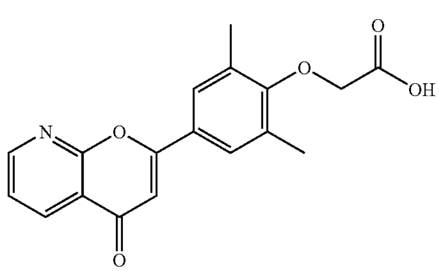 [SMILES: Cc1cc(-c2cc(=O)c3cccnc3o2)cc(C)c1OCC(=O)O] | 50 uM | − | − | + |
| EXAMPLE 50 | 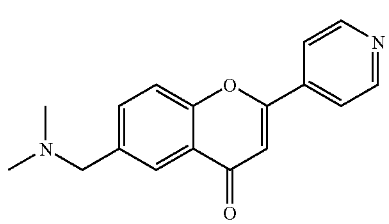 [SMILES: CN(C)Cc1ccc2oc(-c3ccncc3)cc(=O)c2c1] | 50 uM | − | − | + |

TABLE 2-continued
| Name of Compound | Structure | Concentration | VCAM-1 (% Inhibition) | MCP-1 (% Inhibition) | % Inhibition of SMC Proliferation |
|---|---|---|---|---|---|
| EXAMPLE 30 | 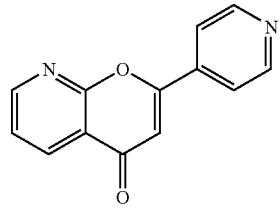 [SMILES: O=c1cc(-c2ccncc2)oc2ncccc12] | 50 uM | − | − | + |
| EXAMPLE 31 | 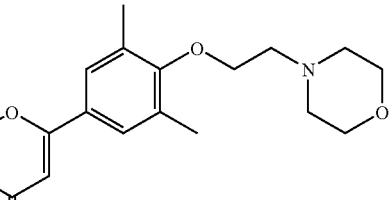 | 50 uM | + | − | + |
| EXAMPLE 33 | 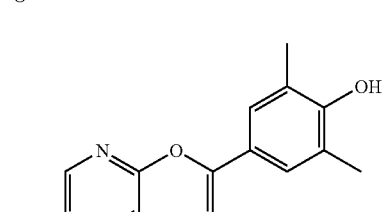 | 50 uM | − | + | + |
| EXAMPLE 34 | 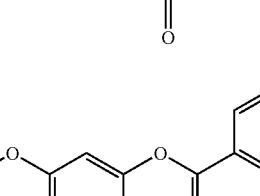 | 50 uM | − | − | + |
| EXAMPLE 35 | 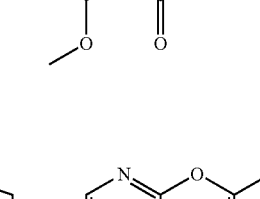 | 50 uM | − | − | + |
| EXAMPLE 36 | 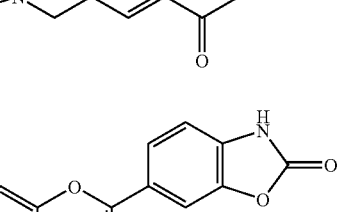 | 50 uM | + | − | + |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 37 | 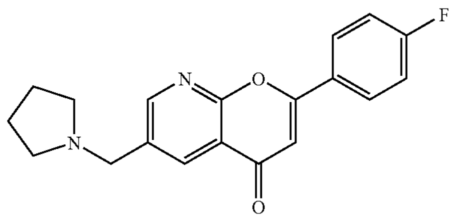 [SMILES: O=c1cc(-c2ccc(F)cc2)oc2ncc(CN3CCCC3)cc12] | 50 uM | + | − | + |
| EXAMPLE 38 | 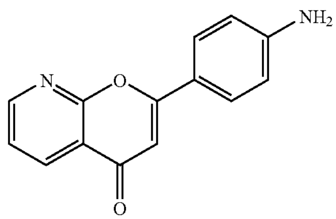 [SMILES: Nc1ccc(-c2cc(=O)c3cccnc3o2)cc1] | 50 uM | − | − | + |
| EXAMPLE 39 | 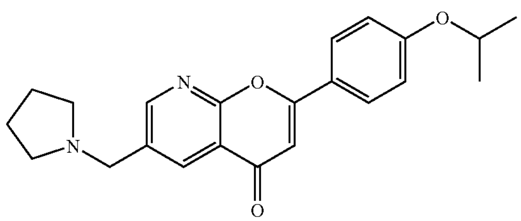 [SMILES: CC(C)Oc1ccc(-c2cc(=O)c3cc(CN4CCCC4)cnc3o2)cc1] | 50 uM | + | + | + |
| EXAMPLE 40 | 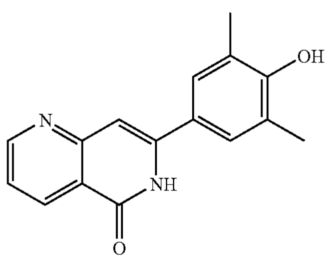 [SMILES: Cc1cc(-c2cc3ncccc3c(=O)[nH]2)cc(C)c1O] | 50 uM | − | − | + |
| EXAMPLE 41 | 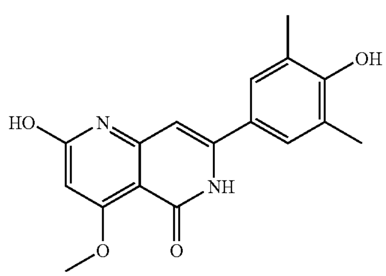 [SMILES: COc1cc(O)nc2cc(-c3cc(C)c(O)c(C)c3)[nH]c(=O)c12] | 50 uM | + | + | + |
| EXAMPLE 42 | 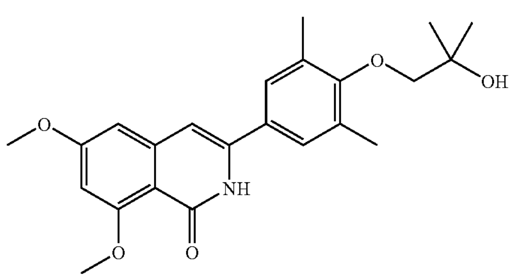 [SMILES: COc1cc(OC)c2c(=O)[nH]c(-c3cc(C)c(OCC(C)(C)O)c(C)c3)cc2c1] | 50 uM | + | − | + |

TABLE 2-continued

| Name of Compound | Structure | Concentration | VCAM-1 (% Inhibition) | MCP-1 (% Inhibition) | % Inhibition of SMC Proliferation |
|---|---|---|---|---|---|
| EXAMPLE 43 | 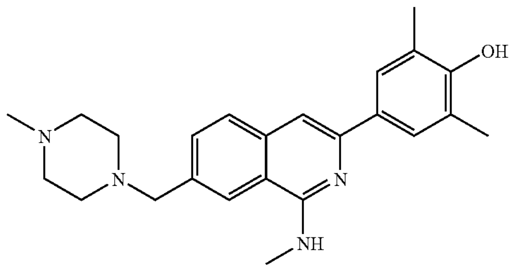 | 50 uM | + | + | + |
| EXAMPLE 44 | 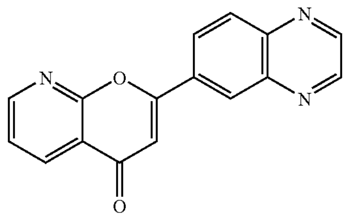 [SMILES: O=c1cc(-c2ccc3nccnc3c2)oc2ncccc12] | 50 uM | + | − | + |
| EXAMPLE 45 | 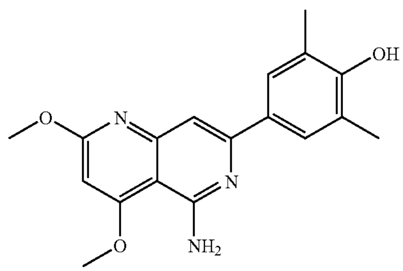 | 50 uM | + | − | + |
| EXAMPLE 46 | 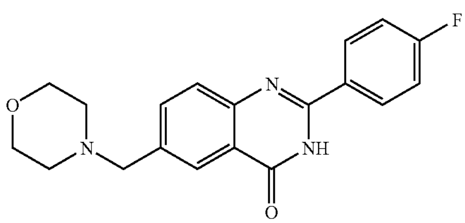 [SMILES: O=c1[nH]c(-c2ccc(F)cc2)nc2ccc(CN3CCOCC3)cc12] | 50 uM | − | − | + |
| EXAMPLE 47 | 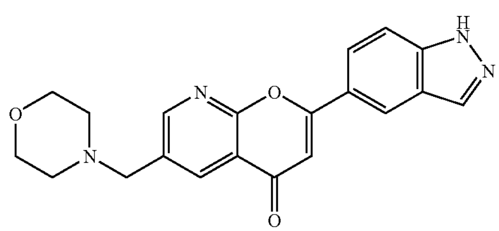 [SMILES: O=c1cc(-c2ccc3[nH]ncc3c2)oc2ncc(CN3CCOCC3)cc12] | 50 uM | − | − | + |
| EXAMPLE 48 | 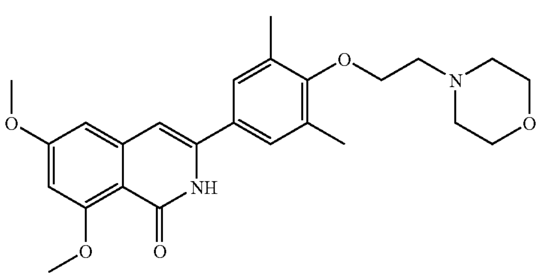 [SMILES: COc1cc(OC)c2c(=O)[nH]c(-c3cc(C)c(OCCN4CCOCC4)c(C)c3)cc2c1] | 50 uM | + | − | + |

Modifications and variations of the present invention relating to compounds and methods of treating diseases will be obvious to those skilled in the art from the foregoing detailed description of the invention. Such modifications and variations are intended to come within the scope of the appended claims. The practice of the present invention employs, unless otherwise indicated, conventional methods of organic and medicinal chemistry, cell and tissue culture, and animal husbandry within the ordinary skill of the art. Such techniques are explained fully in the literature. All publications; patents, and patent applications cited herein are incorporated by reference in their entirety. To the extent the present disclosure is contradictory to the disclosure of PCT/US2005/038048 and/or U.S. provisional application No. 60/704,035, the present application supercedes their disclosure. It is intended that the specification and examples be considered as exemplary only, with a true scope and spirit of the invention being indicated by the following claims.

What is claimed is:

1. A compound selected from
2-(4-hydroxy-3,5-dimethylphenyl)-4H-pyrano[2,3-b]pyridin-4-one;
7-((dimethylamino)methyl)-2-(4-hydroxyphenyl)-4H-pyrano[2,3-b]pyridin-4-one dihydrochloride;
2-(4-(2-(dimethylamino)ethoxy)phenyl)-4H-pyrano[2,3-b]pyridin-4-one dihydrochloride;
2-(4-hydroxy-3-(thiophen-2-yl)phenyl)-4H-pyrano[2,3-b]pyridin-4-one;
2-(2,6-dimethyl-4-(4-oxo-4H-pyrano[2,3-b]pyridin-2-yl)phenoxy)acetic acid;
2-(3,5-dimethyl-4-(2-morpholinoethoxy)phenyl)-4H-pyrano[2,3-b]pyridin-4-one hydrochloride;
2-(4-hydroxy-3,5-dimethylphenyl)-6-(pyrrolidin-1-ylmethyl)-4H-pyrano[2,3-b]pyridin-4-one dihydrochloride;
6-(4-oxo-4H-chromen-2-yl)benzo[d]oxazol-2(3H)-one;
2-(4-fluorophenyl)-6-(pyrrolidin-1-ylmethyl)-4H-pyrano[2,3-b]pyridin-4-one hydrochloride;
2-(4-isopropoxyphenyl)-6-(pyrrolidin-1-ylmethyl)-4H-pyrano[2,3-b]pyridin-4-one hydrochloride;
7-(4-hydroxy-3,5-dimethylphenyl)-1,6-naphthyridin-5(6H)-one hydrochloride;
2-hydroxy-7-(4-hydroxy-3,5-dimethylphenyl)-4-methoxy-1,6-naphthyridin-5(6H)-one dihydrochloride;
3-(4-(2-hydroxy-2-methylpropoxy)-3,5-dimethylphenyl)-6,8-dimethoxyisoquinolin-1(2H)-one;
2,6-dimethyl-4-(1-(methylamino)-7-((4-methylpiperazin-1-yl)methyl)isoquinolin-3-yl)phenol trihydrochloride;
2-(quinoxalin-6-yl)-4H-pyrano[2,3-b]pyridin-4-one;
4-(5-amino-2,4-dimethoxy-1,6-naphthyridin-7-yl)-2,6-dimethylphenol;
2-(4-fluorophenyl)-6-(morpholinomethyl)quinazolin-4(3H)-one;
2-(1H-indazol-5-yl)-6-(morpholinomethyl)-4H-pyrano[2,3-b]pyridin-4-one;
3-(3,5-dimethyl-4-(2-morpholinoethoxy)phenyl)-6,8-dimethoxyisoquinolin-1(2H)-one; and
6-((dimethylamino)methyl)-2-(pyridin-4-yl)-4H-chromen-4-one, and pharmaceutically acceptable salts thereof.

2. A pharmaceutical composition comprising a compound according to claim 1, and a pharmaceutically acceptable carrier.

* * * * *